(12) United States Patent
Bronkema

(10) Patent No.: US 7,725,842 B2
(45) Date of Patent: May 25, 2010

(54) SELF-ATTAINABLE ANALYTIC TOOL AND METHOD FOR ADAPTIVE BEHAVIOR MODIFICATION

(76) Inventor: Valentina G. Bronkema, 1146 19th St., NW., Suite 250, Washington, DC (US) 20036

( * ) Notice: Subject to any disclaimer, the term of this patent is extended or adjusted under 35 U.S.C. 154(b) by 1622 days.

(21) Appl. No.: 10/830,698

(22) Filed: Apr. 23, 2004

(65) Prior Publication Data

US 2004/0247748 A1 Dec. 9, 2004

Related U.S. Application Data

(60) Provisional application No. 60/465,140, filed on Apr. 24, 2003.

(51) Int. Cl.
G06F 3/00 (2006.01)
(52) U.S. Cl. .................. 715/866; 715/751; 715/750; 715/745; 715/744
(58) Field of Classification Search ............... 705/26, 705/25, 13, 20, 10, 14; 715/866, 751, 750, 715/744, 745
See application file for complete search history.

(56) References Cited

U.S. PATENT DOCUMENTS

| | | | |
|---|---|---|---|
| 4,951,197 A | 8/1990 | Mellinger | 600/300 |
| 4,975,926 A | 12/1990 | Knapp | 375/141 |
| 4,992,940 A | 2/1991 | Dworkin | 705/26 |
| 5,250,789 A | 10/1993 | Johnsen | 705/14 |
| 5,285,430 A | 2/1994 | Decker | 368/281 |
| 5,295,064 A | 3/1994 | Malec et al. | 705/1 |
| 5,321,542 A | 6/1994 | Freitas et al. | 398/127 |
| 5,410,326 A | 4/1995 | Goldstein | 348/734 |
| 5,424,524 A | 6/1995 | Ruppert et al. | 235/462 |
| 5,469,206 A | 11/1995 | Strubbe et al. | 725/60 |
| 5,611,051 A | 3/1997 | Pirelli | 705/10 |
| 5,646,608 A | 7/1997 | Shintani | 340/825.52 |
| 5,673,691 A | 10/1997 | Abrams et al. | 128/630 |
| 5,790,295 A | 8/1998 | Devon | 398/202 |
| 5,825,002 A | 10/1998 | Roslak | 235/375 |
| 5,831,664 A | 11/1998 | Wharton et al. | 725/81 |
| 5,833,466 A | 11/1998 | Borg | 434/236 |
| 5,845,282 A | 12/1998 | Alley et al. | 707/10 |
| 5,857,201 A | 1/1999 | Wright, Jr. et al. | 707/104.1 |
| 5,873,045 A | 2/1999 | Lee et al. | 455/556.2 |
| 5,884,215 A | 3/1999 | Birchler et al. | 701/207 |
| 5,897,622 A | 4/1999 | Blinn et al. | 705/26 |
| 5,944,633 A | 8/1999 | Wittrock | 482/4 |
| 5,954,510 A | 9/1999 | Merrill et al. | 434/236 |

(Continued)

FOREIGN PATENT DOCUMENTS

WO  WO 01/20526  3/2001

(Continued)

Primary Examiner—Weilun Lo
Assistant Examiner—Mylinh Tran
(74) Attorney, Agent, or Firm—Burns & Levinson LLP

(57) ABSTRACT

A system and method for behavior modification through dynamic identification of behavior patterns, assistance in finding and implementing healthy alternatives to undesirable behavior patterns, preparation of dynamically variable user-specific programs, monitoring of current user activities, and presenting feedback and information to the user. The system and method further support incorporation of professional and other information into a user-specific package from which the user-specific program is determined, and synchronization and data integrity across the platforms of the system.

36 Claims, 69 Drawing Sheets

U.S. PATENT DOCUMENTS

| | | | |
|---|---|---|---|
| 5,956,693 A | 9/1999 | Geerlings | 705/14 |
| 5,967,789 A | 10/1999 | Segel et al. | 434/236 |
| 5,971,277 A | 10/1999 | Cragun et al. | 235/462.01 |
| 5,982,520 A | 11/1999 | Weiser et al. | 398/126 |
| 6,039,688 A | 3/2000 | Douglas et al. | 600/300 |
| 6,064,502 A | 5/2000 | Burns et al. | 398/129 |
| 6,073,842 A | 6/2000 | Yoshinaga | 235/382.5 |
| 6,078,806 A | 6/2000 | Heinonen et al. | 455/406 |
| 6,083,006 A | 7/2000 | Coffman | 434/127 |
| 6,092,053 A | 7/2000 | Boesch et al. | 705/26 |
| 6,101,483 A | 8/2000 | Petrovich et al. | 705/26 |
| 6,119,935 A | 9/2000 | Jelen et al. | 235/383 |
| 6,123,259 A | 9/2000 | Ogasawara | 235/380 |
| 6,125,352 A | 9/2000 | Franklin et al. | 705/26 |
| 6,129,276 A | 10/2000 | Jelen et al. | 235/383 |
| 6,189,781 B1 | 2/2001 | Yoshinaga et al. | 235/375 |
| 6,199,753 B1 | 3/2001 | Tracy et al. | 235/375 |
| 6,405,318 B1 * | 6/2002 | Rowland | 726/22 |
| 6,439,893 B1 | 8/2002 | Byrd et al. | 434/236 |
| 6,478,736 B1 | 11/2002 | Mault | 600/300 |
| 6,482,156 B2 | 11/2002 | Iliff | 600/300 |
| 6,505,166 B1 | 1/2003 | Stephanou | 705/8 |
| 6,513,532 B2 | 2/2003 | Mault | 600/595 |
| 6,587,835 B1 | 7/2003 | Treyz et al. | 705/14 |
| 6,607,483 B1 | 8/2003 | Holland | 600/300 |
| 6,612,985 B2 | 9/2003 | Eiffert et al. | 600/300 |
| 6,633,869 B1 | 10/2003 | Duparcmeur et al. | 707/6 |
| 6,643,510 B2 | 11/2003 | Taylor | 455/431 |
| 6,656,114 B1 | 12/2003 | Poulsen et al. | 600/300 |
| 6,696,924 B1 | 2/2004 | Socinski | 221/2 |
| 6,769,915 B2 | 8/2004 | Murgia et al. | 434/236 |
| 6,790,178 B1 | 9/2004 | Mault et al. | 600/300 |
| 2002/0006788 A1 | 1/2002 | Knutsson et al. | 455/422 |
| 2002/0052781 A1 | 5/2002 | Aufricht et al. | 705/14 |
| 2002/0055924 A1 | 5/2002 | Liming | 707/100 |
| 2002/0083179 A1 | 6/2002 | Shaw et al. | 709/227 |
| 2002/0086271 A1 | 7/2002 | Murgia et al. | 434/236 |
| 2002/0104087 A1 | 8/2002 | Schaffer et al. | 725/46 |
| 2002/0133378 A1 | 9/2002 | Mault et al. | 705/3 |
| 2003/0108850 A1 | 6/2003 | Murgia et al. | 434/236 |
| 2003/0114943 A1 | 6/2003 | Byrd et al. | 700/91 |
| 2003/0130909 A1 | 7/2003 | Caci | 705/27 |
| 2003/0186202 A1 | 10/2003 | Isenberg | 434/236 |
| 2004/0014014 A1 | 1/2004 | Hess | 434/236 |
| 2004/0067475 A1 | 4/2004 | Niddrie et al. | 434/236 |
| 2005/0097008 A1 | 5/2005 | Ehring et al. | 705/26 |
| 2006/0031114 A1 * | 2/2006 | Zommers | 705/10 |
| 2007/0083441 A1 * | 4/2007 | Harper et al. | 705/26 |

FOREIGN PATENT DOCUMENTS

WO    WO 02/19603 A2    3/2002

\* cited by examiner

USER REGISTRAR with PC Conduit

FEEDBACK PROVIDER flow

PROFESSIONAL INTERFACE flow

EXPERT flow

Note: "PROBLEM" = "identified Type of Behavior"

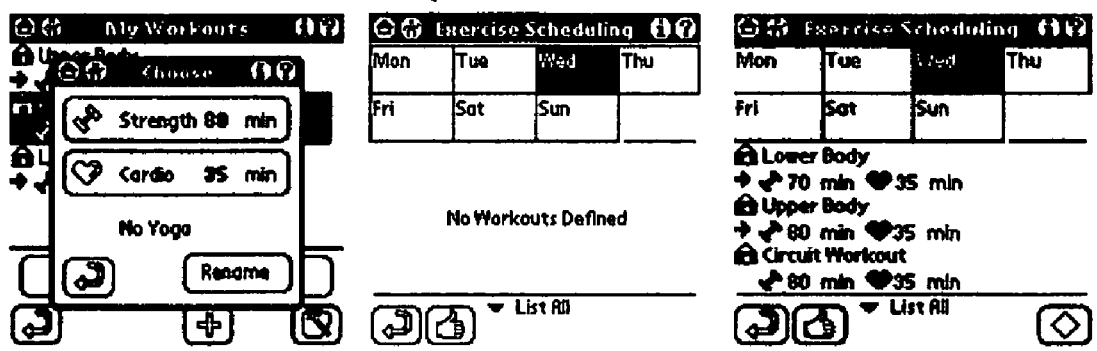
FIG. 14H

FIG. 14K

Web-site Fitness Screens

My Workouts    New Custom Workout    Configure PDA

Recommended:

- Circuit Workout - Strength: 40min, Cardio: 25 min - Home  (By Pro)
- Upper Body - Strength: 30min - Club  (By Sys)
- Lower Body - Strength: 35min - Club  (By Sys)

Custom:

- Custom 1 - Strength: 25min - Home
- Customized 2 - Cardio: 25 min - Trave
- Circuit Customized - Strength: 40min, Cardio: 25 min - Club

Hints:
To view or configure particular pack's data, click on it's name.
- These programs are on the PDA.
- (By Pro) - Pro recommends to do this pack.
- (By Sys) - System recommends to do this pack.

*User Browses His/Her Workouts*

---

My Workouts

Recommended:

- ☑ Circuit Workout - Strength: 40min, Cardio: 25 min - Home  (By Pro)
- ☐ Upper Body - Strength: 30min - Club  (By Sys)
- ☐ Lower Body - Strength: 35min - Club  (By Sys)

Custom:

- ☑ Custom 1 - Strength: 25min - Home
- ☑ Customized 2 - Cardio: 25 min - Trave
- ☑ Circuit Customized - Strength: 40min, Cardio: 25 min - Club

- The packs selected with a checkmark (if any) will be downloaded to your PDA on next sync. The packs you have deselected (if any) will be removed from PDA on next sync.
- All changes will be lost and you will get back to workouts list.

Hints:
To view or configure particular pack's data, click on it's name.
- These programs are on your PDA.
- (By Pro) - Pro recommends you to do this pack.
- (By Sys) - System recommends you to do this pack.

*User configures workouts for PDA*

---

| Filter | ☑ Show Exercise Pictures | | |
|---|---|---|---|

Circuit Workout - Strength: 40min, Cardio: 25 min; for Home    Modify    Create Copy
Strength: 40 min                Recommended  (By Pro)

1. Wide Grip Bench Press  Details
   Weight 5 lbs    Reps: 12    Sets: 3    THR: 75% = 146 bpm
   Comment
   [Exercise picture]

2. Flat Bench Press  Details
   Weight 5 lbs    Reps: 12    Sets: 3    THR: 75% = 146 bpm
   Some User-defined comments truncated to fit single string...
   [Exercise picture]

3. Triceps Kickback  Details
   Weight 5 lbs    Reps: 12    Sets: 3    THR: 75% = 146 bpm
   Comment
   [Exercise picture]

4. Wide Grip Bench Press  Details
   Weight 5 lbs    Reps: 12    Sets: 3    THR: 75% = 146 bpm
   Comment
   [Exercise picture]

Cardio: 25 min

1. Running, 10 ml/h  Details
   Duration: 15 min    THR: 75% = 146 bpm
   Comment
   [Exercise picture]

2. Aerobics, regular  Details
   Duration: 15 min    THR: 75% = 146 bpm
   Some User-defined comments truncated to fit single string...
   [Exercise picture]

FIG. 15E

Select exercise

Show exercises that

Involve Muscle [Upper Body] ☑ Show Exercise Pictures
Use Equipment [Any]

Click on the exercise picture or name to select it

| Exercise picture | Exercise picture | Exercise picture | Exercise picture | Exercise picture | Exercise picture |
|---|---|---|---|---|---|
| Wide Grip Bench Press Details | Flat Bench Press Details | Triceps Kickback Details | Wide Grip Bench Press Details | Flat Bench Press Details | Triceps Kickback Details |
| Exercise picture | Exercise picture | Exercise picture | Exercise picture | Exercise picture | |
| Wide Grip Bench Press Details | Flat Bench Press Details | Triceps Kickback Details | Wide Grip Bench Press Details | Flat Bench Press Details | |

Filter ☑ Show Exercise Pictures

> User selects an exercise to add to workout

---

Circuit Workout for [Home]

Strength  Add Exercise

1. Wide Grip Bench Press Details Insert Exercise Move Up Move Down Delete
Weight [5] lbs  Reps [12]  Sets [3]  THR [75% = 146bpm]
Comment
[Exercise picture]

2. Flat Bench Press Details Insert Exercise Move Up Move Down Delete
Weight [5] lbs  Reps [12]  Sets [3]  THR [75% = 146bpm]
Some User-defined comments truncated to fit single string...
[Exercise picture]

3. Triceps Kickback Details Insert Exercise Move Up Move Down Delete
Weight [5] lbs  Reps [12]  Sets [3]  THR [75% = 146bpm]
Comment
[Exercise picture]

4. Wide Grip Bench Press Details Insert Exercise Move Up Move Down Delete
Weight [5] lbs  Reps [12]  Sets [3]  THR [75% = 146bpm]
Comment
[Exercise picture]

Insert Exercise

Cardio  Add Exercise

1. Running, 10 mi/h Details Insert Exercise Move Up Move Down Delete
Duration [15] mins  THR [75% = 146bpm]
Comment
[Exercise picture]

2. Aerobics, regular Details Insert Exercise Move Up Move Down Delete
Duration [10] mins  THR [75% = 146bpm]
Some User-defined comments truncated to fit single string...
[Exercise picture]

Insert Exercise

FIG. 15F

Analysis and Profile Upgrade Screens

774 — All problems and APs

Hide Calendar ◄ December 2002 — Feb 2003 ►

| Problem / Action Plan | 1 Dec | 7 Dec | 25 Dec | 15 Jan | 30 Jan | 20 Feb | |
|---|---|---|---|---|---|---|---|
| ✦ Possible Misinterpretation of the LH | ▶● | ● | ○ | ○ | ○☐ | N/A | View Graph |
| Refuse to eat if not hungry and upset | | ▶○ | ○ | ○☐ | | N/A | |
| Refuse to snack if not hungry | ▶● | ○ | ○ | ○☐ | | N/A | |
| Delay food intake when upset and had recent food intake | ▶● | ●■▶○ | ○ | ○☐ | | N/A | |
| ✦ Insufficient water intake | | ▶● | ● | ● | ● | ● | View Graph |
| ✦ Irregular meals intake | ▶● | ● | ● | ● | ● | ● | View Graph |

Problem and AP state:
▶ - problem is initially diagnosed or AP is selected as active
○ - no problem
● - possible problem
● - problem
☐ - solved problem / completed AP
■ - active problem / cancelled AP
N/A - not analyzed due to lack of data from user
Empty cell - no active problem / AP Solved problems and completed APs Hide Calendar ◄ December 2002 — Feb 2003 ►

| Problem / Action Plan | 1 Dec | 7 Dec | 25 Dec | 15 Jan | 2 Feb | |
|---|---|---|---|---|---|---|
| ✦ Possible Misinterpretation of the LH | ▶● | ● | ○ | ○ | ○☐ | View Graph |
| Refuse to eat if not hungry and upset | | ▶○ | ○ | ○☐ | | |
| Refuse to snack if not hungry | ▶● | ○ | ○ | ○☐ | | |
| Delay food intake when upset and had recent food intake | ▶● | ●■▶○ | ○ | ○☐ | | |

Problem and AP state:
▶ - problem is initially diagnosed or AP is selected as active
○ - no problem
● - possible problem
● - problem
☐ - solved problem / completed AP
■ - active problem / cancelled AP
N/A - not analyzed due to lack of data from user
Empty cell - no active problem / AP

FIG. 15G

| Name | | From | | | | | | |
|---|---|---|---|---|---|---|---|---|
| | | To | | | | | | |

| Title | Name | Registered | ✉ | RX | ! | P# |
|---|---|---|---|---|---|---|
| Mr | John A. Doe | 01/02/2002 | 2 | | | 3 |
| Ms | Mary F. Smith | 01/05/2002 | | + | | 2 |
| Mrs | Felicia S. Turilli | 01/13/2002 | | + | | 3 |
| Mr | Fabio Lione | 01/23/2002 | 1 | + | | 4 |
| | | | | | | |
| | | | | | | |

Legend

| ✉ | There is a new unread message from the user |
|---|---|
| RX | Patient has prescribed RX |
| ! | Some patient analysis data is out of bonds |
| P# | Number of outstanding problems the analysis has found |
| ⬆⬇X | Sorting (ascending, descending, do not sort) |

| ☒ | Problem | |
|---|---|---|

| # | Problem | Tips |
|---|---|---|
| 4 | Excessive weight | Tips> |
| 2 | Company eating | Tips> |
| 1 | Low self-motivation | Tips> |
| 1 | Unbalanced eating | Tips> |

Legend

| P# | Number of patients with this problem |
|---|---|
| ⬆⬇X | Sorting (ascending, descending, do not sort) |
| Tips> | Assign tips to all patients with this problem |

| Name | | From | | | | | | |
|---|---|---|---|---|---|---|---|---|
| | | To | | | | | | |

| Title | Name | Registered | ✉ | RX | ! | P |
|---|---|---|---|---|---|---|
| Mr | John A. Doe | 01/02/2002 | 2 | | | ○ |
| Ms | Mary F. Smith | 01/05/2002 | | + | | ◐ |
| Mrs | Felicia S. Turilli | 01/13/2002 | | + | | ● |
| Mr | Fabio Lione | 01/23/2002 | 1 | + | | ⊗ |
| | | | | | | |
| | | | | | | |

Legend

| ✉ | There is a new unread message from the user | |
|---|---|---|
| RX | Patient has prescribed RX | |
| ! | Some patient analysis data is out of bonds | |
| ⬆⬇X | Sorting (ascending, descending, do not sort) | |
| P | Patient's problem state | |
| | ○ | Problem just detected |
| | ◐ | Problem is present, AP is in progress |
| | ● | Problem is corrected, AP is finished and is being monitored |
| | ⊗ | Problem is closed |

FIG. 15H

*Welcome,* Billy
Below are the stats from your Personal Data File (PDF)

| | | | |
|---|---|---|---|
| Gender | Male | | |
| Age | 60 | | |
| Smoking (yes/no) | Yes | | |
| Resting Pulse | 120 | | |

| | | | |
|---|---|---|---|
| Recommended Weight | 100-200 lbs | | you're too big, you need to lose some weight so we'll work on this. |
| Advised Daily Calories (RMR) | 2000 c | | |
| Body Mass Index | 27 | | |
| Weight | 200 | | |
| Height | 76 | | |
| Activity Level | Normal | | |

| | | | |
|---|---|---|---|
| Frame Size | small | | |
| Waist / Hip Ratio | 20 | | lets work on this |

| | | | |
|---|---|---|---|
| Medical Conditions | No | | |
| Prescribed Medication | No | | |
| Allergies | Yes | | Allergies are bad |
| Blood Sugar | 205 | | |
| Blood Pressure | 120/200 | | |
| Cholesterol | | | |

©2003 Valentina Bronkema

*Welcome*, Anna Karenina

Weekly enter start date:

◀ 03/01/2003 - 03/07/2003 ▶

Daily Summary: ◀ April 5, 2003 ▶

| Duration | 20 minutes |
|---|---|
| Mood | Excited |
| Exhertion Level | Very Exhausted |

| Cardio | Strength | Yoga | Location |
|---|---|---|---|
| 0 | 15 min | 20 min | Gym | detailed information ▶

| Sun | Mon | Tues | Wed | Thur | Fri | Sat |
|---|---|---|---|---|---|---|
|  |  |  |  | 3<br>200 / 0 | 4<br>1500 / 1000 | 5<br>1200 / 900 |
| 6<br>200 / 0 | 7<br>1500 / 1000 | 8<br>1200 / 900 | 9<br>1200 / 0 | 10 | 11 | 12 |
| 13 | 14 | 15 | 16 | 17 | 18 | 19 |
| 20 | 21 | 22 | 23 | 24 | 25 | 26 |
| 27 | 28 | 29 | 30 | 31 |  |  |

Filter

You can review all of your information. Just choose which ratio you would like displayed in the calendar.

○ Ga Ue andkl lo
○ Bajoen jknela;o djloa
○ jenla doj lakoqpla
○ jfioena lalola jkl
○ jieoaz nbutl npat ○ Duration
  ☐ 0 - 15  ☐ 15 - 30  ☐ 30 - 45  ☐ 45 & up
○ Mood
  ☐ Positive  ☐ Neutral  ☐ Negative
○ Exhertion Level
  ☐ None  ☐ Mildly  ☐ Very Update

FIG. 16G

| Micronutrients | Special Request | Actual Intake | Suggested Intake | %ratio | Condiments | Professional Tips |
|---|---|---|---|---|---|---|
| Zinc | ○ | 20 | 40 | 50% | ✉ | |
| Potassium | ○ | 0 | 40 | 0% | ✉ | |
| Vitamin A | ○ | 0 | 40 | 0% | ✉ | |
| Vitamin D | ○ | 20 | 40 | 50% | | ✉ |
| Vitamin E | ○ | 30 | 40 | 75% | | ✉ |
| Vitamin C | ○ | 40 | 40 | 100% | | |
| Vitamin B | ○ | 0 | 40 | 0% | | |

FIG. 16I

SELF-ATTAINABLE ANALYTIC TOOL AND METHOD FOR ADAPTIVE BEHAVIOR MODIFICATION

CROSS REFERENCE TO RELATED APPLICATIONS

The present application claims priority to U.S. Provisional Application No. 60/465,140 filed Apr. 24, 2003, entitled SELF-ATTAINABLE ANALYTIC TOOL AND METHOD FOR ADAPTIVE BEHAVIOR MODIFICATION which is incorporated herein by reference.

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

BACKGROUND OF THE INVENTION

The present invention relates to an adaptive behavior modification method and system for modifying behavior and, more particularly, to such a system for modifying behaviors that could have an influence on the physical, emotional, psychological, etc. well-being of a person.

Human behavior is a product of environmental factors interacting with pre-disposing individual genetic endowments. Most people have acquired a range of maladaptive behaviors that prevents them from living healthy, satisfied, and fulfilling lives. These maladaptive behaviors can result from, for example, birth order, relationships (or the lack thereof) with siblings, relationships with others, and inadequate or incomplete early emotional connections with authority figures, including the opposite gender parent. These developmental deficits create needs that the adult seeks to fulfill in various adaptive and maladaptive ways. The maladaptive compensations can include the failure to positively self-actualize potential as well as various compulsive dependencies on, for example, food and various substances, such as, for example, among other things, alcohol, tobacco, and drugs, and addictive activities such as gambling, and the like.

It has been generally believed possible to modify, if not alleviate, the undesired behaviors, and, accordingly, various methods for doing so have been developed. These methods include diet programs, drug-dependency programs, smoking cessation programs, and other behavioral modification devices and practices that have enjoyed various levels of popularity in the last one hundred or so years.

For example, there are disclosed in the art hand-held computing devices to log exercise, for example, weightlifting routines, as a way of recording exercises performed and assisting the user in his or her workout program. In a somewhat different manner, there are also disclosed in the art wristwatch-like devices that exhibit indicia (e.g., the word "stop") to serve as a conscious and/or unconscious reminder to the user to stop or otherwise modify an undesired behavior.

While it is probable that a multitude of such programs and behavior-adjusting systems are available, such programs oftentimes are not effective for their intended purpose for long periods of time. Their lack of efficacy may be linked to an inability of the programs/system to adapt to the particular behavioral profile or pattern of the user over time.

An object of the present invention is to provide a system and method to assist a user in dynamically identifying his/her undesirable behavior.

A further object of the present invention is to provide simultaneous data updating for multiple users of mobile interactive systems.

A further object of the present invention is to assist the user in finding and implementing healthy alternatives to undesirable behavior by offering to the user dynamically variable user-specific plans, monitoring and feedback rules, and information.

A still further object of the present invention is to coordinate the use of user physiological and psychological data to determine effective healthy alternative behavior for the user, and dynamically variable paths for the user to reach the healthy alternative behavior.

A yet still further object of the present invention is to provide to the user and a professional or the like with a dynamic interface, allowing the professional to modify the user's information and plan to incorporate professional advice and comments.

A yet still further object of the present invention is to provide the capability to monitor and modify the information received by multiple users operating remotely based on dynamic user profiles.

SUMMARY OF THE INVENTION

The objects set forth above as well as further and other objects are achieved by the present invention. The solutions and advantages of the present invention are realized by the illustrative embodiments of the present invention described hereinbelow.

The system and method of the present invention provide for adaptive behavior self-modification through pre-determined and most commonly identified problem analysis, and dynamic preparation of specific action plans, reminders, and tips. The system and method of the present invention enable user self-analysis and behavior modification with or without professional assistance. The system and method of the present invention enable at least one of the following functionality: (1) an extensible platform for habit and/or behavior pattern analysis in which the habits of the user are determined, stored and analyzed from the ranges of input data provided by the user; (2) a combination of several forms of data collection including, but not limited to, psychological data, physiological data, health-related data, menu/ingredient data, and other data; (3) automatic updates by the system based on direct and indirect user input, and thus the user is relieved of the task of constantly updating data that can be determined by the system; (4) automatic progress monitoring to assess the user's progress and report that progress to the user with respect to identified problems and behavioral patterns for the purpose of helping the user to change habits; (5) automatic voice reminders, such as, for example, from an anthropogenic-like animated character that reacts according to the data provided by the user; (6) automatic reminders that provide acknowledgement of the user's current status with respect to the user's identified problems, and also the status of the implementation of recommended goals, in an entertaining way to help the user reach his/her goals; (7) an e-health letter delivery specifically designed for the user's particular problem; (8) quick access to medical information because the information can be accessed through the use of, but not limited to, a personal device such as a Personal Data Assistant (PDA), a cell phone, or any other such device, or can quickly be loaded to the PDA; (9) quick access to fitness exercise instructions from the PDA; (10) constant and current help, advice, and support from medical professionals or the like which can change each time the personal device is synchronized; (11) dynamic problem updating in which the system is constantly looking for the combinations of data entered by the user that match behavioral habits that are part of a behavior pattern, and constantly updating plans and comments for the user that relate to the user's particular behaviors; (12) notification to help prevent the user from completing an unhealthy pattern at critical times while the user is depending upon the system; (13) individual access and attention to preserve privacy and encourage consistent and truthful use of the system; (14) security and privacy of the user insured through a unique identification system; and (15) a game-like interface to encourage use of the system. It should be realized that the present invention is not limited to the above functionalities which serve as examples of the versatility of this invention.

The system includes at least a personal subsystem, and optionally a multi-user subsystem and permits communication between the two subsystems so that they can exchange data and synchronize information. The system also can provide one or more animated icons or pictographs that simulate various human facial affects, including pleasure, disappointment, sadness, and the like. These icons, which may or may not be anthropologically accurate, can either reflect the inner emotional state of the user in response to intermediate data input or can be designed to provide corrective or prescriptive assistance to the user in changing the undesired behavioral pattern.

The system can accept input data from one or more users and can store the data for later analysis and synchronization with the multi-user subsystem, if present. The multi-user subsystem can accept input from the personal subsystem as well as input from health care providers, such a medical doctors, psychologists, nurses, dietitians, nutrition specialists, fitness advisers, rehabilitation specialists, educators, and the like, who, if present, monitor the activities of one or more users and, if desired, provide prescriptive or proscriptive advice to one or more users through the personal subsystem. The advice can take the forms of, for example, modified or new plans for the user to follow or comments on the user's activity.

The system can remind the user periodically about selected action plans. An automated icon (known as "Charlie", in the illustrative embodiment) can help the user reflect on feelings that the user may experience when attaining or missing action plans. The moment the system recognizes positive changes in the user's behavior and/or mood, Charlie's behavior can reflect, in his mannerisms, the user's behavior and/or mood. Charlie can react to a combination of data entered that relates to the unhealthy habit. In addition, Charlie can alert the user to important information, such as how the user's daily activity impacts the action plans related to the problem. It should be further recognized that this invention is not limited to a single automated icon.

The system can subject personal input data to habit analysis and assessment by which undesired or destructive patterns, if any, are identified. A knowledge engine relates the particular pattern or set of patterns recognized to one or more problems, if any. The system characterizes problems based on pre-selected ranges of user input behavioral data. If the system determines that there is a system-recognizable problem, the system and/or a professional designs a user-specific package for the user that provides the user with a list of, for example, actions plans as well as tips, comments, etc., that the user can access and use. The user can choose to work on a limited number of identified types of behavior, for example, no more than five, by following the plans developed by the system, periodically modified by, for example, an expert, a professional, and others, based on the user's progress. More problems can be addressed later. Each goal has an associated set of action plans that the user agrees to work towards. By organizing goals into action plans, the system focuses the user on aspects of the problem that can seem more attainable psychologically and physically than the entire problem.

The system further automatically configures rules and logic that can help the user to monitor recent information from the medical/research community relevant to the user's situation. The system permits the user to monitor his or her progress and automatically analyzes the user's progress and uses this information to update plans, tips, comments, etc. The system optionally can also allow the user's health professionals to access the user's data, analyze it and introduce changes in the program. In this way, the system provides the health professional with a versatile and adaptable tool in working with the users of the system who are clients of the health professional. In the system of the present invention, professionals can be allowed to change certain rules, but only for a specific group of clients. Other clients and rules can be protected from access.

Operationally, the user, through the system of the illustrative embodiment, provides the capability of collecting preliminary personal information from the user based on a broad range of questions including, but not limited to, for example, behavior, feelings, moods, stress management, health, medical condition, health goals, daily activities, and fitness habits. The examples provided herein are only illustrative of aspects of the invention, and not to be construed as limitations thereon. The system uses the preliminary personal information to provide a customized initial set of interactive functionalities that allow the user to commence data entry. From these data, the system develops a more focused set of functionalities.

During the first time period of use, for example two weeks, the user can enter data into the system, data that include facts, measurements, and specific information associated with health, fitness and temperament. The system includes pre-selected problem-identification rules that are linked to specific behavior patterns. The system uses the problem-identification rules database to produce a personal package that can include a personal profile and a set of practical recommendations, action plans that are uniquely derived for that user. The system then can track the user's status in correcting previously-identified patterns. For example, if the data indicate that the user is not sleeping properly, has a stressful job, is overweight and does not exercise sufficiently, the system can design a step-by-step program of behavioral modification to address the reasons underlying these problems. The system can provide the user with recommendations, integrated and dynamically changing (as a result of user actions) action plans, tips as a result of advance notification rules, continuous monitoring, and compliance advisories to help guide the user to better habits. Importantly, these recommendations and action plans are uniquely derived for that user. The system can help the user, through the system-designed step-by-step program, to adjust the structure of his daily activity to alleviate underlying problems for the long-term. Over succeeding weeks, the user's data are analyzed and the user's profile adjusted to reflect changes in the daily activity, and notifies the user about changes in his habits. If the system finds that the user has overcome the habits related to specific problems after a certain length of time, the user's interaction with the system can change. For example, the user may no longer be notified of tips related to the user's previous problems.

The platform of the present invention can support a method of operation that can include the following steps, but can vary from these steps and still remain within the scope of the present invention: (a) monitoring at least one behavior pattern of a user and (b) analyzing at least one behavior pattern. The method may further include the steps of (c) attempting to identify at least one type of behavior indicative of the at least one behavior pattern and, if the at least one type of behavior exists, (d) associating the at least one type of behavior with the user. The method even further include the steps of (e) comparing the at least one behavior pattern with the identified at least one type of behavior and (f) notifying the user, based upon the comparison, that the user may be able to modify the at least one type of behavior by modifying the at least one behavior pattern. The method may even further still include the step of (g) monitoring the user's activities, patterns, etc., for the continued presence of the at least one behavior pattern. The method can further include the step of (h) repeating steps (e), (f), and (g) until the at least one behavior pattern has been modified according to the expectations presented to the user by the system. Additional steps, as presented in the detailed description, may be incorporated in the method of the present invention without adversely affecting the underlying methodology of the invention.

For a better understanding of the present invention, together with other and further objects thereof, reference is made to the accompanying drawings and detailed description. The scope of the present invention is pointed out in the appended claims.

BRIEF DESCRIPTION OF THE DRAWING

FIGS. 14F-H includes exemplary personal device screen images illustrating the choice of the fitness button, including several subscreen options;

FIGS. 14J-K includes exemplary personal device screen images illustrating the choice of the schedule button and the associated exemplary choices;

FIGS. 14N-O include exemplary personal device screen images illustrating the choice of the 7-day-log button and the associated exemplary choices;

FIGS. 15E-F are illustrative server screen images through which a user or professional could configure a fitness plan for the user;

FIG. 15G is an illustrative server screen image showing analyzed user data for review by, for example, a professional and the user;

FIG. 15H is an illustrative patient summary screen used by professionals to view the status of their assigned patients;

FIG. 16B is a screen image of an exemplary server screen by which a user could view personal information;

FIG. 16E is a screen image of an exemplary server screen used to present 7-day-log daily fitness information;

FIG. 16G is a screen image of an exemplary server screen used to present weekly logged nutrition information;

FIG. 16I is a screen image of an exemplary server screen used to present a list of micronutrients with a mechanism for adjusting the balance of micronutrients;

DETAILED DESCRIPTION OF THE INVENTION

The present invention is a system and method for adaptive behavior self-modification in humans. All examples provided herein are illustrative of aspects of the invention and not for limiting the uses of the system.

Note that the term "professional", as used herein, refers to any type of individual who has some standing in his or her field, either by licensing or other means. The term "expert", as used herein, refers to any type of individual who has the capability and proper authentications to administer the system and change system-wide data. An "individual" can be, where appropriate, human or electronic. The term "external source" as used herein, refers to any type of information that is supplied to the system from sources, for example, human or electronic, outside of the sources explicitly described herein.

Figure 1A:
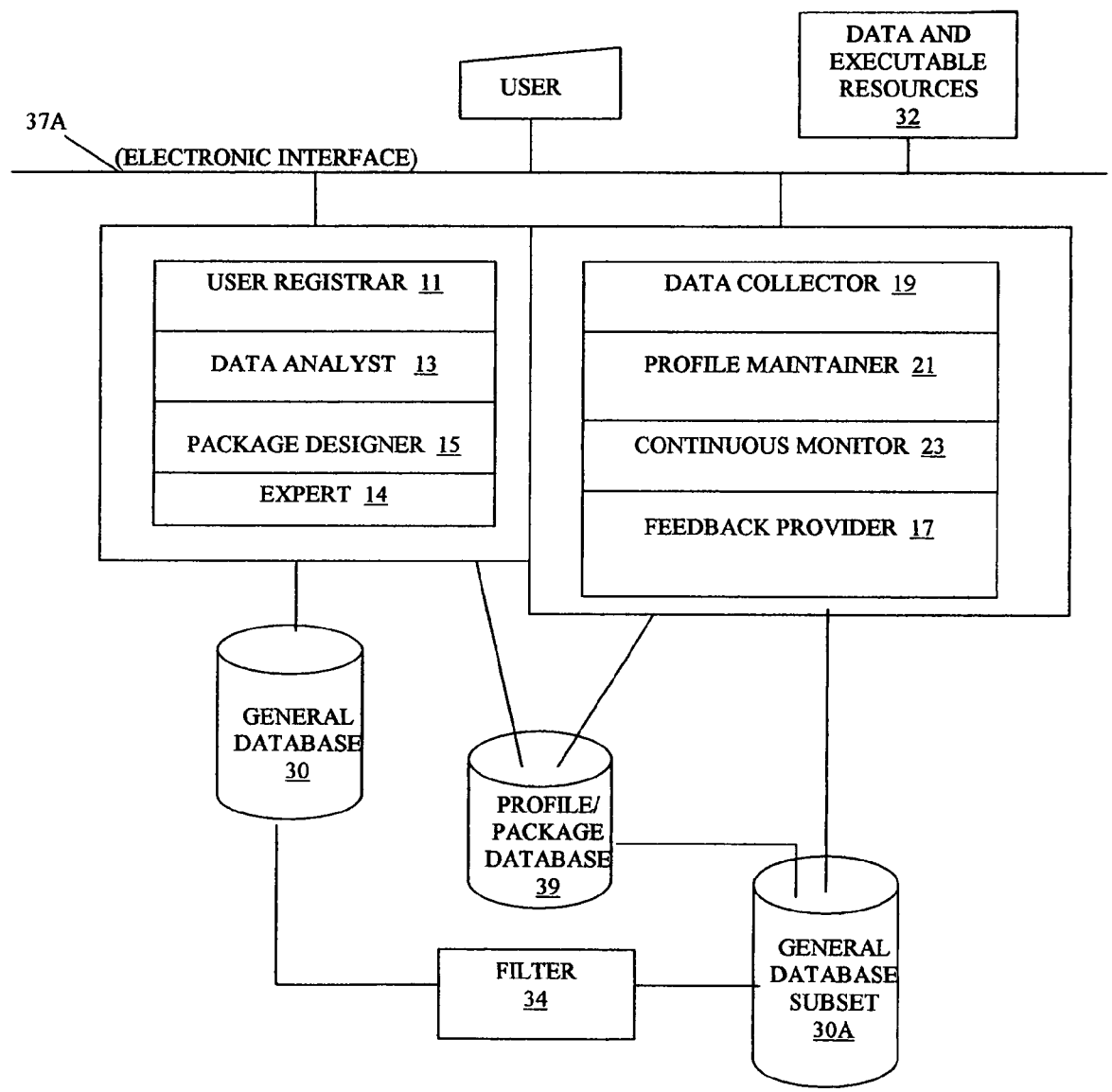
FIG. 1A is schematic block diagram of the distributed computer system and database environment of the illustrative embodiment of the present invention.

Referring to FIG. 1A, the distributed environment and logical database structure of the illustrative embodiment of the present invention are shown. In particular, the illustrative embodiment of the system of the present invention includes a user registrar 11 (see FIGS. 4A-C) to begin the user's interaction with the system and a data collector 19 (see FIGS. 5A-B) to receive data from the user and prepare it for further analysis that is performed by the data analyst 13 (see FIGS. 6A-B). The illustrative embodiment of the system of the present invention can include a package designer 15 (see FIGS. 8A-B) that also can receive data and can prepare and continually update a user-specific program which can be a set of action plans, tips, etc. tailored to the user's current situation. The illustrative embodiment of the system of the present invention can further include a feedback provider 17 (see FIGS. 8C-D and 9A-B) that communicates information to the user that is also tailored to the user's situation, gender, age, etc. The illustrative embodiment of the system of the present invention can further include a profile maintainer 21 (see FIGS. 7A-B) that tracks and records adjustments in the characteristics of the user as time goes on. The illustrative embodiment of the system of the present invention can also include a continuous monitor 23 (see FIGS. 10A-B) that monitors the progress of the user at overcoming identified types of behavior, and searches for the possibility of a new behavioral pattern. These components can interact with each other, through, for example, electronic interface 37A, and certain databases to retrieve, record, and continually update information of interest to the system and the user. General database 30 can be initially populated with information and rules that could be of general interest to individuals exhibiting certain types of behavior. General database 30 can be updated manually or automatically as information and rules change. As the system becomes cognizant of the particular characteristics and habits of a given user, and as data are analyzed and user-specific packages 1151 (FIGS. 13A/C) are created, profile/package database 39 and filter 34 are populated and continually updated for the given user. Profile/package database 39 can contain user-specific information that the system creates and continuously updates. Filter 34 can select a subset of general database 30 that is of particular interest to the given user. General database subset 30A can be created as a result of the application of filter 34 to general database 30. Data and executable resources 32 can be made available to the user and system for populating and updating general database 30 and profile/package database 39, and also for creating filter 34 and for other purposes.

Figure 1B:
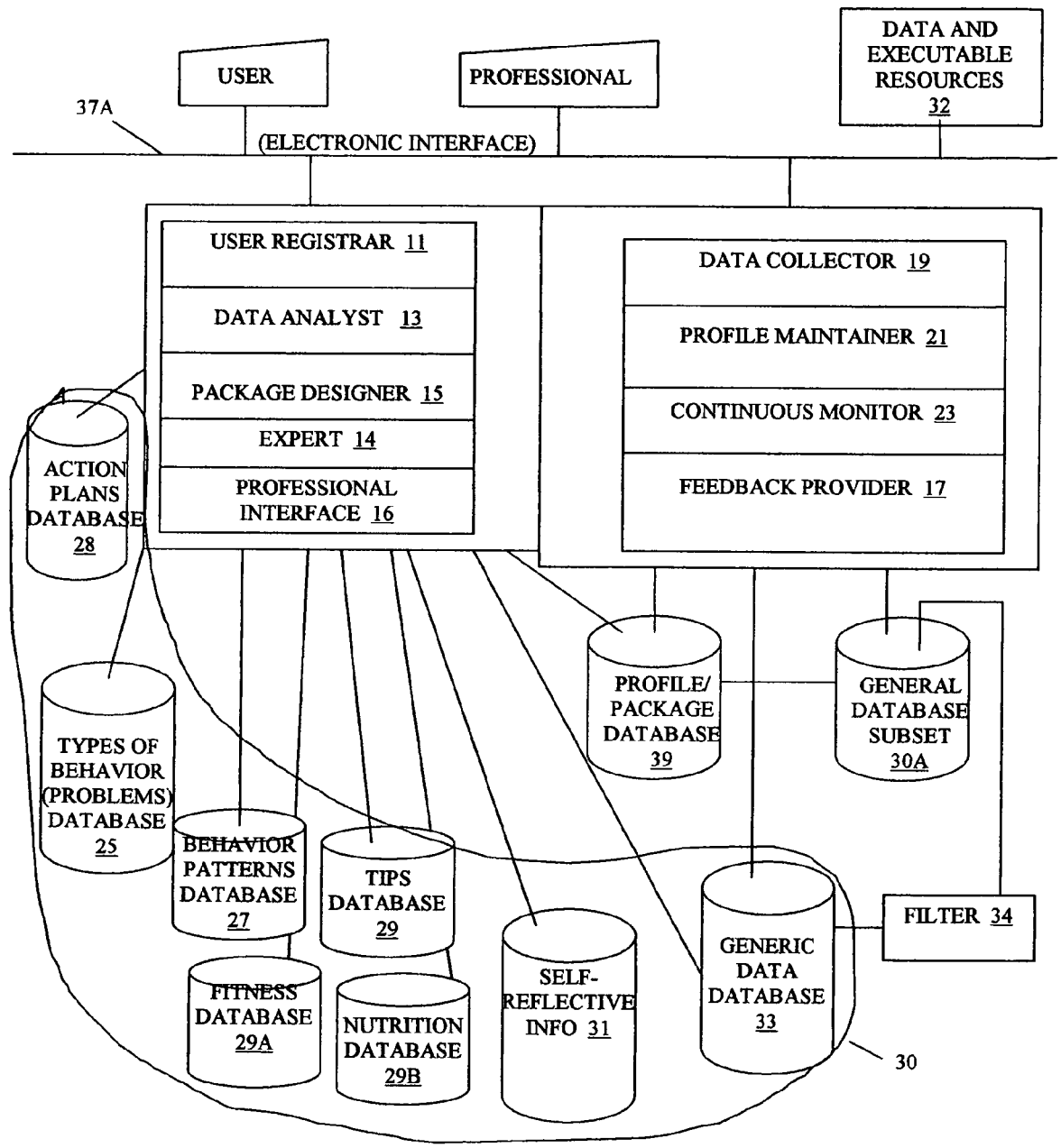
FIG. 1B is a schematic block diagram of the distributed computer system and database environment of a specialized embodiment of the present invention including a professional interface and specific databases.
Figure 11A:
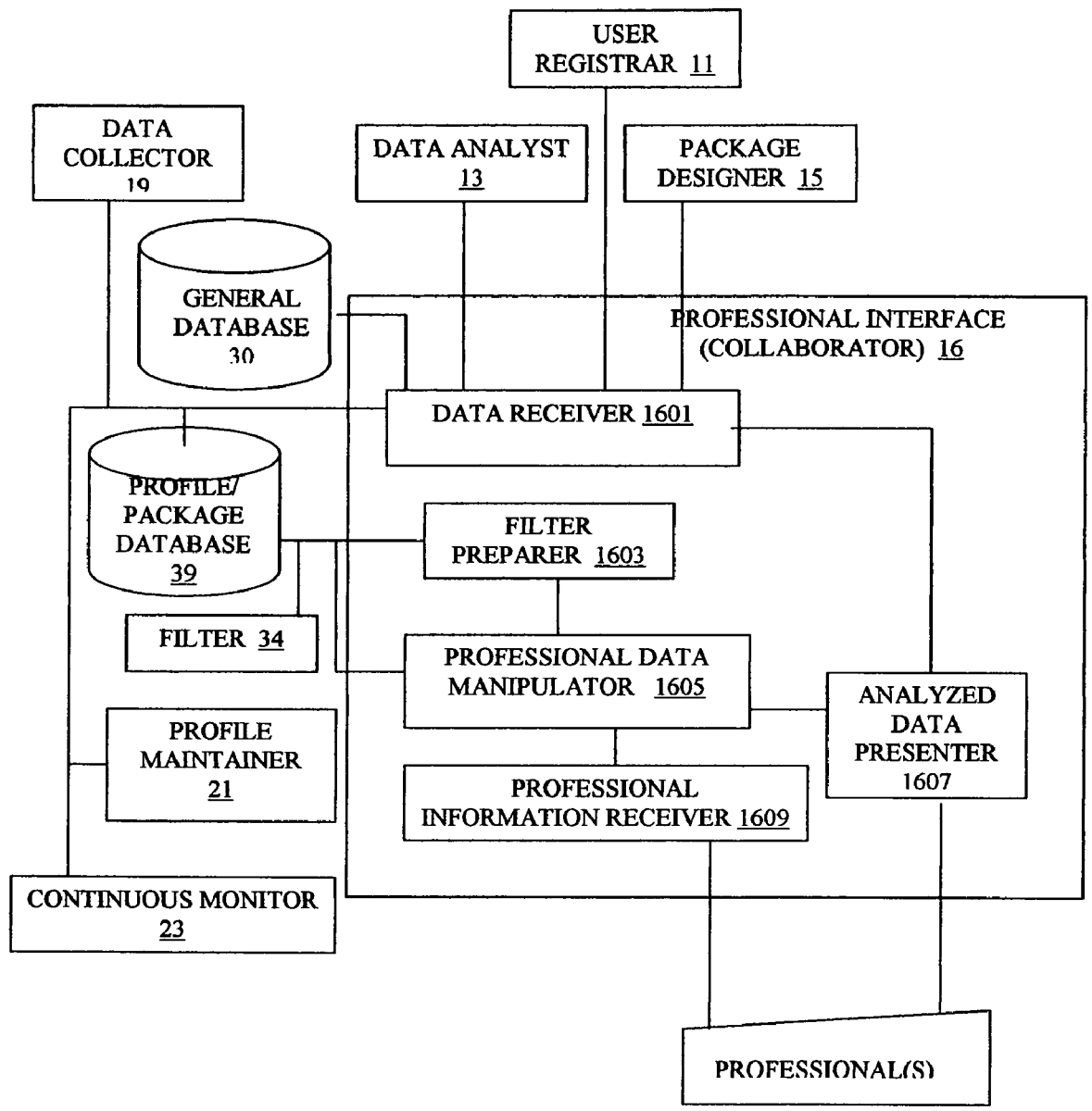
FIG. 11A is a schematic block diagram of the professional interface of the illustrative embodiment of the present invention.
Figure 11B:
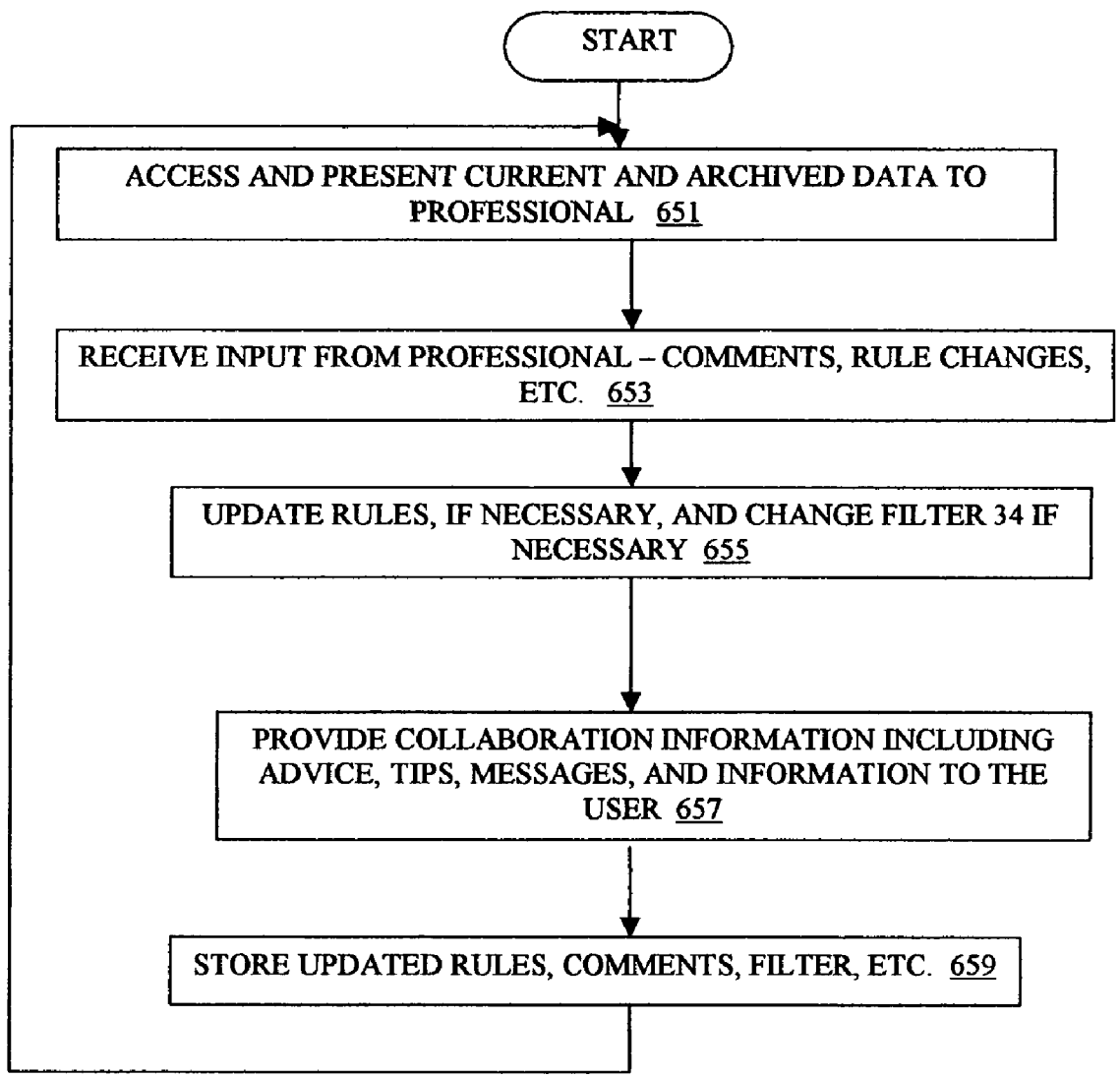
FIG. 11B is a flowchart of the professional interface of the illustrative embodiment of the present invention.
Figure 11C:
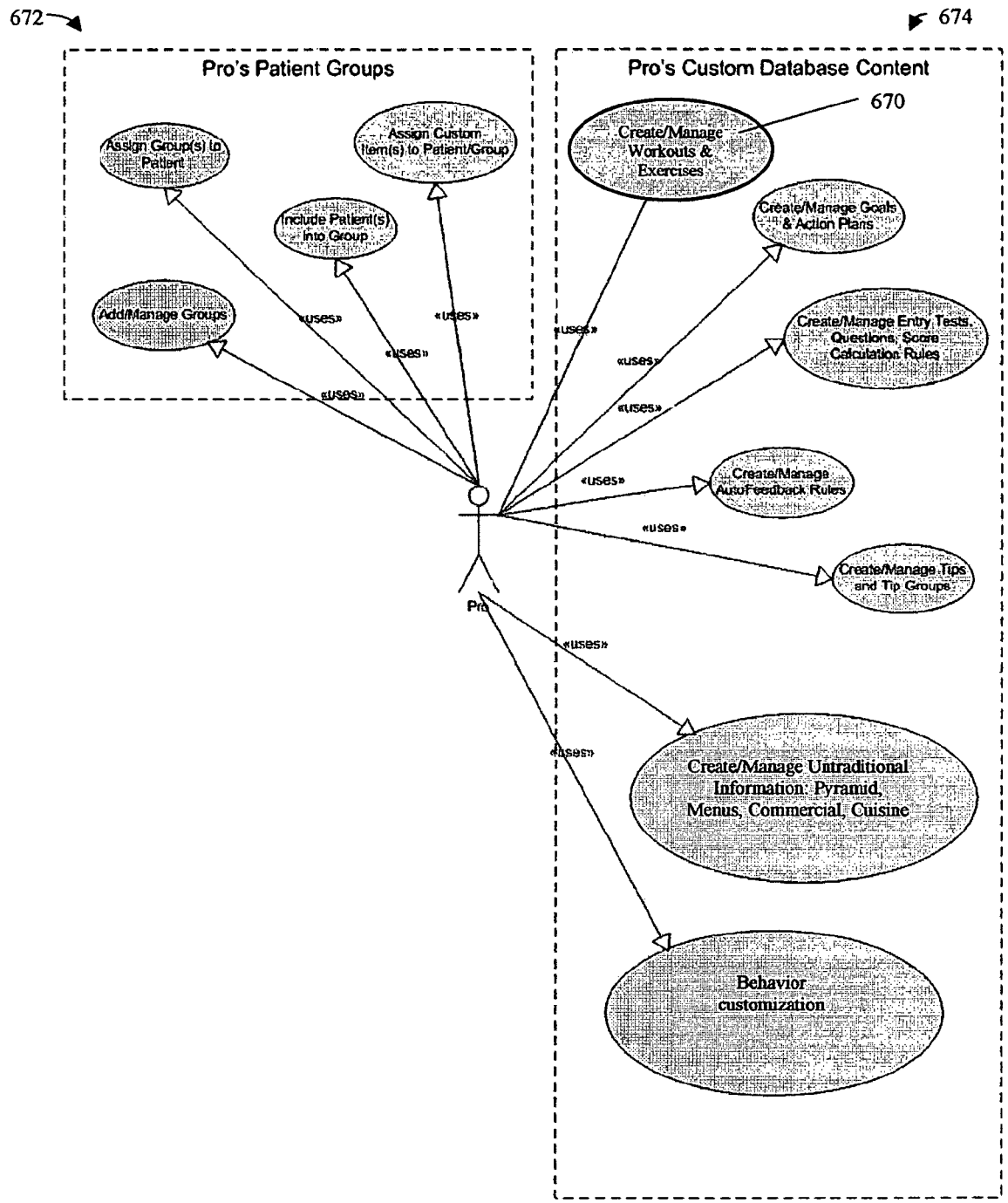
FIG. 11C is a bubble diagram of some of the possible functions that can be performed by the professional.

Referring now to FIG. 1B, the system of the present invention can optionally include expert 14 (see FIGS. 12A-B) and professional interface 16 (see FIGS. 11A-C). Expert 14 provides for updating and automatic proliferation of system-wide database changes that are manually or automatically initiated. Expert 14 can insure database integrity across the system, both in the multi-user (or server or website) system and in the remote personal devices. Professional interface 16 can provide an interface between the user and the professional or other external source of user-specific or other information, and analysis tools to support professional or other analysis, including general database 30 information and rules changes. Data analyst 13 can provide data to professional interface 16 which allows one or more professionals to evaluate the user's situation and provide professional advice. Within general database 30 can be many types of applicable databases, including, for example, types of behavior database 25, behavior patterns database 27 indicative of the types of behavior, tips database 29 associated with behavior patterns database 27, action plans database 28 associated with behavior patterns database 27 and types of behavior database 25, fitness database 29A, nutrition database 29B, and self-reflection information 31 are used by various components in the system. Generic database 33 can hold information that could be applicable to all users, such as menus and ingredients from restaurants, and their associated micronutrients and other characteristics developed by the system and received from other sources. General database 30 can be extended to include any other applicable data.

Figure 2A:
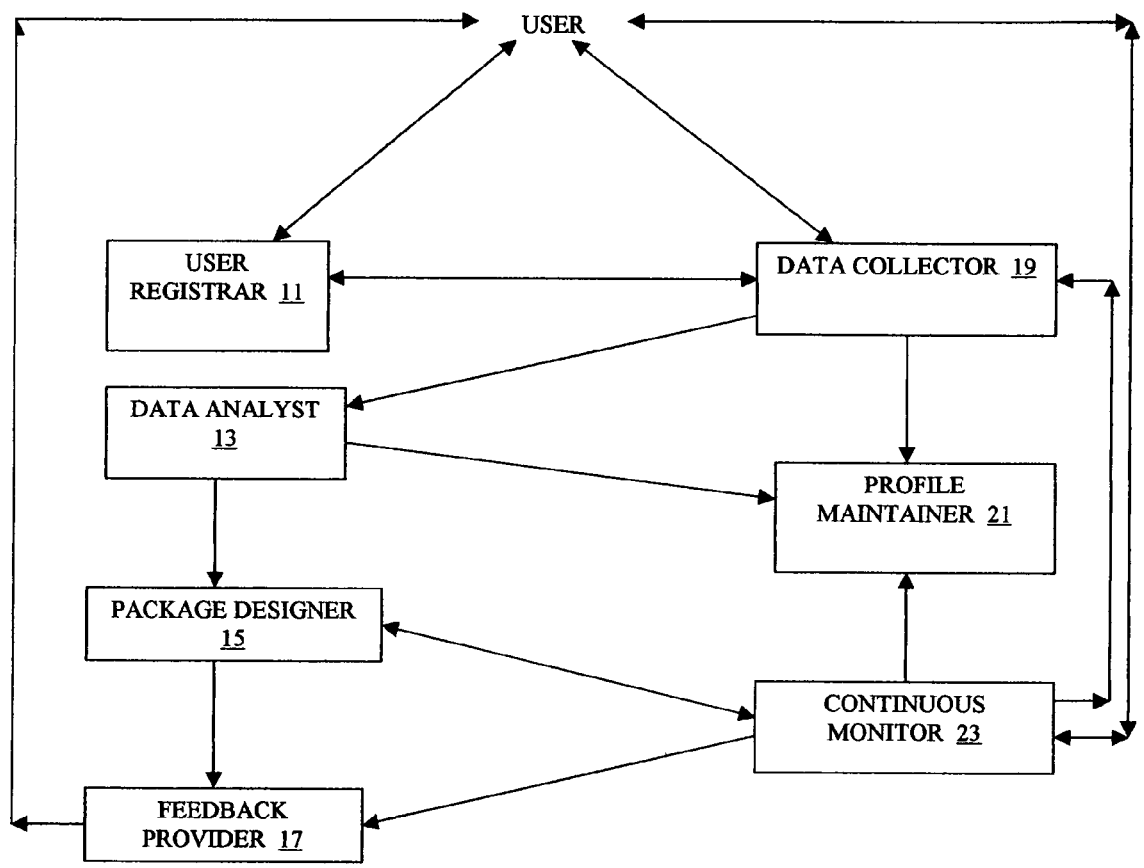
FIG. 2A is a data and control flow diagram of the major components of the system of the present invention.

Referring now to FIGS. 2A-D, the flow of data and control among system components and with the user are shown. In particular, and referring primarily to FIG. 2A and the exchange of control, the user interacts with user registrar 11 (FIG. 2A) by providing login information, and with data collector 19 (FIG. 2A) by providing such personal information as, for example, characteristic and behavior data. User registrar 11 can manage the synchronization of data across the system. Data analyst 13 (FIG. 2A) can receive data from data collector 19 and analyzes the user's behavior, providing analyzed data and any recognized types of behaviors to profile maintainer 21 (FIG. 2A) and package designer 15 (FIG. 2A). Profile maintainer 21 can monitor data with respect to the characteristics of the user, including personal, physical, and behavioral data, data analysis results, and types of behavior. Package designer 15 can create and can continually update a user-specific program including customized set of tips, action plans, and animations based on the user's collected and analyzed data, and also based on the types of behavior identified according to the user's habitual behavior. Package designer 15 can exchange data with continuous monitor 23 (FIG. 2A) and can provide data to feedback provider 17 (FIG. 2A) so that they might, respectively, continue to prescreen against any possible recognized patterns, and assist the user in modifying the user's behavior through, for example, self-reflection, alarms, and health-related information. The user can interact with continuous monitor 23 (FIG. 2A) by providing updates concerning the user's current activities. Feedback provider 17 (FIG. 2A) can present the user with feedback, which can include a self-reflective device (see FIGS. 8C/D), concerning the user's progress with respect to identified types of behavior.

Figure 2B:
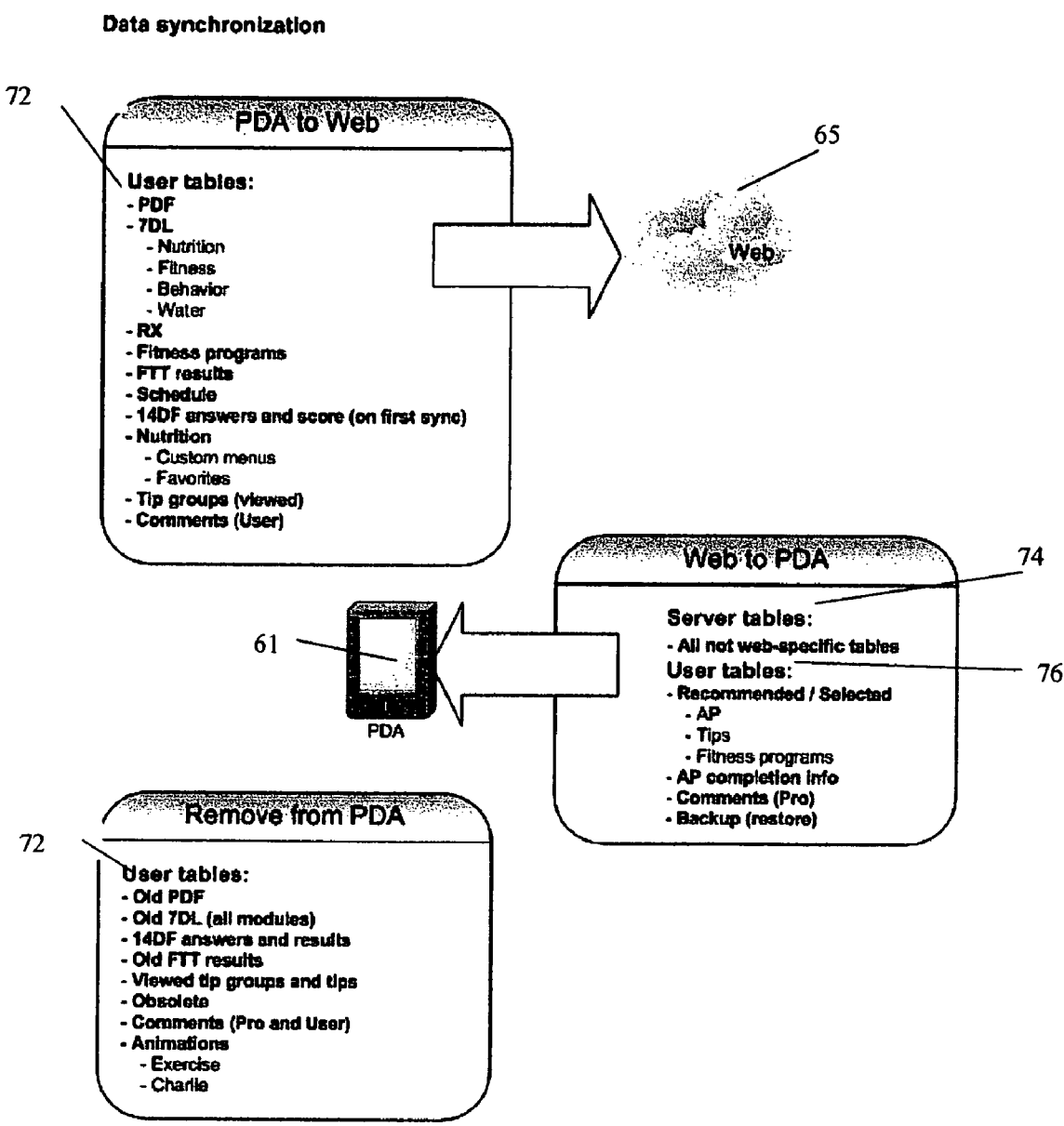
FIG. 2B is a pictographic chart of the flow of exemplary data between the personal device and the server.
Figure 2C:
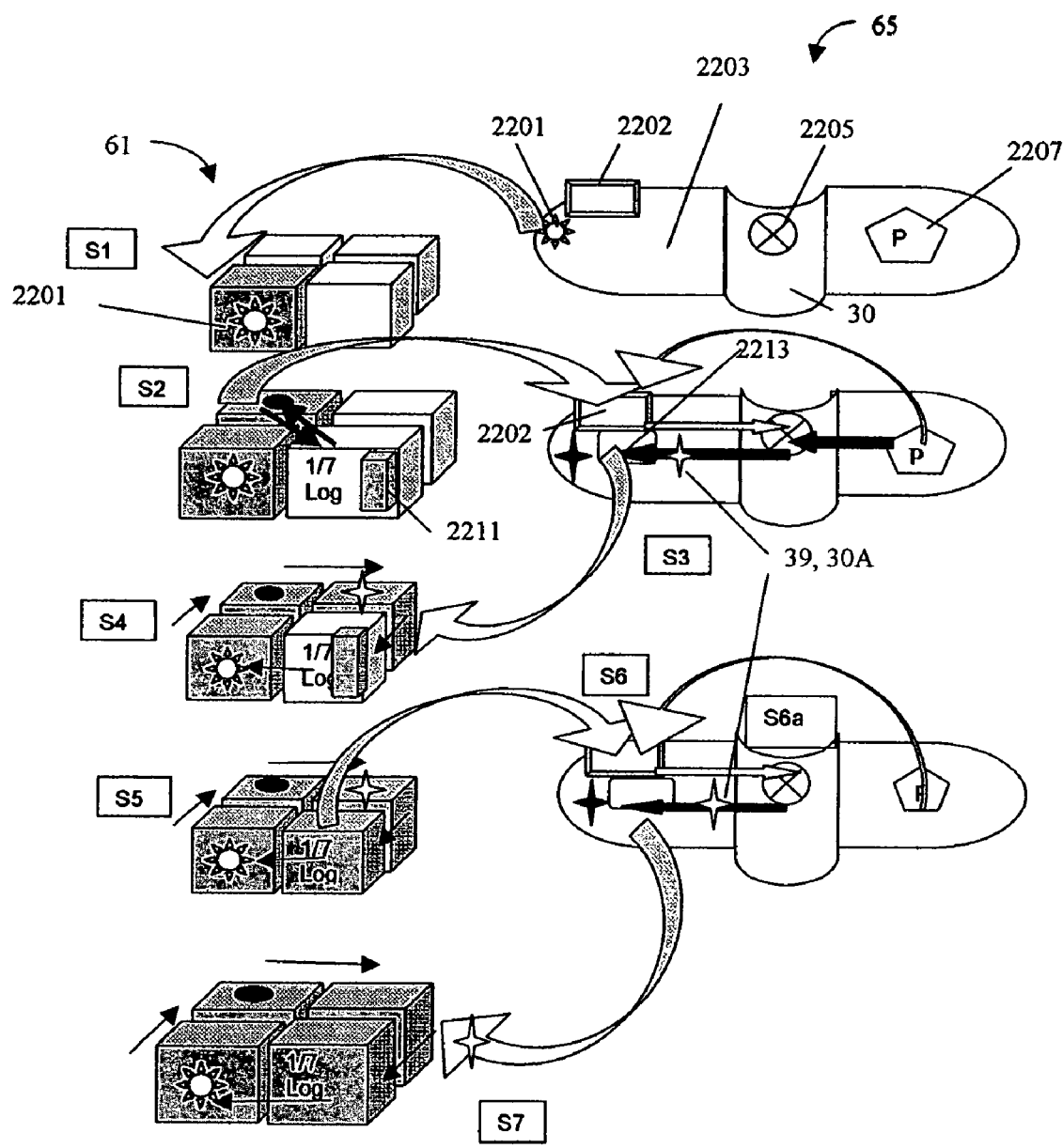
FIGS. 2C and 2D are schematic diagrams of the sequence of data exchange and update between the personal device, referred to illustratively as the PDA, and the multi-user system, known also herein as the server.
Figure 2D:
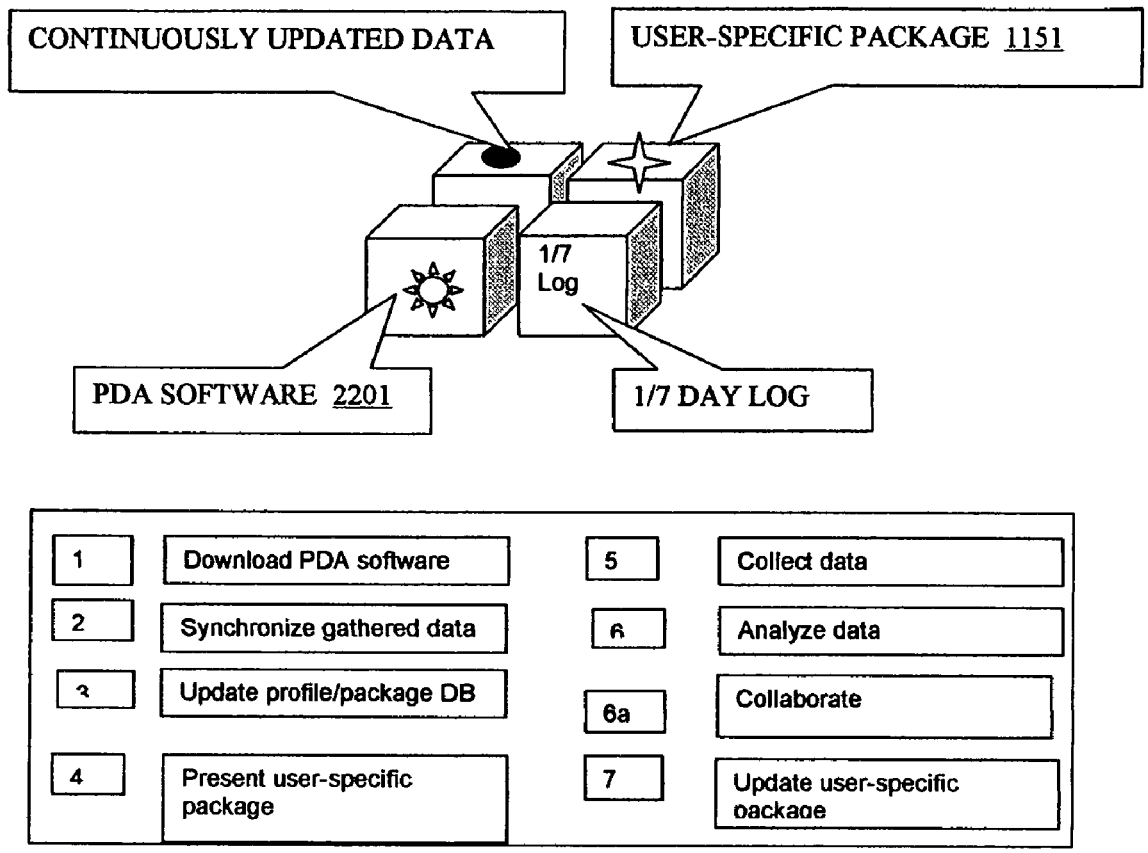

Referring primarily to FIGS. 2B-D, while control is exchanged among the various components of the system, data are also exchanged as they are updated and analyzed. Personal device user tables 72 (FIG. 2B) can be transferred, for example, from personal device 61 (for example, a PDA (FIG. 2B)) to a multi-user device (for example, server 65 (FIG. 2B)), for analysis. The data can be analyzed and stored in general database 30 (FIG. 2D) and profile/package database 39 (FIG. 2D), which are here illustratively shown as server tables 74 (FIG. 2B) and server user tables 76 (FIG. 2B). These data transfers are illustrated in FIGS. 2C/D in which personal device software 2201 (FIG. 2C) is transferred to personal device 61 (for example, a PDA) (FIG. 2C) in step S1.

Continuing to refer primarily to FIGS. 2C-D, the user may enter data into personal device 61 for a period of time, and then the data are transferred to profile/package data collection area 2202 (FIG. 2C) in step S2. User-specific data software 2205 (FIG. 2C) can be placed in profile/package analyzed data area 2213 (FIG. 2C) to be transferred back to personal device 61 in step S4. Data can be continually collected on personal device 61, and, after a period of time or during synchronization, for example, can be transferred to profile/package data collection area 2202 in step S5. In step S6, user-specific data software 2205 can create and update user-specific data 1151 (FIGS. 13A/C) that can be built from profile/package database 39 (FIG. 1A), user-specific filter 34 (FIG. 1A), general database 30, and other sources. In step S6a, information from the professional's private area 2207 (FIG. 2C) can be used to update data that can be used during analysis and could eventually be sent to personal device 61 (a process referred to herein as "collaboration"). In step S7, profile/package database 39 (FIG. 2D) and general database subset 30A (FIG. 2D) can be sent to personal device 61 during synchronization. A user may access user-specific information on server 65 (FIG. 2D) in user private area 2203 (FIG. 2C). As shown, the professional can update both the user-specific information 1151 (FIG. 2C), through user-specific data software 2205 (FIG. 2C), and profile/package data collection area 2202 (FIG. 2C), and can access information from both within the system and outside the system.

To augment the user-specific information and promote the user's continued adherence to the user-specific program, restaurant menu data including ingredients could be accessed by the system. These data could be available through, for example, an electronic interface or by system-enabled manual entry by, for example, a chef, or any other appropriate means. In any case, the menus and ingredients could vary as needed and the system can provide means for real-time menu and ingredient updates. With the ingredient list, the system could determine the micronutrient profile associated with the menu items. A user could be presented with a selection of restaurant offerings that would serve food that complements the user's diet plan, for example, or simply a list of restaurants available to the user that serve food that the user prefers. Note that other services could provide similar functionality to the user through interfaces provided by the system to process incoming information and make it available to specific users. The examples provided herein do not limit the invention to particular configurations.

Figure 3:
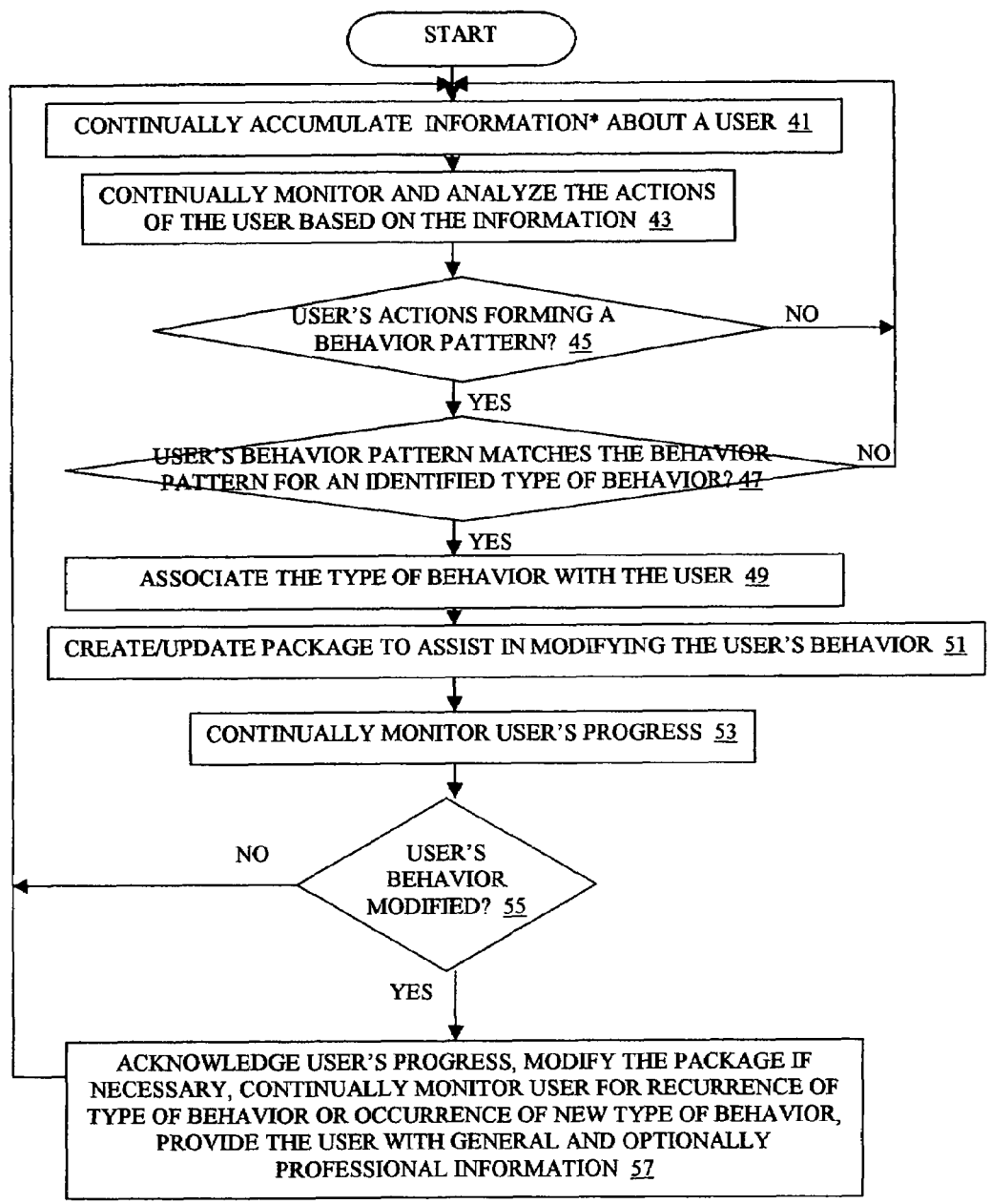
FIG. 3 is a flowchart of the method of the present invention.

Referring now to FIG. 3, the method of the present invention is given. The can include, but is not limited to, a series of illustrative steps provided below, which may be varied in accordance with the present invention. For example, the method of the present invention can include the step of continually accumulating personal, physical, and behavioral information from the user (method step 41). In this step, the user may provide information such as, for example, gender, age, height, weight, food intake information, mood, psychological data, location, possible thoughts and beliefs, and exercise information. These data may be collected over a continuous period such as, for example, 14 days. The method may further include the step of continuously monitoring and analyzing the user's behavior inferred from data collected in the previous step (method step 43). In this step, the system compares the habitual behavior of a user to a customizable list of possible behavior patterns that indicate a type of behavior. If the user's actions are not indicative of at least one type of behavior (decision step 45), the method can further include the step of repeating method steps 41 and 43, and decision step 45. If the user's behavior is indicative of at least one type of behavior (decision step 45), and the user's behavior pattern matches the behavior pattern for at least one identified type of behavior (decision step 47), the method can further include the step of associating the at least one type of behavior with the user (method step 49). In this step, if the user's profile and activities contain enough indications (shown in FIG. 13B as minimum data requirements decision box 1103A) of at least one type of behavior, the system can associate, for a time, that type of behavior with the user. If the user's behavior does not match the behavior pattern for at least one identified type of behavior (decision step 47), the method can further include the steps of repeating method steps 41 and 43 and decision steps 45 and 47. The method can further include the steps of creating/updating a package to assist in modifying the user's behavior (method step 51) and continually monitoring the user's progress as measured against, for example, a user-specific program from the package (method step 53). If the user successfully modifies her behavior (decision step 55), the method can further include the step of acknowledging the level of the user's improvement, modifying the package if necessary, continually monitoring the user's behavior for recurrence of at least one identified type of behavior, or for the occurrence of at least one new type of behavior, and providing the user with general, and optionally professional, information (method step 57). The method may continue at method step 41. If the user does not successfully modify her behavior (decision step 55), the method can resume execution at method step 41.

Figure 4A:
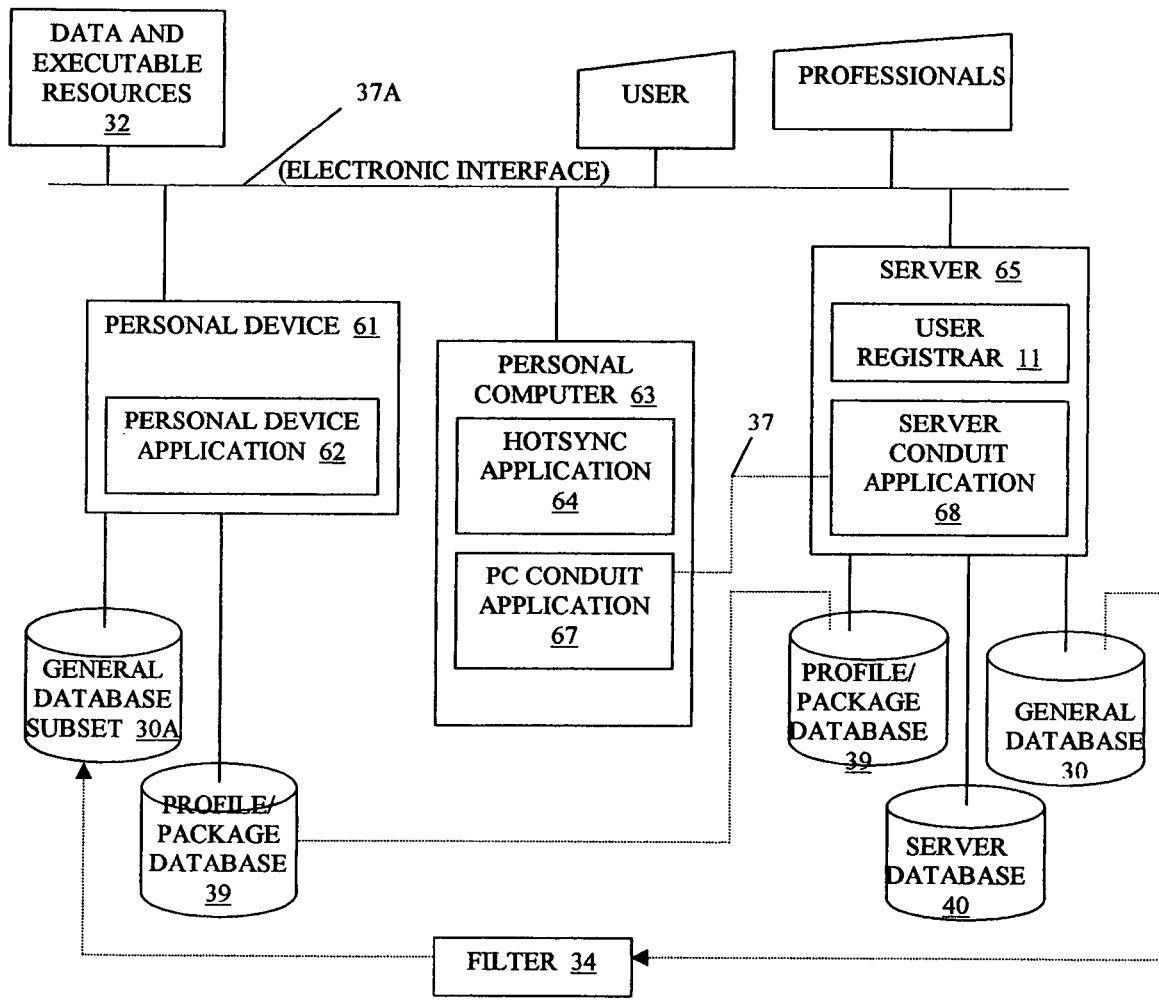
FIG. 4A is a schematic block diagram of the user registrar and conduit for synchronization in a personal computer environment of the illustrative embodiment of the present invention.
Figure 4B:
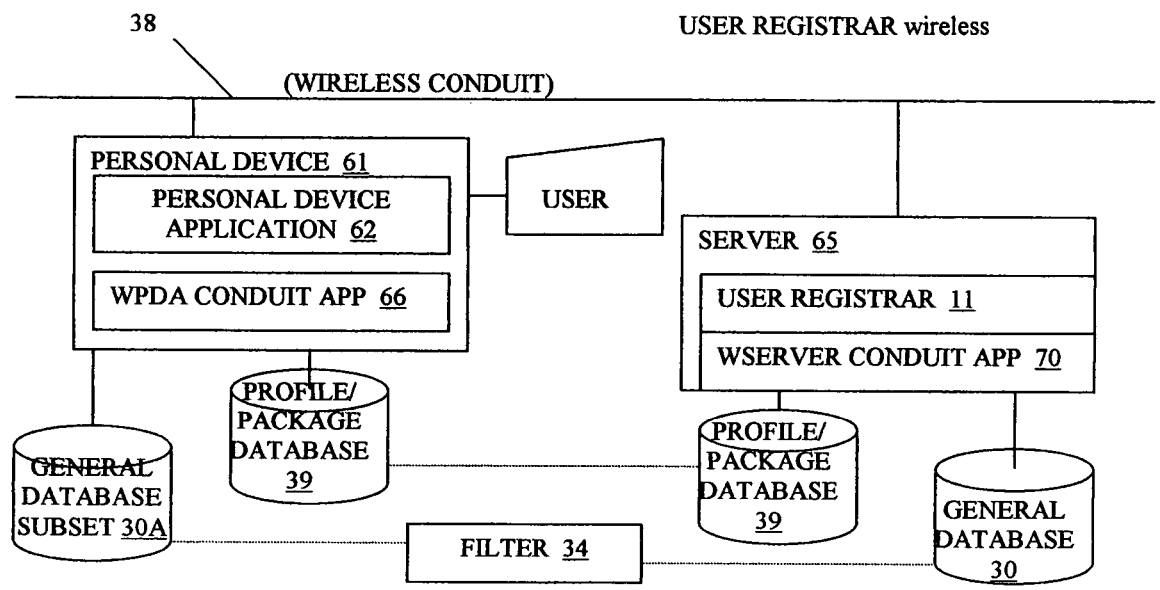
FIG. 4B is a schematic block diagram of the user registrar and wireless conduit for synchronization in a wireless environment of the illustrative embodiment of the present invention.

As shown schematically in FIGS. 4A-B, the system of the illustrative embodiment of the present invention can operate in at least two environments. The PC environment, shown in FIG. 4A, and the wireless environment, shown in FIG. 4B, both include personal device 61, possibly a PDA, a conventional cellular telephone, or any other such hand-held device, and server 65, and a connection between them that is referred to herein as conduit 37 (FIG. 4A), or alternatively, wireless conduit 38 (FIG. 4B), which are examples of the more general electronic interface 37A (FIG. 1A). Conduit 37/38 can allow synchronization of data between personal device 61 and server 65. When personal computer 63 (FIG. 4A) is used, conduit 37 can enable a set of hand-shaking applications executing on both personal computer 63 and server 65. When a wireless connection is used, wireless conduit 38 can enable a set of hand-shaking applications executing on personal device 61 and server 65. In either case, conduit 37 and wireless conduit 38 can manage data updates and route data bi-directionally between personal device 61 and server 65. In particular, if changes are made to general database 30 (FIG. 1A), profile/package database 39 (FIG. 1A), filter 34 (FIG. 1A), or other data, conduit 37/38 can enable the maintenance of database integrity across the system of personal devices 61 (FIG. 4A) and servers 65 (FIG. 4A).

Referring now to FIG. 4A, in the illustrative environment in which conduit 37 enables synchronization of data between personal computer 63 and server 65, conventional personal device synchronization software, such as, for example, HotSync application 64, provides data synchronization between personal computer 63 and personal device 61. In the illustrative embodiment, personal device 61 can be, for example, a standard PDA, such as a Palm OS device, with enough memory for applications code and data. Personal computer 63, in the illustrative embodiment, can execute an operating system and applications code that allow synchronization between personal device 61 and personal computer 63, with enough free disk space to enable synchronization, archiving, and storage of application files. In the illustrative embodiment, there is a means of communication, such as, for example, the internet, between personal computer 63 and server 65 (also herein referred to as the "web" or "website").

Referring now to FIGS. 4A and 4B, communication through conduit 37 FIG. 4A) or wireless conduit 38 (FIG. 4B) can be initially begun through installation of PC conduit application 67 (FIG. 4A), or through invocation of wPDA conduit application 64 (FIG. 4B) after personal device application 62 is installed, respectively. In the former case, after the installation completes, the user can start the synchronization process by, for example, clicking on the button on the cradle of the standard PDA. In the latter case, the user may click on a special icon that can be presented, for example, on the standard PDA by personal device application 62 to begin synchronization. In the former case, HotSync application 64 (FIG. 4A), previously launched on personal computer 63 (FIG. 4A), can receive the signal generated by personal device 61 (FIG. 4A) to start synchronization. PC conduit application 67 (FIG. 4A) can then establish a connection with server conduit application 68 (FIG. 4A). In the latter case, wPDA conduit application 64 (FIG. 4B) can start synchronization by establishing a connection with wserver conduit application 70 (FIG. 4A). Before synchronization can begin, however, data such as, for example, the user's identification, a password, the version number of the database that can hold the data and code being exchanged, and the unique identification of personal device 61 (FIG. 4A) are compared with corresponding information stored on server 65. If the data validate, synchronization can continue; otherwise synchronization is interrupted.

Referring now to FIGS. 4A, 4B, and 2B, PC conduit application 67, for example, can determine if personal device 61 (FIG. 4A) is using outdated software and/or data. If so, PC conduit application 67, for example, and possibly along with other system software, can invoke an automatic upgrade of the software and/or data to personal device 61. During synchronization, PC conduit application 67 (FIG. 4A) or wPDA conduit application 64 (FIG. 4B) can collect and transfer data that are ready for uploading (for example, if an appropriate attribute associated with the data is set) to server 65 from personal device 61 (FIG. 4A). During the data synchronization phase, conduit 37 (FIG. 2B) can enable transfer of data entered through personal device user tables 72 (FIG. 2B) such as, for example, a personal data file, the 7-day log, prescriptions, viewed tip groups, user comments, etc., from the personal device 61 to the web. System tables contain data common for all users, such as, for example, food items. Data specific to a particular user and that have been modified since the previous synchronization can be copied from server 65 (FIGS. 4A and 4B) to the personal device 61 (FIG. 4A) during synchronization. All data are subject to old and obsolete data removal on personal device 61. Obsolete data are, for example, data that have been deleted from server 65 and there is no reference to these data on personal device 61. Data on server 65 are generally not deleted but are archived instead. Some data are specific to server 65; these data are not usually transferred to the personal device 61. Memory of personal device 61 may be occasionally cleared (for example, because of hardware rest or power failure) and all data can be lost. In this case the user should be able to restore data from server 65. To allow this, server 65 can store a complete backup of personal device 61 data.

Continuing to refer to FIGS. 4A and 4B, and now providing a description of synchronization, either PC conduit application 67 (FIG. 4A) and server conduit application 68 (FIG. 4A), or wPDA conduit application 66 (FIG. 4B) and wserver conduit application 70 (FIG. 4B), can perform handshaking as follows. When initiated by PC conduit application 67 or wPDA conduit application 66 (sender), synchronization begins with getting connection information (such as, for example, database version, personal device identification, login, password, etc.) from an internal table and preparing that information for transfer to server conduit application 68 or wserver conduit application 70 (receiver). After the transfer occurs and the connection is established, database version identity is verified and, if both sender and receiver have the same version of the database, the sender prepares data from the database for transfer. In particular, data, from user tables, with correctly polarized attributes (for example, the "dirty" attribute set, the "server" attribute clear, and the "order" equal to "out"), can be transferred to the receiver if the records do not already exist on the receiver's system. In response to the sender's transmission, the receiver can send back one of several commands such as listed in the following table.

| Order | Meaning |
|---|---|
| ERR | Receiver encountered parsing error, for example |
| ACK | Receiver directs sender to mark transferred data as processed, for example, by clearing the "dirty" attribute |
| DEL | Receiver directs sender to delete obsolete data, for example, by (1) finding and fetching all references to obsolete data, (2) comparing fetched data with data identifications sent from sender, (3) if fetched data match data identifications sent from sender, delete data permanently and send notification to receiver, (4) if fetched data do not match data identifications sent from sender, log an error, (5) sender sends results of comparison to receiver |
| IN/INBIN | Receiver directs sender to add records to a sender's table, replace records in sender's table where records already exist |
| PROC | Sender sends a list of "processed" data identifications to receiver |

If records are changed on server 65 (by, for example, expert 14 (FIG. 1B), a professional (FIG. 1B), package designer 15 (FIG. 1A), etc.), server conduit application 68 or wserver conduit application 70 marks records as modified. When server conduit application 68 or wserver conduit application 70 transfer records, server conduit application 68 or wserver conduit application 70 marks the records as transferred. After the synchronization process is complete, PC conduit application 67 or wPDA conduit application 66 can delete obsolete records from personal device 61 (FIG. 4A). Note that, with this handshaking strategy, synchronization can be interrupted and restarted with no loss of integrity to the database.

Referring again to FIGS. 4A, 4B, and 2B, server tables 74 (FIG. 2B), server user tables 76 (FIG. 2B), user-specific program execution status, professional comments, etc., for example, can be transferred via conduit 37 (FIG. 4A) or wireless conduit 38 (FIG. 4B) to personal device 61 (FIGS. 4A/B). After this transfer is complete, PC conduit application 67 (FIG. 4A) or wPDA conduit application 64 (FIG. 4B) can remove unneeded data from personal device user tables 72 (FIG. 2B), such as, for example, old personal data, old 7-day logs, 14-day functionality answers and results, viewed tip groups and tips, etc. Data that become obsolete (i.e. records deleted on personal device 61 (FIGS. 4A/B), for example old fitness tests or PDF results) can be removed from personal device 61 during the synchronization just following the data's change in status to obsolete. After these data are removed from personal device 61, they can continue to be stored on server 65 (FIGS. 4A/B). In the illustrative embodiment, data, for example, such as logs of food and water consumption, fitness, behavior events, can be considered old or obsolete when a pre-determined number of weeks pass since they were last updated and when there is no longer a reference to the data. Personal device 61 (FIGS. 4A/B) can store certain data from the first time the user enters the system and also can store summary information calculated based on these records before they are removed from personal device 61. 14-day functionality results and scores can be moved from personal device 61 and stored on server 65 (FIGS. 4A/B) during the first successful synchronization after the completion of the 14-day functionality.

Referring again to FIGS. 4A and 4B, server conduit application 68 (FIG. 4A) or wserver conduit application 70 (FIG. 4B) can receive data destined for server 65 and can send data from server 65 to personal device 61. PC conduit application 67 (FIG. 4A) or wPDA conduit application 64 (FIG. 4B) can remove old data from personal device 61. After data transfer is completed, the conduit applications can close the connection. Server conduit application 68 (FIG. 4A) or wserver conduit application 70 (FIG. 4B) can track the age of data and can mark those data that meet preset criteria for deletion. Synchronization can be terminated after all data are exchanged, or, for example, after two send/receive cycles. Also, synchronization can be stopped for internal reasons such as, for example, internet connection loss. In the illustrative embodiment, there are two levels of synchronization: fast and slow. In fast synchronization, only new, modified and deleted data are involved. This is the normal type of synchronization. In slow synchronization, both modified and unchanged data are transferred from server 65 to personal device 61. This type of synchronization can be used to restore the user's data from a backup.

Continuing to refer to FIGS. 4A-B, conduit 37 (FIG. 4A) or wireless conduit 38 (FIG. 4B) enables transfer of such illustrative data as follow:

| SQL Server Table Name | Synchronization Direction |
|---|---|
| Activity | Server |
| Alcohol | Server 65 to personal device 61 |
| Anim | Server 65 to personal device 61 |
| APlan | Server 65 to personal device 61 |
| BhvContra | Server 65 to personal device 61 |
| ComBrand | Server 65 to personal device 61 |
| ComClass | Server 65 to personal device 61 |
| ComGroup | Server 65 to personal device 61 |
| ComItem | Server 65 to personal device 61 |
| Company | Server 65 to personal device 61 |
| ComSubgroup | Server 65 to personal device 61 |
| Constants | Server 65 to personal device 61 |
| Cuisine | Server 65 to personal device 61 |
| CuisineItem | Server 65 to personal device 61 |
| CuisineSection | Server 65 to personal device 61 |
| Duration | Server 65 to personal device 61 |
| ETest | Server 65 to personal device 61 |
| ETestQuestion | Server 65 to personal device 61 |
| FitBaseTest | Server 65 to personal device 61 |
| FitCalories | Server 65 to personal device 61 |
| FitEquipment | Server 65 to personal device 61 |
| FitEx | Server 65 to personal device 61 |
| FitExIntens | Server 65 to personal device 61 |
| FitExLink | Server 65 to personal device 61 |
| FitExMuscle | Server 65 to personal device 61 |
| FitMuscle | Server 65 to personal device 61 |
| FitMuscleThreads | Server 65 to personal device 61 |
| FitRecommend | Server 65 to personal device 61 |
| FoodGroup | Server 65 to personal device 61 |
| FoodItem | Server 65 to personal device 61 |
| FTTDescr | Server 65 to personal device 61 |
| FTTResult | Server 65 to personal device 61 |
| FTTResultDescr | Server 65 to personal device 61 |
| FTTStep | Server 65 to personal device 61 |
| FTTType | Server 65 to personal device 61 |
| FullnessLevel | Server 65 to personal device 61 |
| Goal | Server 65 to personal device 61 |
| Hunger | Server 65 to personal device 61 |
| Location | Server 65 to personal device 61 |
| MealType | Server 65 to personal device 61 |
| Measurement | Server 65 to personal device 61 |
| Menu | Server 65 to personal device 61 |
| MenuCalories | Server 65 to personal device 61 |
| MenuDailyCalories | Server 65 to personal device 61 |
| MenuItem | Server 65 to personal device 61 |
| Mood | Server 65 to personal device 61 |
| MoodGroup | Server 65 to personal device 61 |
| NutContra | Server 65 to personal device 61 |
| Nutrient | Server 65 to personal device 61 |
| NutrientFood | Server 65 to personal device 61 |
| NutrientMeasureUnit | Server 65 to personal device 61 |
| PDFAllergy | Server 65 to personal device 61 |
| PDFInputRange | Server 65 to personal device 61 |
| PDFMedCond | Server 65 to personal device 61 |
| PDFRange | Server 65 to personal device 61 |

-continued

| SQL Server Table Name | Synchronization Direction |
| --- | --- |
| PortionType | Server 65 to personal device 61 |
| Position | Server 65 to personal device 61 |
| Preparation | Server 65 to personal device 61 |
| PrepContra | Server 65 to personal device 61 |
| Reminder | Server 65 to personal device 61 |
| Sauce | Server 65 to personal device 61 |
| SauceGroup | Server 65 to personal device 61 |
| Self | Server 65 to personal device 61 |
| ServObject | Server 65 to personal device 61 |
| Splash | Server 65 to personal device 61 |
| ThoughtCat | Server 65 to personal device 61 |
| ThoughtTip | Server 65 to personal device 61 |
| Tip | Server 65 to personal device 61 |
| TipGroup | Server 65 to personal device 61 |
| Units | Server 65 to personal device 61 |
| UserAlarm | Personal device 61 to Server 65 |
| UserBalanceLog | Personal device 61 to Server 65 |
| UserBehavior | Personal device 61 to Server 65 |
| UserComment | Personal device 61 to Server 65 |
| UserCreatedMealItem | Personal device 61 to Server 65 |
| UserDayLogPresent | Personal device 61 to Server 65 |
| UserETest | Personal device 61 to Server 65 |
| UserETestAnswer | Personal device 61 to Server 65 |
| UserETestReward | Personal device 61 to Server 65 |
| UserETestScore | Personal device 61 to Server 65 |
| UserEvent | Personal device 61 to Server 65 |
| UserFavorite | Personal device 61 to Server 65 |
| UserFitExLog | Personal device 61 to Server 65 |
| UserFitExLogEx | Personal device 61 to Server 65 |
| UserFitPack | Both directions |
| UserFitPackEx | Both directions |
| UserFTTResults | Personal device 61 to Server 65 |
| UserGoal | Both directions |
| UserInetSettings | Personal device 61 to Server 65 |
| UserMealItem | Personal device 61 to Server 65 |
| UserMealJournal | Personal device 61 to Server 65 |
| UserMessage | Personal device 61 to Server 65 |
| UserNutRecommended | Personal device 61 to Server 65 |
| UserNutrient | Personal device 61 to Server 65 |
| UserPARQ | Personal device 61 to Server 65 |
| UserPDFAllergy | Personal device 61 to Server 65 |
| UserPDFConst | Personal device 61 to Server 65 |
| UserPDFFilled | Personal device 61 to Server 65 |
| UserPDFMeasure | Personal device 61 to Server 65 |
| UserPDFMedCond | Personal device 61 to Server 65 |
| UserPDFMisc | Personal device 61 to Server 65 |
| UserPDFResultPresent | Personal device 61 to Server 65 |
| UserPDFTest | Personal device 61 to Server 65 |
| UserPDFTestResults | Personal device 61 to Server 65 |
| UserPDFWomen | Personal device 61 to Server 65 |
| UserPlan | Personal device 61 to Server 65 |
| UserPyramidPresent | Personal device 61 to Server 65 |
| UserRX | Personal device 61 to Server 65 |
| UserRXLog | Personal device 61 to Server 65 |
| UserSettings | Personal device 61 to Server 65 |
| UserSleep | Personal device 61 to Server 65 |
| UserStress | Personal device 61 to Server 65 |
| UserTblMaxId | Personal device 61 to Server 65 |
| UserTipJournal | Personal device 61 to Server 65 |
| UserTipSettings | Personal device 61 to Server 65 |
| UserTipTask | Personal device 61 to Server 65 |
| UserVersion | Personal device 61 to Server 65 |
| UserWater | Personal device 61 to Server 65 |
| UserWeekLogPresent | Personal device 61 to Server 65 |

These data are presented for illustrative purposes only and do not limit the type or naming of data that are transferred between personal device 61 and server 65. These data can be part of general database 30, profile/package database 39, or another database. Filter 34 can be used to select parts of general database 30 that are applicable to a particular user, and prepare general database subset 30A.

Figure 4C:
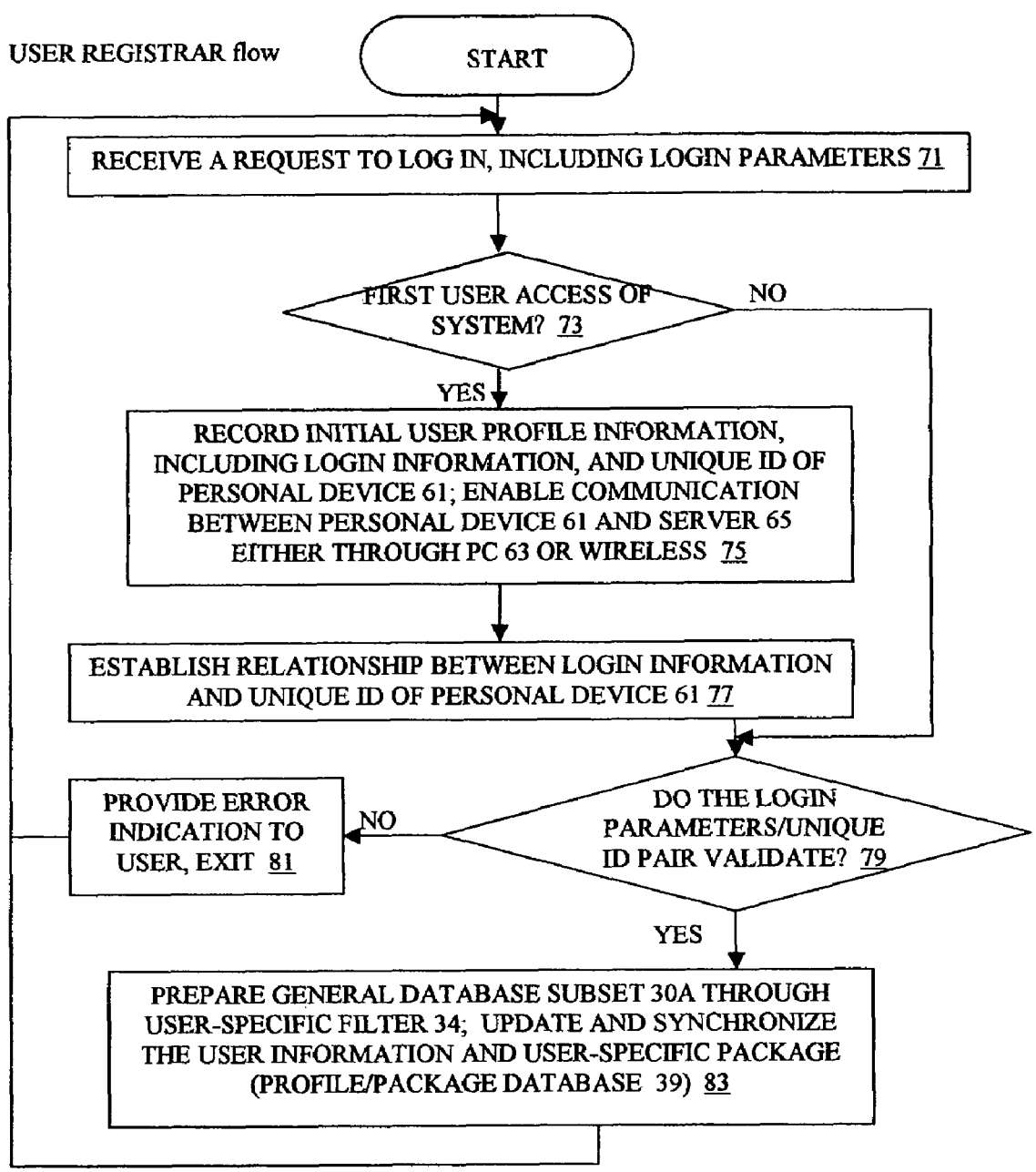
FIG. 4C is a flowchart of the user registrar, including synchronization, in either a personal computer or a wireless environment of the illustrative embodiment of the present invention.

Referring now primarily to FIG. 4C, the method of the user registrar 11 (FIG. 4A) and synchronization of the illustrative embodiment of the present invention, in an environment that either contains personal computer 63 (FIG. 4A) or provides a wireless connection between the personal device 61 (FIGS. 4A/B) and the server 65 (FIGS. 4A/B), includes, but is not limited to, the following steps including the step of receiving a request to log in to the system, including login parameters (method step 71). If this is the first time the user has accessed the system (decision step 73), the method can include the step of recording initial user profile information, including login information, and enabling communication between server 65 and personal device 61 either through personal computer 63 or wirelessly (method step 75). If this user access is not the initial access (decision step 73), the method can include the step of continuing execution at decision step 79 described below. The method may further include the step of establishing a relationship between the login information and a unique identifier of personal device 61 (method step 77). The unique identifier and the login information cam be associated with each other so that both are required before a user is allowed access to the system. Thus, even if a user is recognized by the system, the user is not able to use the personal device of another user because the login and unique identifier would not simultaneously validate. If the provided login information and the unique identifier of personal device 61 do not validate (decision step 79), the method can further include the steps of returning an error to the user and returning to method step 71 (method step 81). If the provided login information and the unique identifier of personal device 61 validate (decision step 79), the method can further include the step of preparing general database subset 30A through the user of filter 34, and updating and synchronizing the user information, including a user-specific package 1151 (FIGS. 13A/C) (method step 83). After personal device 61 is known to the system and personal device application 62 (FIGS. 4A/B) is executing on personal device 61, the user may enter data on personal device 61. These data are provided to server 65 during the synchronization process, and server 65 analyzes these data. During the analysis process, data from profile/package database 39 (FIG. 1A) can be subject to modifications by, for example, the user, expert 14 (FIG. 1B), or a professional (FIG. 1B). These modified data are returned to personal device 61 during the synchronization process.

Figure 5A:
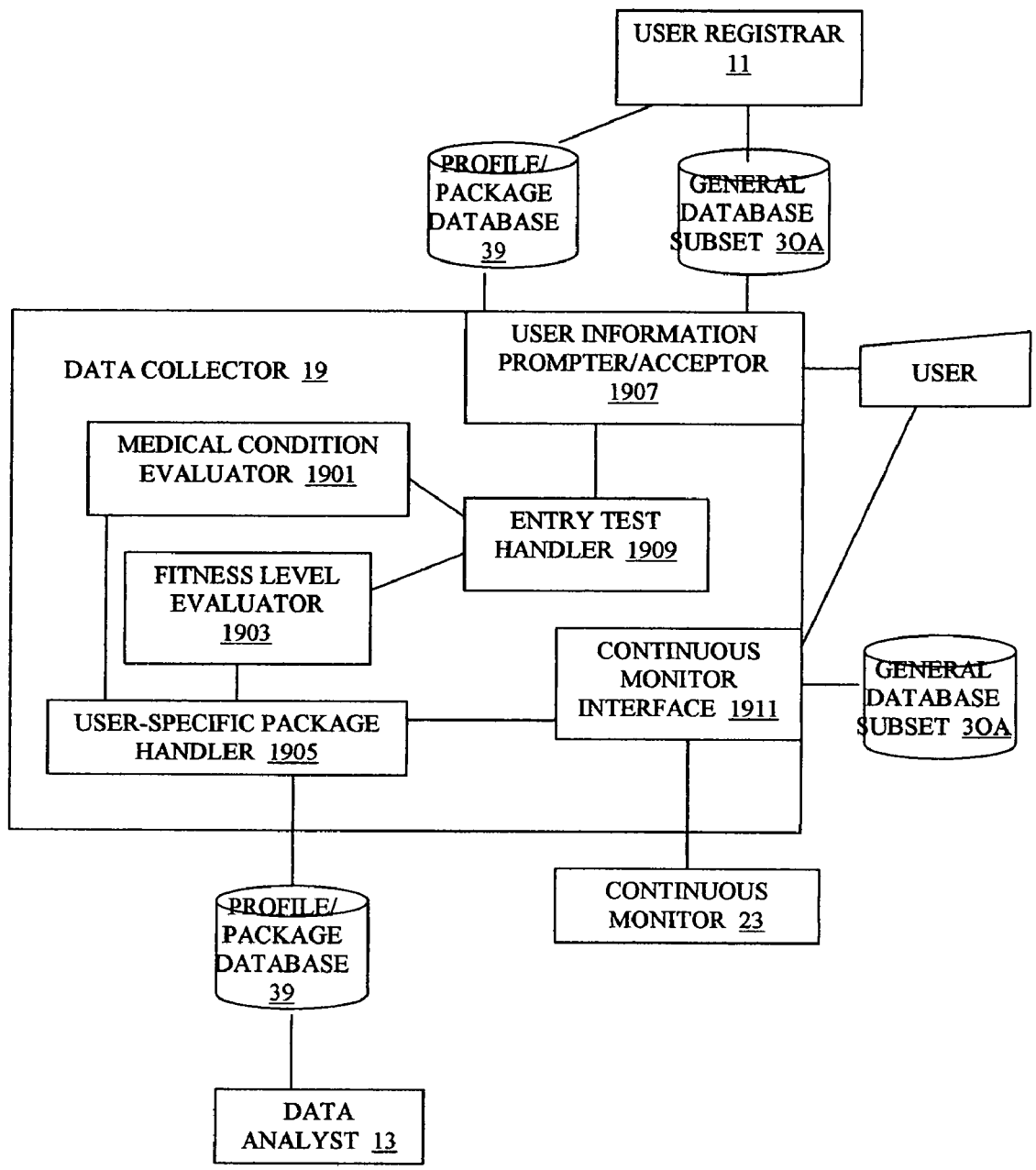
FIG. 5A is a schematic block diagram of the data collector of the illustrative embodiment of the present invention.

Referring now to FIG. 5A, data collector 19 of the illustrative embodiment of the present invention includes, but is not limited to, user information prompter/acceptor 1907, medical condition evaluator 1901, entry test handler 1909, fitness level evaluator 1903, continuous monitor interface 1911, and user-specific package handler 1905. User information prompter/acceptor 1907 receives information from the user and/or from continuous monitor 23 through continuous monitor interface 1911, and provides that information to medical condition evaluator 1901 and fitness level evaluator 1903, which can provide results to user-specific package handler 1905. During certain time periods, entry test handler 1909 can receive entry test data from the user and supplies that information, as appropriate, to medical condition evaluator 1901, fitness level evaluator 1903, and user-specific package handler 1905. Data collector 19 relies on data from, for example, but not limited to, profile/package database 39 and general database subset 30A to prompt the user and analyze user input, while at the same time data collector 19 provides creation, modification, and update to data that are part of, for example, profile/package database 39. In the illustrative embodiment, data collector 19 can be embodied in a handheld device such as a PDA which provides the user with an easily-mastered interface, even a game-like interface, that encourages use of the device. Initially, during a first time period, such as, for example, 14 days, the user is prompted for general information by data collector 19. Data collector 19 records this information into, for example, profile/package database 39. After synchronization, control is transferred to data analyst 13, and data that are collected and partially analyzed by data collector 19 are analyzed by data analyst 13. A synchronization could take place before, during, or after data collector 19 transfers control to data analyst 13. Data collector 19 continually allows the user to enter information.

Figure 5B:
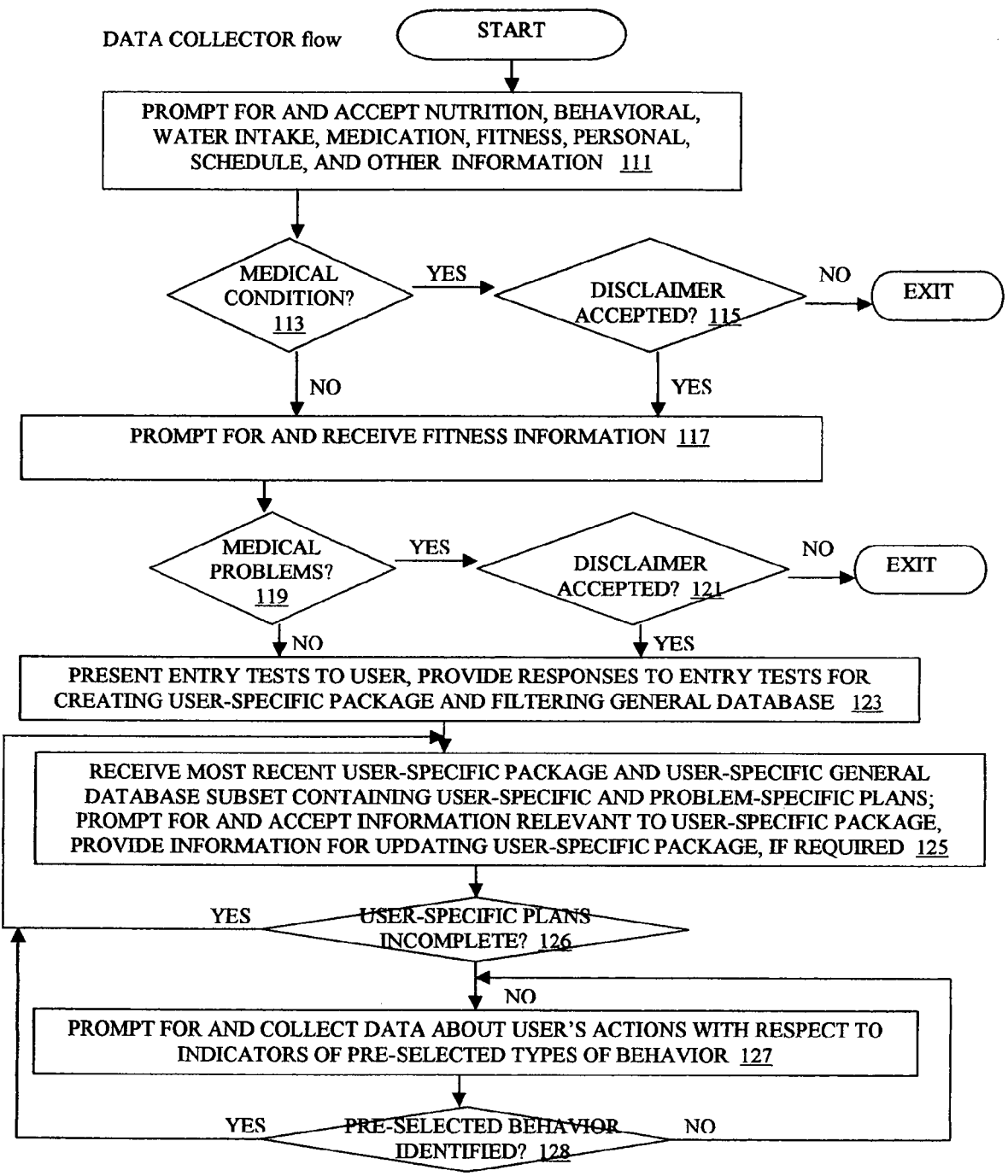
FIG. 5B is a flowchart of the data collector of the illustrative embodiment of the present invention.

Referring to FIG. 5B, the method of the illustrative embodiment of the data collector 19 (FIG. 5A) is shown. The method can include, but is not limited to, the steps of prompting for and accepting the user's nutrition, behavior, water intake, personal, and other information (method step 111). If the user's condition is deemed by the system to require a medical professional's release (decision step 113), for example, if the user's blood pressure is above 140/90, and if the user does not sign a disclaimer (decision step 115), the user may not be allowed to continue using the system. If the user does not exhibit a condition that could require a medical professional's release (decision step 113), or if the user signs a disclaimer (decision step 115), the method can further include the steps of prompting for and receiving fitness information (method step 117). If the results of the fitness tests indicate that the user's condition requires a medical professional's release (decision step 119) and if the user does not sign a disclaimer (decision step 121), the user may not be allowed to continue using the system. If the user's condition does not require a medical professional's release (decision step 119), or if the user signs a disclaimer (decision step 121), the method can further include the steps of prompting for and accepting responses to entry tests (FIG. 14B), such as, for example, ParQ tests, and providing entry test responses to data analyst 13 for preparing the user-specific package 1151 (FIGS. 13A/C) (method step 123). The method can further include the step receiving the most recent user-specific package 1151 (FIGS. 13A/C) and user-specific general database subset 30A (FIG. 5A) containing at least one user-specific program, and prompting for and accepting information relevant to the user-specific package 1151 (FIGS. 13A/C), and providing information for updating the user-specific package 1151 (FIGS. 13A/C), if any (method step 125). If any user-specific plans are incomplete (decision step 126), the method can further include the step of repeating method step 125 and decision step 126. If no user-specific plans are incomplete (decision step 126), the method can further include the step of prompting for and accepting data about the user's actions with respect to indicators of pre-selected types of behavior (method step 127). If a pre-selected behavior is identified (decision step 128), the method can further include repeating method loop 125-127. If a possible behavior is not identified (decision step 128), the method can further include repeating method loop 127-128.

Operationally, and referring again to FIG. 5A, each time the user invokes the system, data collector 19 determines if a medical condition is present and has not been cleared. The user may not be allowed to proceed unless the condition is cleared. After initial personal data are collected, data collector 19 computes such parameters as body mass index (BMI) and basal metabolic rate (BMR), along with a range of heart rates within which the user should attempt to remain, and a healthy physical exercise range for the user. Feedback provider 17 can present the user with a healthy weight range for the user, a weight loss recommendation, and the number of calories required to maintain or achieve the desired weight. If the user's blood pressure or cholesterol are outside a healthy range, the user is considered to have a medical condition and will require clearance to continue using the system. Although the present invention is not limited thereto, two examples of the computations previously described follow:

Example 1

40-year-old male

Present weight: 205 pounds, 93 kg

Height: 6'0", 183 cm

BMI: 28 (overweight)

Activity level—light: Performs cardiovascular activity 30 minutes/session 2 days/week.
1. Resting Metabolic Rate—1 kcal/kg/hr×93 kg×24 hours/day=2232 calories
2. Activity level—670 calories
3. User needs 2902 kcal/day to maintain current weight.
Client must decrease caloric intake, or increase caloric output by:

| 250/day | to lose: | _pound/week |
|---|---|---|
| 500/day | to lose: | 1 pound/week |
| 750/day | to lose: | 1.5 pound/week |
| 1000/day | to lose: | 2 pounds/week |

An appropriate combination of decreasing caloric intake and increasing caloric output might look like this:
Daily caloric intake: 2150 calories (reduction of 750 calories)
Physical Activity Add 3 more days of 30 minutes cardiovascular activity+2 days of 30 minutes of strength training=approximately 250 additional calories expended per day.
Total=2900−1000=1900; should result in client losing approximately 2 pounds/week.

Example 2

34 year old female

Present weight: 278 pounds, 126 kg

Height: 5'6", 168 cm

BMI=>40 (obese)

Activity level—sedentary-light: walked 30 minutes 1 day/week, performs 1 day strength training 1 day/week.
1. Resting Metabolic Rate—0.9 kcal/kg/hr×126 kg×24 hrs/day=2721 calories
2. Activity level—816 calories
3. User needs 3537 kcal/day to maintain current weight.
However, when the user is obese, extra computations are required to compute an adjusted body weight and an adjusted number of calories need to maintain current weight, which in this case is 2249 kcal/day.
Client must decrease caloric intake, or increase caloric output by:

| 250/day | to lose: | _pound/week |
|---|---|---|
| 500/day | to lose: | 1 pound/week |
| 750/day | to lose: | 1.5 pound/week |
| 1000/day | to lose: | 2 pounds/week |

An appropriate combination of decreasing caloric intake and increasing caloric output might look like this:
Daily caloric intake: 1750 calories (reduction of 500 calories)
Physical Activity Add 2 more days of 30 minutes cardiovascular activity+2 days of 30 minutes of strength training=approximately 250 additional calories expended per day.
Total=2250−750=1750; should result in client losing approximately 1.5 pounds/week.

Continuing to refer to FIG. 5A, data collector 19 prompts the user periodically, for example once/month, for weight and activity level information. Data collector 19 can require, for example, that each medication have a name; other parameters, for example, such as, dose, take with food, take with water, intake schedule, and affect of exercise could be entered as well. Data collector 19 can inform feedback provider 17 (FIG. 5A) to display a reminder to the user when medication is due. Data collector 19 allows the user to delete and add medications and record intake. Examples of data exchange enabled by data collector 19 appear in FIGS. 14A-O described herein. During data collection, data collector 19 can display, for example, a series of questions and answers on a set of screens (see FIGS. 14A-O). Each screen in the series can contain a specific type of question. Possible answers can be represented with radio-button controls, and users may answer the questions or skip the questions. Data analyst 13 (FIG. 5A) can process the answers to these questions at the end of the initial time period and can calculate (from the 7-day log, see FIGS. 14N/O)) a weekly or daily average of daily snacks, a weekly average interval between major meals, etc. Using the answers to the initial questions, the analysis of the user presented by the questions can be compared to a set of rules. Each set of rules can be built to identify certain types of behavior (for example external eating, emotional eating, etc.). Each rule can define conditions to be checked and refers to an action plan that is recommended if the condition is true. Rules can be created and modified by expert 14 (FIG. 1B) and professional (FIG. 1B). Examples of information that data collector 19 is prepared to accept from the user in the illustrative embodiment can include, for example, the following: initial information gathered over a pre-selected time period such as 14 days (FIG. 14A), medical information (FIG. 14B), entry tests (FIG. 14C), nutrition, such as favorite foods (FIGS. 14D/E), fitness, such as exercise schedule and favorite exercises (FIGS. 14F-H), behavior (FIG. 14I), schedule (FIGS. 14J/K), liquid intake (FIG. 14L), tips and information (FIG. 14M), and 7-day-log(FIGS. 14N/O).

Figure 6A:
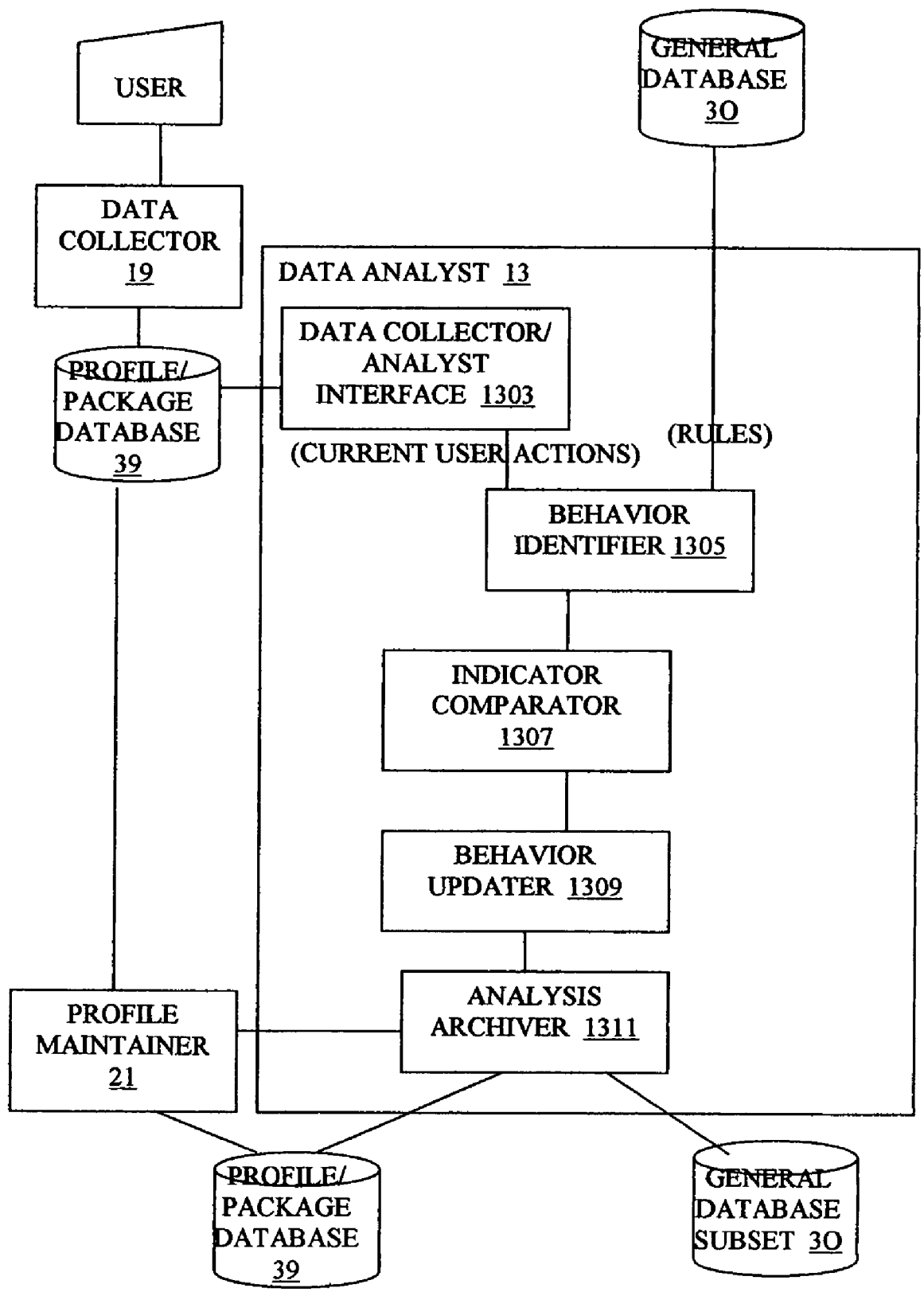
FIG. 6A is a schematic block diagram of the data analyst of the illustrative embodiment of the present invention.

Referring now to FIG. 6A, in the illustrative embodiment of the present invention, data analyst 13 includes, but is not limited to, package designer interface 1301, data collector/analyst interface 1303, behavior identifier 1305, indicator comparator 1307, behavior updater 1309, and analyst archiver 1311. Behavior identifier 1305 can access rules from general database 30 and current user activities from data collector/analyst interface 1303, and can analyze the activities with respect to the rules to identify possible types of behavior if any, that are indicated by the user's actions. Indicator comparator 1307 can determine if the current user activities indicate that the user is identified with one or more types of behavior. Behavior updater 1309 can modify the user's set of identifies behaviors, if any modifications are necessary, and associated data. Analysis archiver 1311 can track and record the user's history of identified behaviors and activities.

Figure 6B:
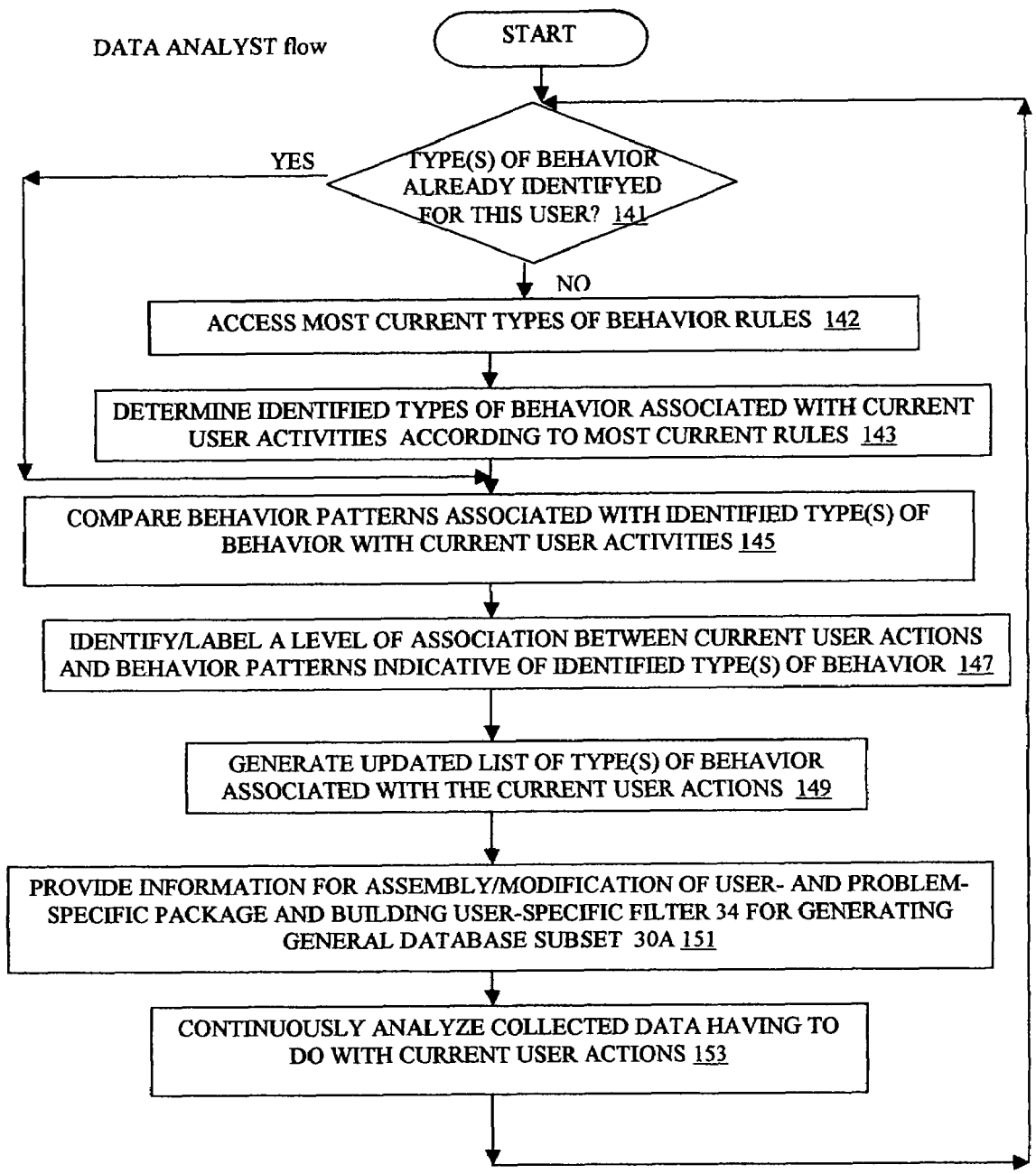
FIG. 6B is a flowchart of the data analyst of the illustrative embodiment of the present invention.

Referring now to FIG. 6B, the method of the illustrative embodiment of data analyst 13 (FIG. 6A) is shown. If a type(s) of behavior is not already identified for the user (decision step 141), the method can include, but is not limited to, the following steps, including the step of accessing the most current rules concerning possible types of behavior that the system can recognize (method step 142). The method can further include the step of determining identified type(s) of behavior, if any, associated with the current user activities according to the most current rules (method step 143). If a type(s) of behavior has already been identified (decision step 141), or after a type of a type(s) of behavior has been identified (method step 143), the method can include the step of comparing behavior pattern(s) associated with the identified type(s) of behavior with the current user current activities (method step 145). The method can further include the step of identifying and labeling a level of association between the current user activities and behavior patterns indicative of the identified type(s) of behavior (method step 147). The method can further include the steps of generating an updated list of type(s) of behavior associated with the current user activities (method step 149) and providing information for assembly/modification of user- and problem-specific packages and building user-specific filter 34 (FIG. 6A) for generating general database subset 30A (FIG. 6A) (method step 151). The method can further include the step of continuously analyzing collected data having to do with user current activities, and repeating method steps 141-153.

Figure 7A:
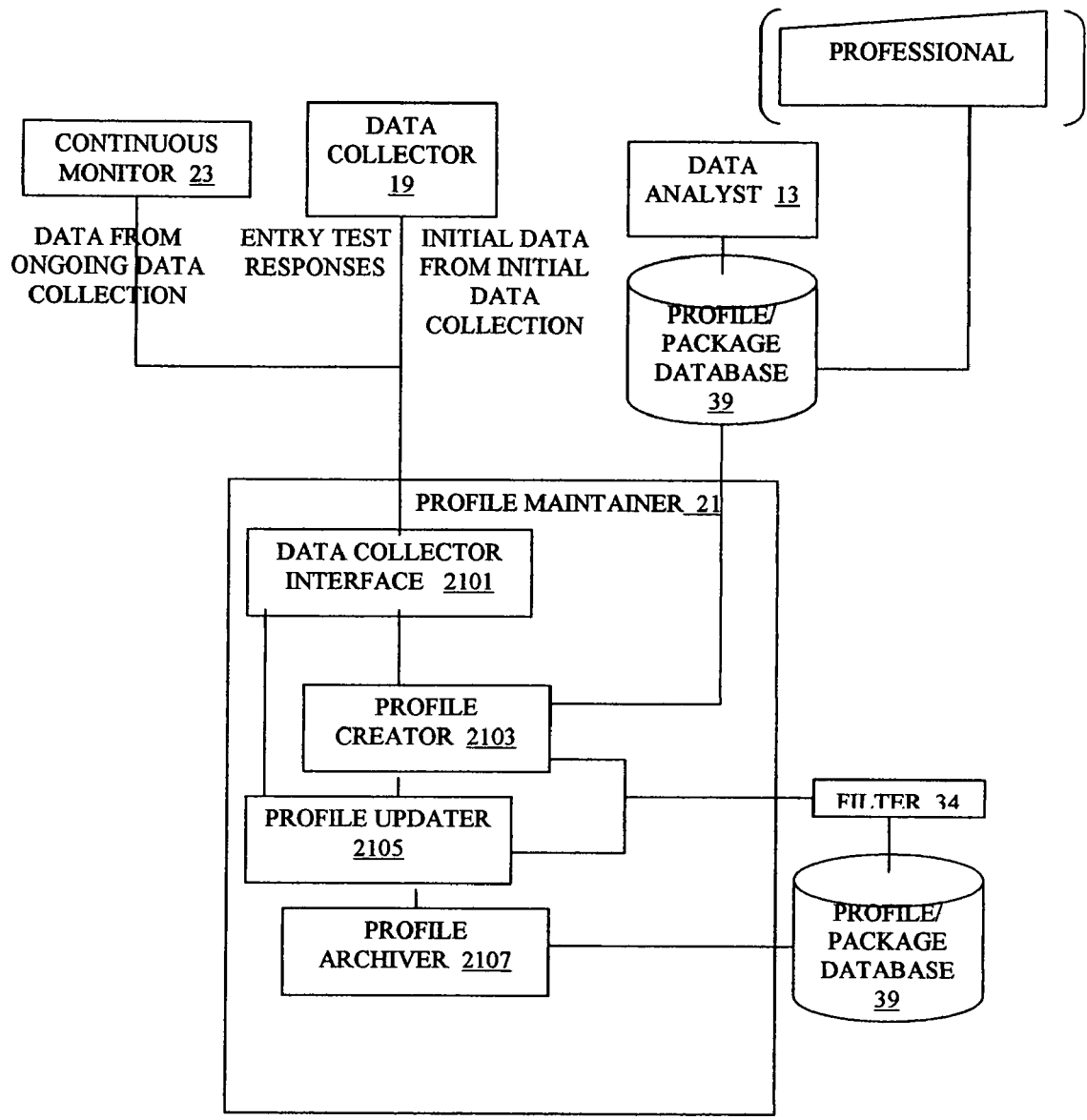
FIG. 7A is a schematic block diagram of the profile maintainer of the illustrative embodiment of the present invention.

Referring now to FIG. 7A, profile maintainer 21 of the illustrative embodiment of the present invention includes, but is not limited to, data collector interface 2101, profile creator 2103, profile updater 2105, and profile archiver 2107. As the user supplies information to data collector 19 and continuous monitor 23, data collector interface 2101 decides which data form the user's profile. Profile creator 2103 can create a profile and creates and/or updates filter 34 for a user and populates it with data supplied by data collector interface 2101 and data analyst 13 through profile/package database 39. Profile updater 2105 can update the user's profile and the filter 34 as data are continually collected. Periodically profile archiver 2107 can save the user's profile to profile/package database 39.

Figure 7B:
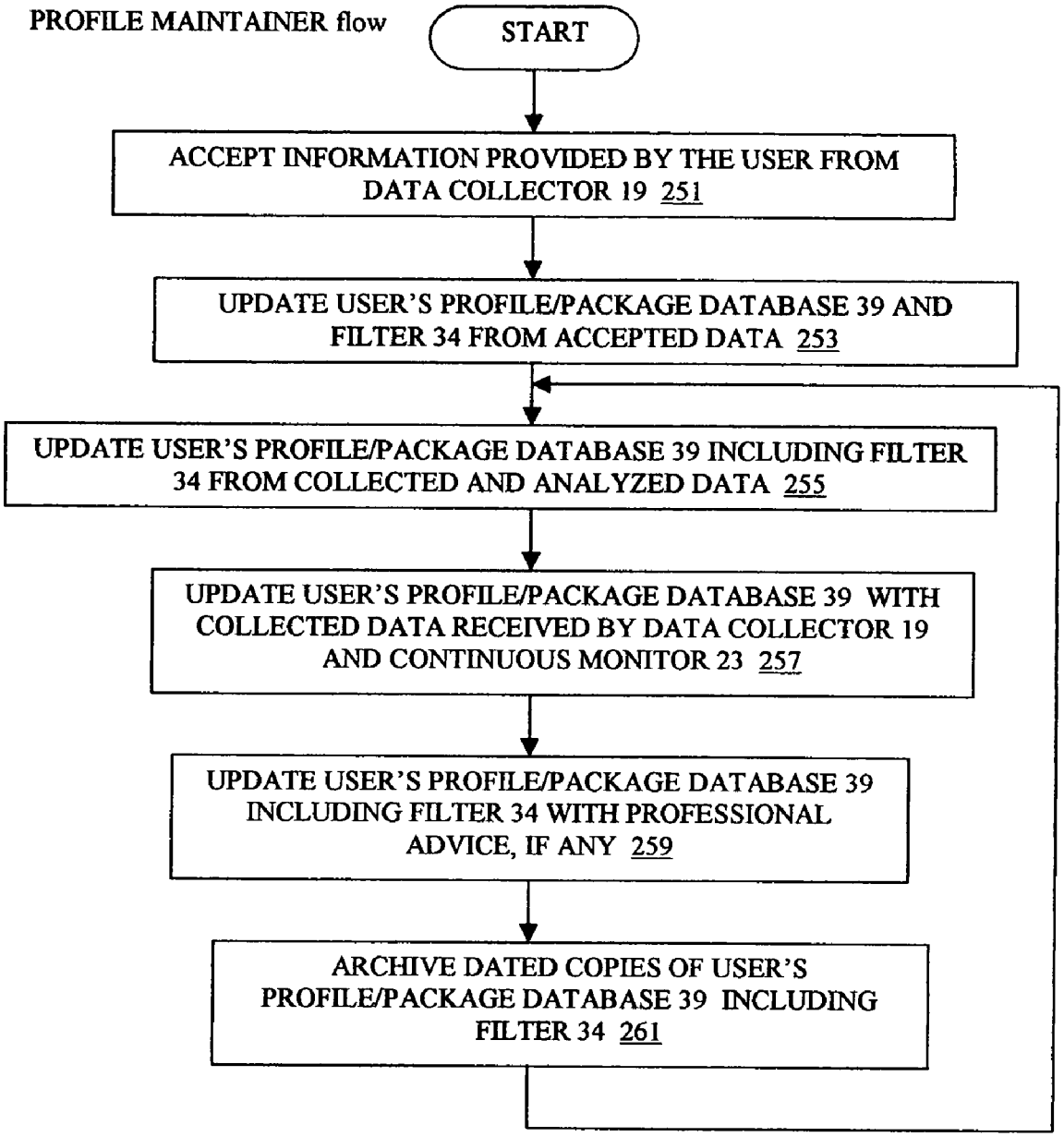
FIG. 7B is a flowchart of the profile maintainer of the illustrative embodiment of the present invention.

Referring now to FIG. 7B, the method of profile maintainer 21 (FIG. 7A) of the illustrative embodiment of the present invention can include, but is not limited to, the steps of accepting information provided by the user from data collector 19 (FIG. 7A) (method step 251). The method can further include the step of using the accepted data to update and/or create, if necessary, the user's profile (method step 253). The method can further include a loop having the steps of updating profile/package database 39 (FIG. 7A) with collected data received by data collector 19 and continuous monitor 23 (FIG. 7A) through profile/package database 39 and analyzed data received through profile/package database 39 (method step 255), and updating the user's profile with continuously collected and analyzed data (method step 257). The loop can further include the steps of updating the profile/package database 39 (FIG. 7A) and filter 34 (FIG. 7A) based on professional advice, if any (method step 259), and archiving the user's profile (method step 261).

Figure 8A:
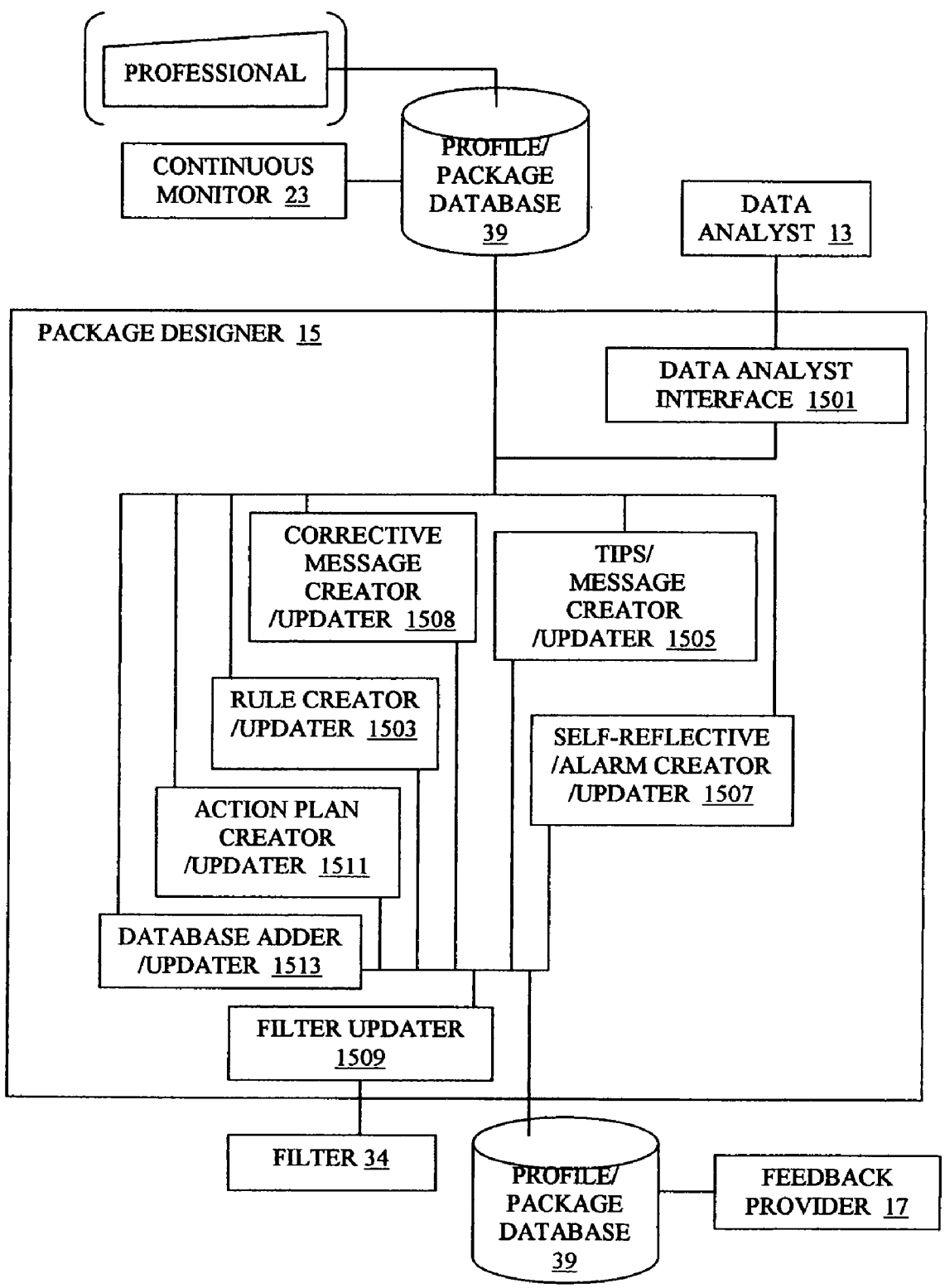
FIG. 8A is a schematic block diagram of the package designer of the illustrative embodiment of the present invention.

Referring now to FIG. 8A, package designer 15 includes, but is not limited to, data analyst interface 1501, corrective message creator/updater 1508, tips/message creator/updater 1505, rule creator/updater 1503, self-reflective/alarm creator/updater 1507, action plan creator/updater 1511, database adder/updater 1513, and filter creator/updater 1509. Package designer 15 can access analyzed and continuously collected data (from data analyst 13 through data analyst interface 1501, and from continuous monitor 23 and optionally a professional(s) through profile/package database 39) to create and dynamically update a user-specific package 1151 (FIGS. 13A/C) of information such as, for example, user-specific programs including, for example, action plans, tips, messages, self-reflective information, rules, corrective thoughts/beliefs/feelings, and other information. Examples of corrective thoughts/beliefs/feelings are presented below, not for the purpose of limiting the present invention, but for the purpose of more clearly illustrating aspects of the invention.

but isn't limited to, a loop following the steps of accessing dynamically changing user-specific data, including, for example, stress data, and accessing dynamically changing analyzed data that provide, for this user, for this particular time, identified type(s) of behavior, if any, and the level(s) of association of, for example, the user's activities, moods, feelings, stress, etc., with the type of behavior (these data are derived through on-going, possibly real-time, analysis of behavior patterns, previously described), and professional

|  | 1 | CORRECTIVE | 2 | CORRECTIVE | 3 | CORRECTIVE |
|---|---|---|---|---|---|---|
|  |  | THOUGHT |  |  |  |  |
| Control | "I need a new diet to get this weight off." | "I'm going to start working from the inside out and try to figure out why I am overeating." | "I'm too busy during the day to pay attention to what I eat." | "Being mindful during meals is just a habit and I can develop it." | "I've got to eat these cookies or I'll fall apart." | "I'm developing the inner strength to deal with this. Cookies won't help." |
|  |  | FEELING |  |  |  |  |
| Frustration | "I am totally out of control with food and I hate my body." | "I'm going to take three deep breaths and figure out what is bothering me." | "I can't stop over-eating!" | "Stuffing myself with excess food that I don't even taste or enjoy won't make my problem go away." | "I am so frustrated. No one is listening to me. Where's that__ gallon of ice cream?" | "I can handle this situation. I'm going to write down my views and talk to him about it." |
|  |  | BELIEF |  |  |  |  |
| Large Body | "I would never be seen eating cake in public!" | "My goal is to eat based on my internal cues and to include fun and enjoyable foods regularly to avoid bringing on them later in private." | "I'm powerful (because of my large size)." | "Power comes from inside myself. I can be powerful at any size." | "Why bother trying to eat better? I haven't lost anything this week." | "I've made a decision to eat mindfully and make the best choices I can and to move my body because it feels great, regardless of what happens to my weight." |

In the above table, an exemplary list of categories of thoughts is shown. Each category, for example, "control", can contain an unlimited number of thoughts that the user might have with respect to that particular aspect of a problem. Each time the system identifies that the user is possibly or definitely thinking a certain thought, the system provides to the user a "corrective" thought as shown in alternating columns above. In this way, the system helps the user to replace, for example, persistent and detrimental thought patterns with more useful and productive thought patterns. Data sets of required information can be added and accessed as needed, facilitated by database adder/updater 1513. After package designer 15 has updated and/or created a user-specific package 1151 (FIGS. 13A/C) (including for example profile/package database 39 and filter 34 (created with filter creator/updater 1509)), package designer 15 can update the profile/package database 39 which can be accessed by any number of modules, including feedback provider 17, to present updated action plans, etc., to the user.

Figure 8B:
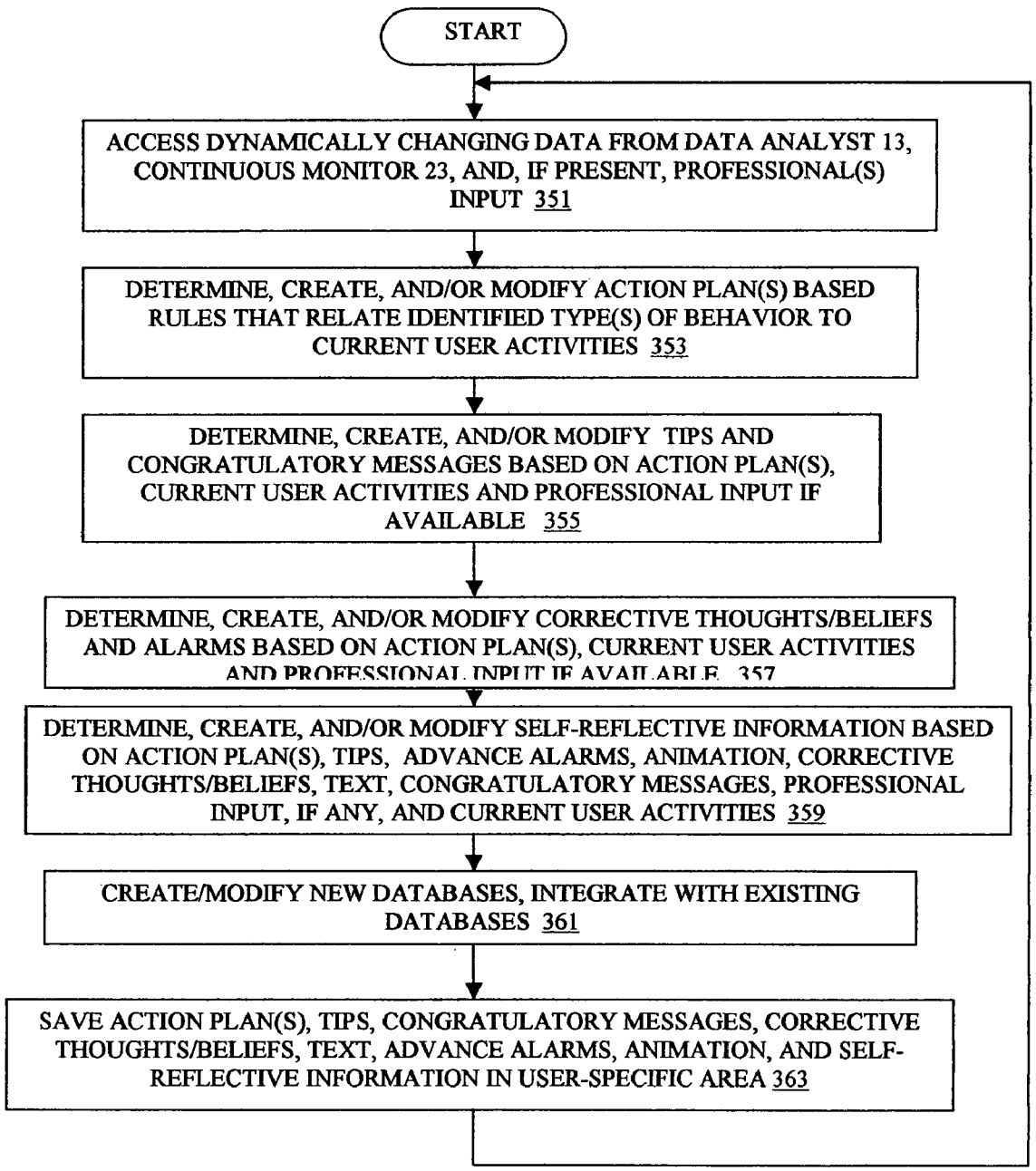
FIG. 8B is a flowchart of the package designer of the illustrative embodiment of the present invention.

Referring now to FIG. 8B, the method of the illustrative embodiment of package designer 15 (FIG. 8A) can include, input, if any (method step 351). The loop can further include the step of determining action plan(s), if any, based on the identified type(s) of behavior, if any, and level(s) of association, if any (method step 353). The loop can further include the steps of determining tips and congratulatory messages that are associated with the identified action plan(s), if any, and modifying such data as, for example, user-specific programs including, for example, action plans, tips, and congratulatory messages based on, for example, professional input, if any (method step 355). The loop can further include the step of determining corrective thoughts and beliefs based on, for example, the current thoughts and beliefs of the user (method step 357). The loop can further include the step of determining self-reflective information based on, for example, action plan(s), if any, stress, tips, advance alarms, animation, text, corrective thoughts/beliefs/feelings, congratulatory messages, and professional input, if any, and user-specific information (method step 359). The loop can further include the step of creating and/or modifying new data sets, as needed, and integrating them with existing data sets (method step 361). The loop can further include the steps of saving data, for example, action plan(s), if any, tips, corrective thoughts/beliefs/feelings, advance alarms, text, congratulatory messages, professional advice, if any, animation, self-reflective information, etc., in a user-specific area (method step 363) and returning to begin the loop again at method step 351.

Figure 8C:
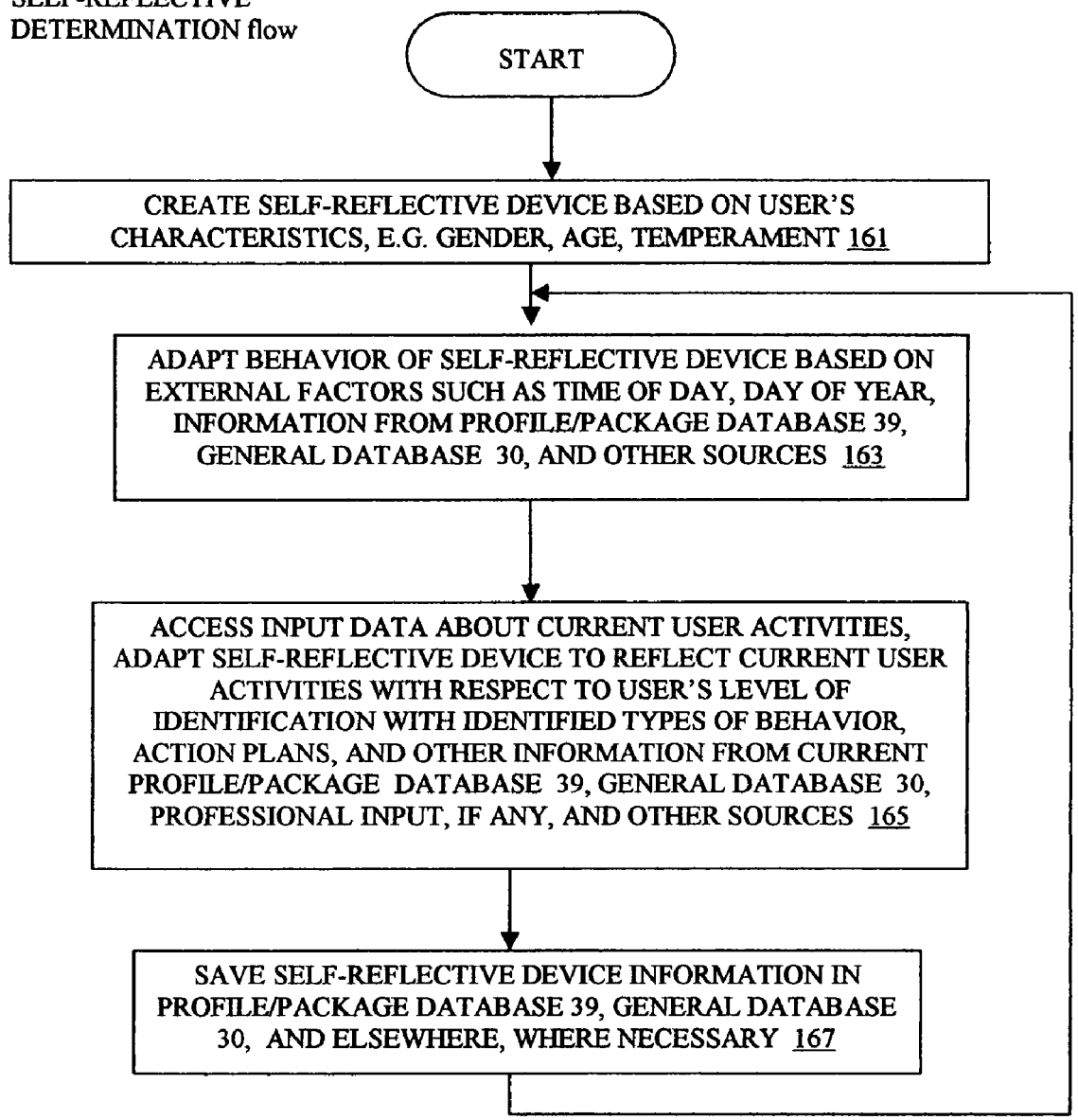
FIG. 8C is a flowchart of self-reflective determination of the illustrative embodiment of the present invention.

Referring now primarily to FIG. 8C, package designer 15 (FIG. 8A) and other modules prepare information required for the self-reflection component of the system. In particular, from profile/package database 39 (FIG. 8A), package designer 15 can determine, for example, the personal physical and emotional characteristics, and stress level, of the user and manifests those characteristics and stress level in, for example, but not limited to, the animated figure known as Charlie. In addition, during data analysis, when the status of the user's behavior ("problem/possible problem/no problem") is determined, package designer 15 (FIG. 8A) can prepare self-reflective information that is specialized for the current status. The method followed by package designer 15 can include, but isn't limited to, the steps of creating a self-reflective device based on, for example, the gender, age, and temperament of the user (method step 161), and adapting the behavior of the self-reflective device based on external factors such as, for example, time of day, day of year, most common behavior problems, particular characteristics of the user, and other information (method step 163). The method can further include the step of accessing input data about current user activities, adapting the self-reflective device to reflect current user activities with respect to, for example, user's level of identification with identified types of behavior, action plans, and other information from the most recent profile/package database 39 (FIG. 8A), general database 30 (FIG. 8A), and professional input, if any, and other sources (method step 165). The method next includes the step of saving self-reflective device information in, for example, profile/package database 39, general database 30, and elsewhere where necessary, so that it may be accessed by feedback provider 17 (FIG. 8A) (method step 167). The loop may continue with method step 163.

Figure 8D:
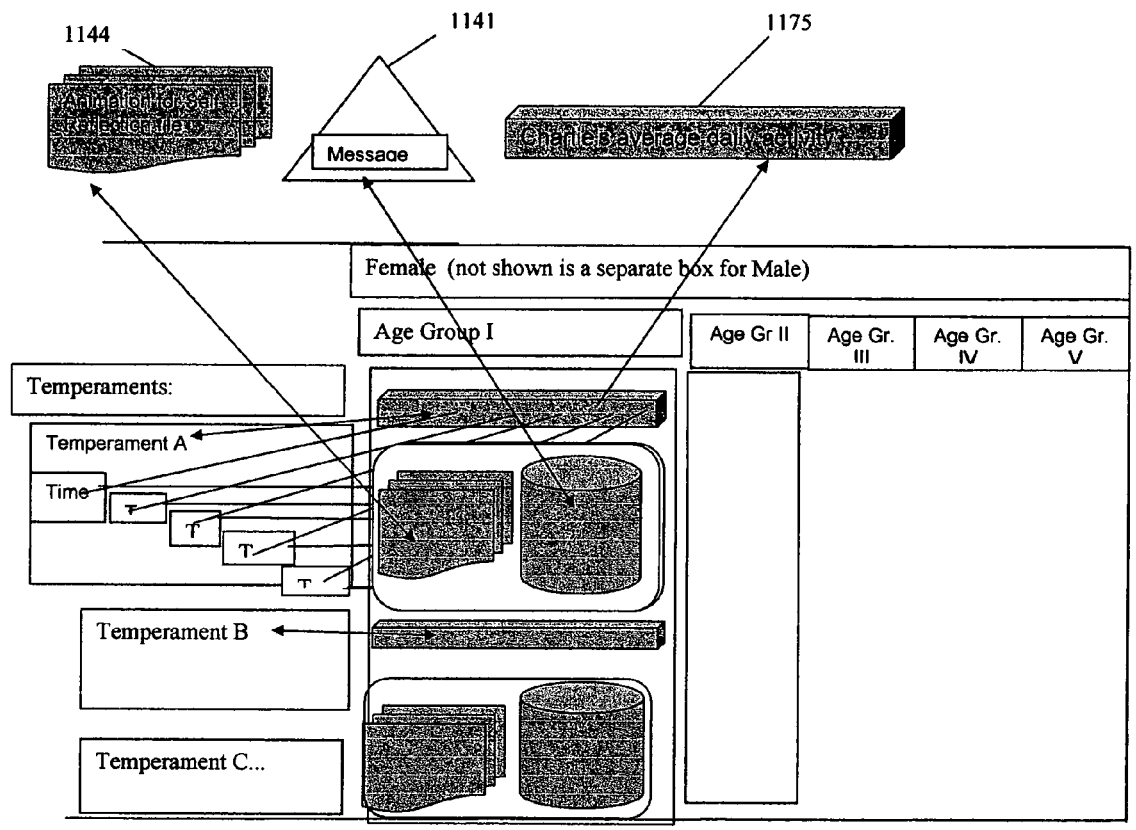
FIG. 8D is a pictorial representation of the characteristics that can be associated with the self-reflective device.

Referring now to FIG. 8D, the self-reflective device, Charlie, behaves, in the illustrative embodiment, according to, for example, information provided from various sources including, but not limited to, an animation database 1144, a congratulations messages 1141, and a daily activity database 1175. Charlie's reaction to a variety of current user activities can be based on, for example, the temperament, gender, and age of the user, and the time of the day. As shown, for each temperament type, each gender, each age, and each time of day, a baseline for Charlie's actions can be identified. User-activity-specific reactions can be overlain on Charlie's baseline user-specific reactions.

Figure 9A:
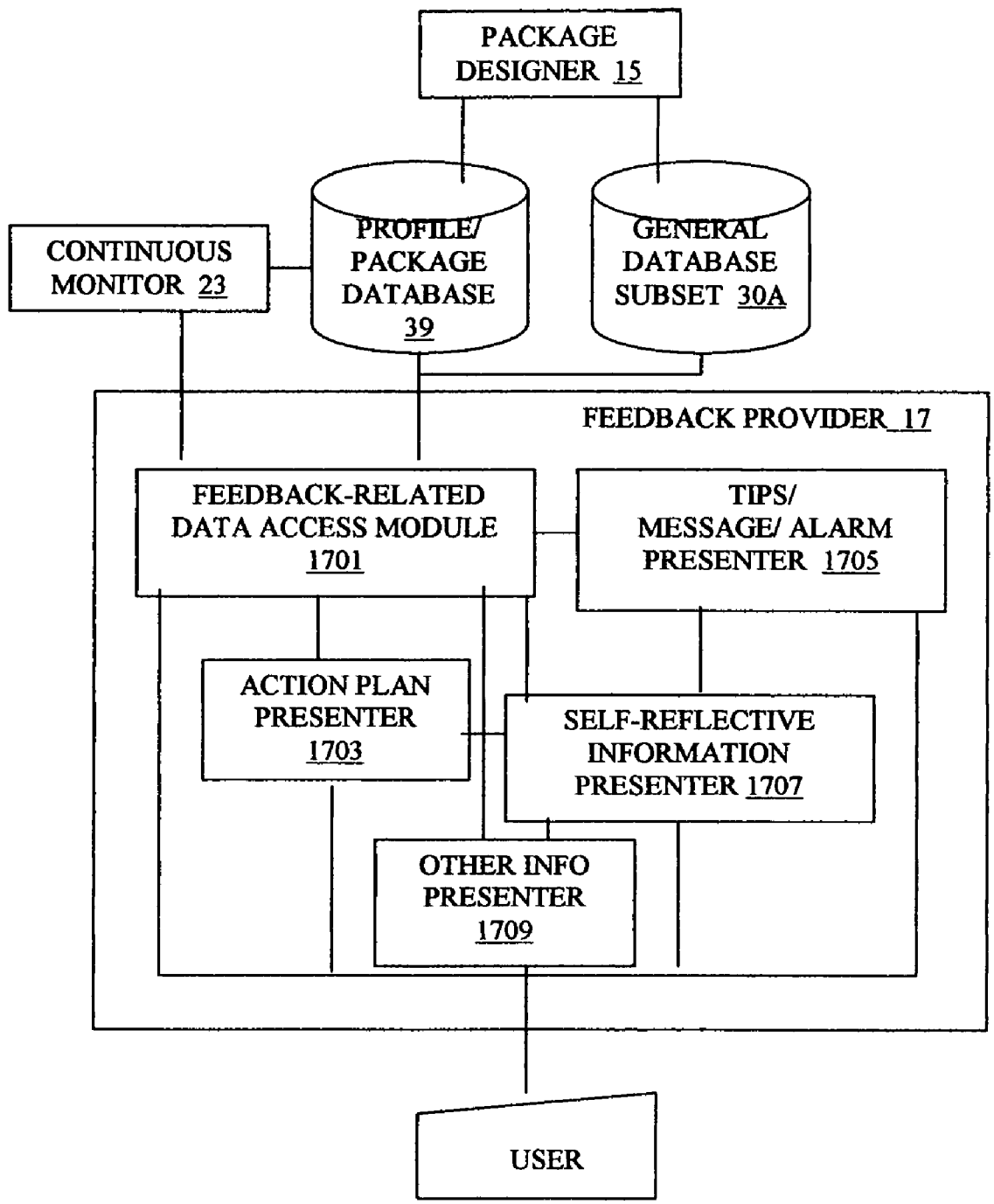
FIG. 9A is a schematic block diagram of the feedback provider of the illustrative embodiment of the present invention.

Referring now to FIG. 9A, feedback provider 17 presents analyzed information to the user in ways, for example, that encourage the user to use the system and therefore benefit by the system's analysis of the user's activities with respect to pre-determined behavior patterns. Feedback provider 17 includes, but isn't limited to, modules such as feedback-related data access module 1701, action plan presenter 1703, tips/message/alarm presenter 1705, self-reflective information presenter 1707, and other information presenter 1709. Feedback provider 17 can provide feedback to the user based on data input from the user, analysis of that data, professional input, etc., such as, for example, tips, advance alarms, reminders, menus, commercial food guidelines, pyramid-based food guidelines, balance scale, yoga guidelines, stretching guidelines, general exercise guidelines, fitness tests, nutrition planning information, nutrition schedule, action plans, milestones, and list of reached or failed action plans. Note that the balance scale and the star system (described below) are quite general and can refer to information other than fitness and nutrition. Self-reflective information presenter 1707 delivers information on the current status of a previously-identified behavioral pattern. Also, self-reflective information presenter 1707 can interrupt the normal flow of information being presented to the user in order to deliver high-priority, time-critical feedback to the user. In this way, the user can view her own activity by watching self-reflective information presenter 1707. In addition, each, possibly animated, message delivered by self-reflective information presenter 1707 is logged so that the user may scroll through these messages at a later time to review a reflection of her activities throughout the time period. Feedback provider 17 can also, for example, present stress management information, which gives feedback to the user when data analyst 13, for example, detects something irregular with respect to thought and feeling. Feedback provider 17 can also present, for example, corrective thoughts and beliefs, to counteract the user's thoughts and beliefs with respect to the identified types of behavior. Tips/message/alarm presenter 1705 can include tips from, for example, general database subset 30A, profile/package database 39, or those recommended by a professional. Tips from various sources could be highlighted for emphasis. Action plan presenter 1703 visually relates goals and action plans for the user's review. Based on the types of behavior identified with the user's actions, and the current user activities with respect to those types of behavior, feedback provider 17 accesses dynamically variable data sets in profile/package database 39 and general database subset 30A and recommends, for example, action plans to the user (and relevant tips and animation). Other information presenter 1709 can present other information, as required, to the user.

Of particular interest to user is the feedback provider's 17 (FIG. 9A) balance scale star system (see FIGS. 14N/M). Stars system 82 (FIGS. 14N/M) are shown to depict a caloric balance. The number of stars in star system 82 under the pyramid can depend on the number of calories banked from the food intake and the number of calories spent in exercising. For example, there could be four types of caloric balance: (1) no nutrition calories banked and no fitness calories spent—half-star; (2) nutrition calories banked <50 and fitness calories spent <50—full star; (3) nutrition calories banked <250 and fitness calories spent <100—two stars; and (4) nutrition calories banked $\geq$250 and fitness calories spent $\geq$100—three stars. Tips that show, for example, the number of banked calories and corresponding calculated number of pounds (for example, "You banked X calories which is less than Y lb") may be provided. Tips may be, for example, organized into groups that coincide with the number of calories banked from the food intake and the number of calories spent in exercising, but tips can be organized in any meaningful way. For example, tips may be categorized as follows: (1) if no nutrition calories banked and no fitness calories spent, a first category of tips is chosen; (2) if nutrition calories banked <50 and fitness calories spent <50, a second category of tips is chosen; (3) if nutrition calories banked >250 and fitness calories spent <100, a third category of tips is chosen; and if nutrition calories banked $\geq$250 and fitness calories spent $\geq$100, a fourth category of tips is chosen. Within the selected category, the first tip is shown by default. For example, if the caloric balance is "Half-star" or no calories are "saved" and no calories are spent in exercise, then the tips might be as follows:

a) Muscles which are worked or used regularly often benefit from a rest day.

b) Occasionally consuming the proper number of calories can actually help in that your metabolism is less likely to slow down due to the normally lowered caloric intake.
c) Give yourself credit for not throwing in the towel and overeating today!
d) You are now refueled and energized to greet tomorrow!

If the caloric balance is "Full-star", or nutrition calories have been "saved" OR fitness calories have been used, the tips might be as follows:
a) Accomplishing some of our daily goals, if not all of them, is still an accomplishment!
b) Now you can plan that tomorrow you will complete both goals.
c) Write down three reasons why you didn't accomplish your other goal, forgive yourself, and look forward to tomorrow's efforts!
d) Recognize how important the goals that you completed today are to your long term goal.

If the caloric balance is "Two stars", or 200-300 nutrition calories have been "saved" and <100 fitness calories have been used, the tips might be as follows:
a) You're on the right track! Tomorrow you will exercise a little longer or harder.
b) Good job! Now maybe you need to change to an activity you enjoy more?
c) Did you run out of time to complete your workout? Something is better than nothing—tomorrow you'll plan to have more time.
d) At this rate, you will lose about_pound/week. With more exercise, you could lose more!

If the caloric balance is "Three stars", or 250+ nutrition calories have been "saved" and >100 fitness calories have been used, the tips might be as follows:
a) You're on a roll, keep up the great work!
b) Mission accomplished! Let's duplicate this effort tomorrow!
c) Feeling like a million bucks? That's what dedication gets you!
d) Most people recognize that when their nutrition is "on track," their exercise is likely to be also. Looks like yours is too!
e) Do this for a week then reward yourself with a non-food "treat" like a new CD, a movie or a massage!

Figure 9B:
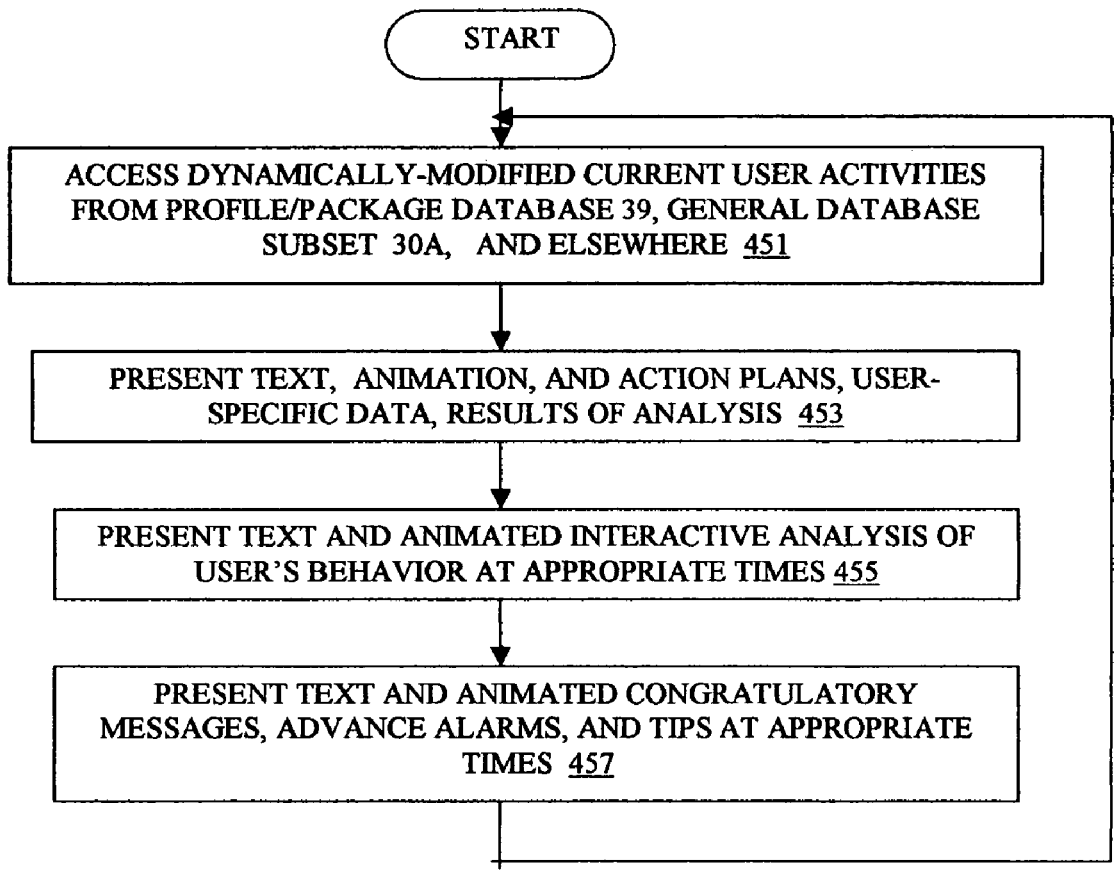
FIG. 9B is a flowchart of the feedback provider of the illustrative embodiment of the present invention.

Referring now to FIG. 9B, the loop of feedback provider 17 (FIG. 9A) of the illustrative embodiment of the present invention can include, but isn't limited to, the following steps, including the step of accessing, for example, dynamically-modified user-specific data, analyzed data, action plans, tips, congratulatory messages, and self-reflective information that have been prepared to help the user address an identified type(s) of behavior (method step 451). The loop can continues with the step of presenting dynamically updated action plans, user-specific data, professional input, if any, and results of data analysis to the user in a format, for example, animated, that entices the user to pay attention to the presented information, to become emotionally involved in the information being presented (method step 453). The loop can further continues with the further step of presenting an interactive analysis of the user's behavior, influenced by the user's profile in order to encourage the user's emotional involvement, to the user at times such as, for example, when the user could use encouragement or when the user needs a reminder (method step 455). The interactive analysis of the user's behavior can be composed of user-specific data such as, for example, gender, age, and temperament, and can react to and modify dynamically changing user activities, time of day, and day of year. The loop can further include the step of presenting, for example, text and dynamically variable animated congratulatory messages, advance alarms, and tips to the user at times such as, for example, when the user might need information about how best to implement an action plan, or when the user has made progress towards a desired goal, or when the user desires to see historical text and animated messages (method step 457). The loop can continues at method step 451 to access dynamically-changing data as they become available.

Figure 10A:
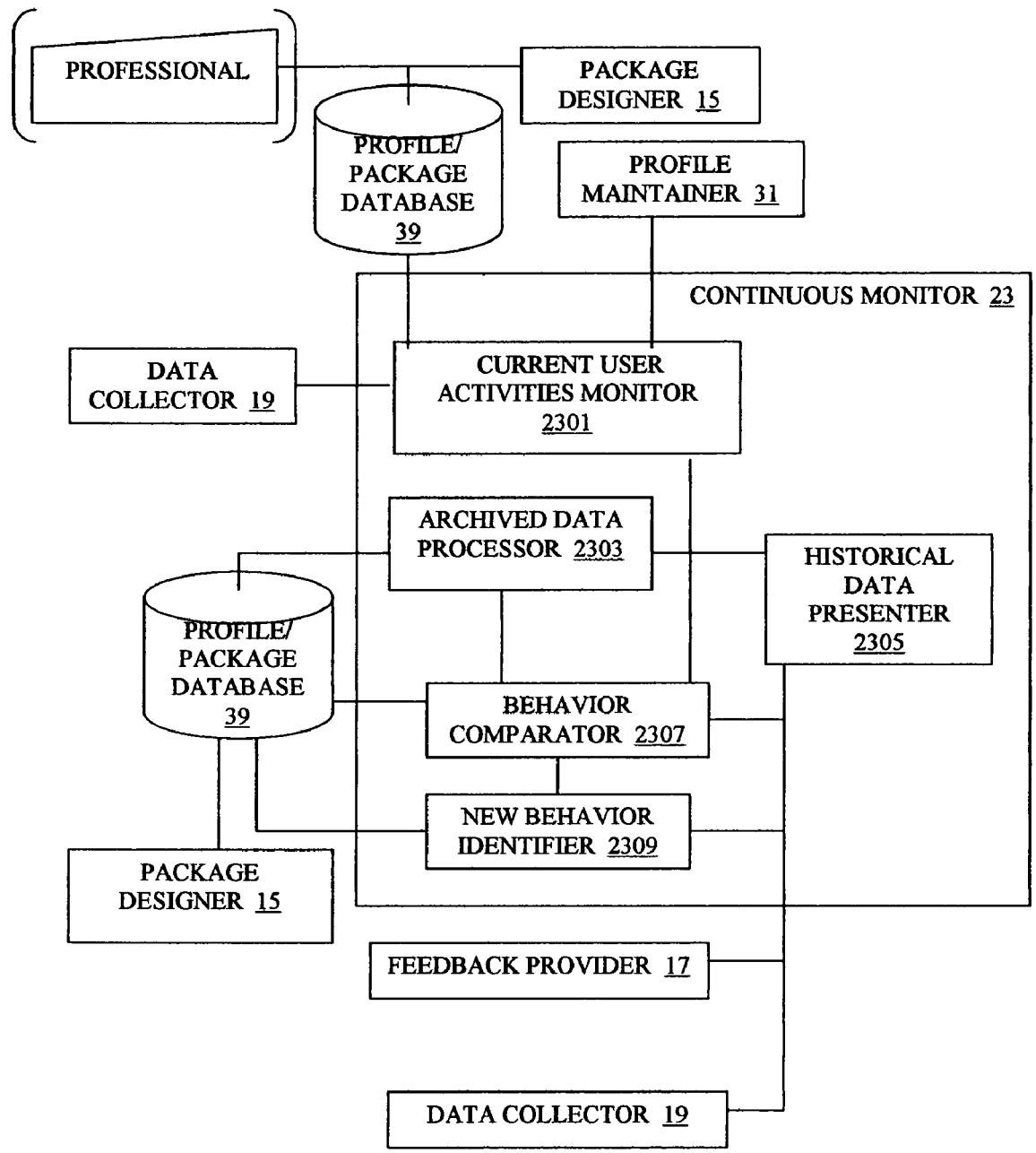
FIG. 10A is a schematic block diagram of the continuous monitor of the illustrative embodiment of the present invention.

Referring now to FIG. 10A, continuous monitor 23 of the illustrative embodiment of the present invention checks information that the user regularly enters against specific (but possibly variable) rules and instructs feedback provider 17 to give the user an estimation of progress against the action plan, among other feedback. Continuous monitor 23 can detect, for example, specific behavior patterns that indicate that the user might be backsliding and can provide, for example, advance alarms and tips to the user to help the user prevent the backslide, or to begin the process of identifying the user once again with the type of behavior. Even if the user has not been previously associated with a behavior problem through a previous analysis, the system is able to detect common behavior problems. Continuous monitor 23 includes, but is not limited to, current user activities monitor 2301, that processes input from, for example, profile/package database 39, data collector 19, and profile maintainer 21. Behavior comparator 2307 can receive information from any of several sources, including but not limited to, archived data processor 2303, profile/package database 39, and current user activities monitor 2301, that allows a comparison of behavior across time. These time-based data can also be made accessible to the user by historical data presenter 2305. Progress against previously-determined behavior types can be estimated and provided to the user. New behavior identifier 2309 can compare the current user activities to types of behavior that the system recognizes and, in thus doing so, can possibly identify the user with further types of behavior. Results of these comparisons are provided immediately to feedback provider 17 and data collector 19, and, through profile/package database 39, to package designer 15, and professional, if any. Note that data collector 19 can also provide current user activities to data analyst 13, which in turn can provide analyzed data to profile maintainer 21, which ultimately can provide analyzed data to continuous monitor 23.

Figure 10B:
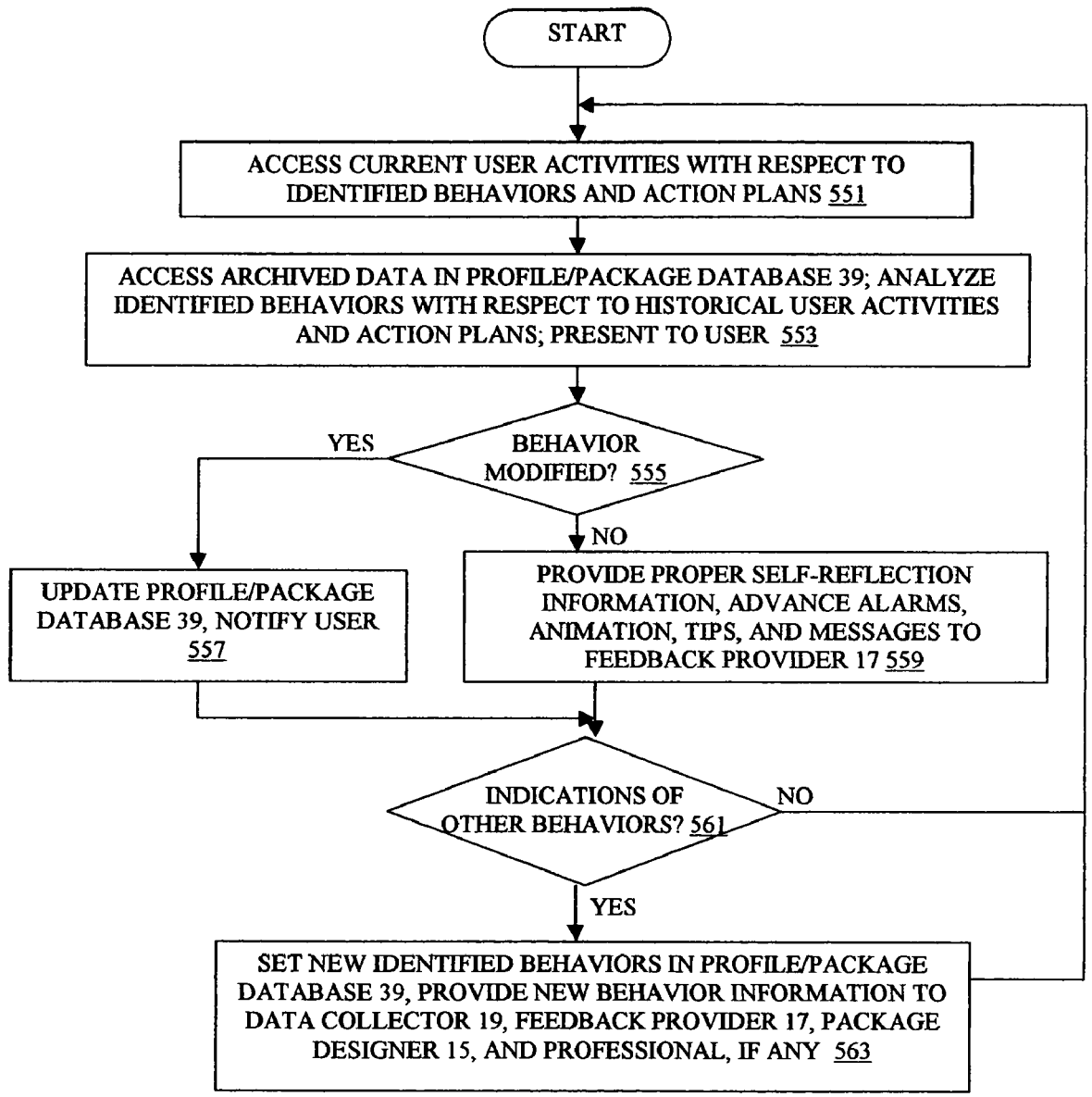
FIG. 10B is a flowchart of the continuous monitor of the illustrative embodiment of the present invention.

Referring now to FIG. 10B, the method of continuous monitor 23 (FIG. 10A) of the illustrative embodiment of the present invention includes, but is not limited to, the loop of accessing dynamically changing user current activities (method step 551), and accessing archived data, analyzed user data, professional data, if any, and other data, and determining if there are indications that the identified behavior pattern is returning, and presenting this information to the user (method step 553). If it appears, from the user's thoughts, actions, and feelings, that the user's behavior is not been sufficiently modified (decision step 555), the method can further include the step of presenting self-reflection information, advance alarms, tips, animation, and other kinds of messages to the user concerning the behavior problems identified during a previous analysis and/or the most common behavioral problems (method step 559). If the user's behavior has been modified (decision step 555), the method can further include the step of updating user-specific data such as, for example, profile/package database 39 (FIG. 10A), and notify the user (method step 557). If the current user activities, with respect to archived user activities, indicate other possible behavior patterns (decision step 561), the method can include the step of providing that information to data analyst 13 (FIG. 10A), package designer 15 (FIG. 10A), and others through profile/package database 39 (FIG. 10A), and, for example, alerting the user through feedback provider 17 (FIG. 10A) and/or data collector 19 (FIG. 10A). If the current user activities, with respect to archived user activities, indicate no other possible behavior patterns (decision step 561), the method repeats the preceding steps beginning at method step 551.

Referring now to FIG. 11A, professional interface 16 provides the professional or another source of relevant data to the system a means for establishing communications with and providing advice for the user, as well as for modifying user-specific data, including user-specific rules, that drive the system. Professional interface 16 includes, but is not limited to, data receiver 1601 that receives from data analyst 13, user registrar 11, package designer 15, among others, and retrieves from profile/package database 39 user data that have been collected and analyzed. These data can be presented to the professional or other source by analyzed data presenter 1607 using, such as, for example, interface screens such as those found in FIGS. 15G and 15H. These types of interface screens can be used by professional information receiver 1609 to receive information from the professional(s) with respect to the types of behavior the user is identified with, for example. Professional data manipulator 1605 and filter preparer 1603 interpret professional can input and proliferate database changes to the user-specific data and rules.

Referring now to FIG. 11B, the method of professional interface 16 (FIG. 11A) of the illustrative embodiment of the present invention can include, but isn't limited to, the steps of accessing and presenting current and archived user-specific data and rules to professional (method step 651), and receiving input from the professional including, but not limited to, comments, rule changes, advice, etc. (method step 653). The method can further include the step of updating user-specific data, including, for example, user-specific rules and user-specific filter 34 (FIG. 11A), and proliferating those changes to relevant parts of the user-specific information in profile/package database 39 (FIG. 11A) (method step 655), and, if necessary, providing collaboration information including, for example, advice, tips, messages, and information to the user based on the combination (method step 657). The method can further include the step of moving any updates to a storage area such as, for example, profile/package database 39, filter 34, and general database 30 (FIG. 11A). The method can continues with method step 651.

Referring now to FIG. 11C, possible actions that a professional may take with respect to patient groups and databases are shown. These various actions can be chosen by the professional accessing the illustrative server screen shown in FIG. 15I. For example, the professional could create/manage workouts and exercises 670 through use of the illustrative server screen of the type, but not limited to, shown in FIGS. 15E/F. The professional can organize patients by groups 672 and manage the transmission of information to groups of patients having similar characteristics. The professional can customize patient care in groups or individually by manipulating database values in a patient-specific way, or across patients or patient groups.

Figure 12A:
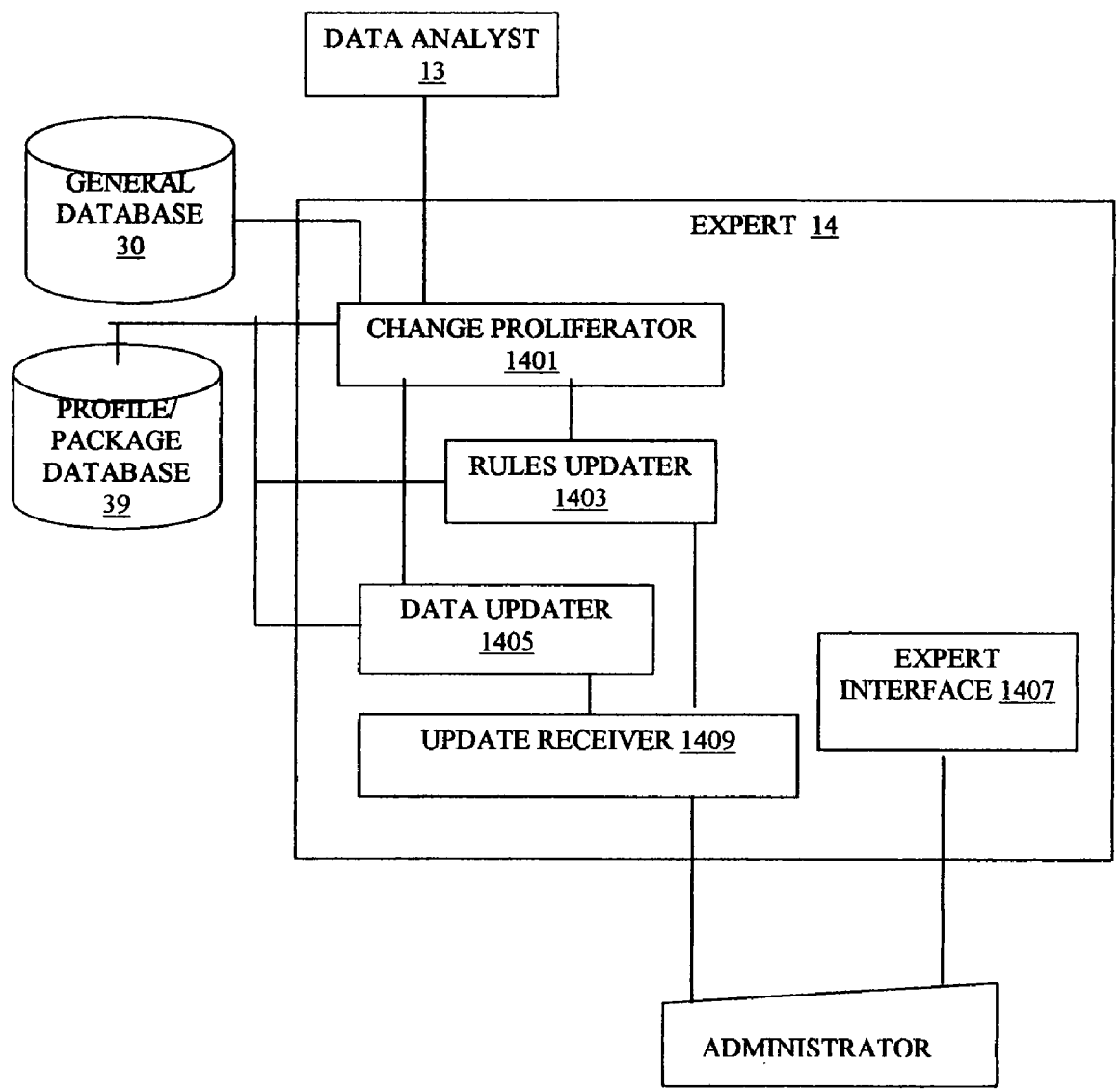
FIG. 12A is a schematic block diagram of the expert of the illustrative embodiment of the present invention.

Referring now to FIG. 12A, expert 14 of the illustrative embodiment of the present invention includes, but is not limited to, change proliferator 1401, rules updater 1403, data updater 1405, expert interface 1407, and update receiver 1409. Expert 14 allows fundamental changes to general database 30, profile/package database 39, and other databases of the system of the illustrative embodiment of the present invention. Further, these changes are proliferated automatically to related data structures and to remote databases. Expert interface 1407 can present an administrator with options for possibly modifications that could be made to available databases. Update receiver 1409 can process the administrator's entries. Data updater 1405 can access appropriate database(s) to modify the selected data. Rules updater 1403 can access appropriate database(s) to modify the selected rules. Change proliferator 1401 can determine how requested modifications affect other parts of the databases and other databases, and can insure the integrity of the database structure by automatically making appropriate changes.

Figure 12B:
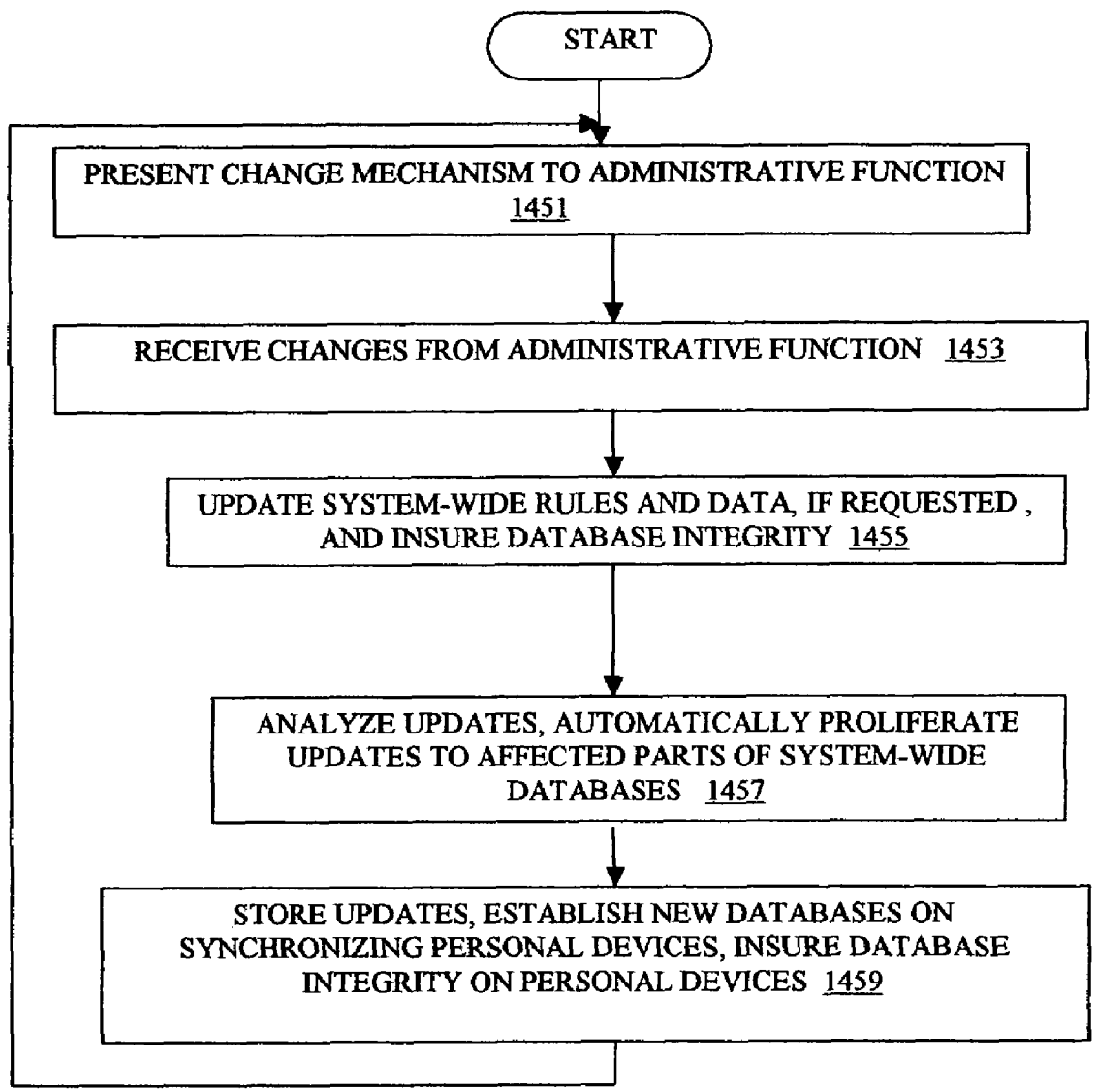
FIG. 12B is a flowchart of the expert of the illustrative embodiment of the present invention.

Referring now to FIG. 12B, the method of expert 14 (FIG. 12A) of the illustrative embodiment of the present invention includes, but isn't limited to, a loop with steps of presenting a change mechanism to an administrative function (method step 1451) and receiving changes from the administrative function (method step 1453). The loop can have further steps of updating system-wide rules and data, if requested, and insuring database integrity (method step 1455), and analyzing updates to automatically proliferate updates to affected parts of the system-wide databases (method step 1457). The loop can further include the step of storing updates and establishing new database on synchronizing personal devices, if any, and insuring database integrity on personal devices (method step 1459).

Figure 12C:
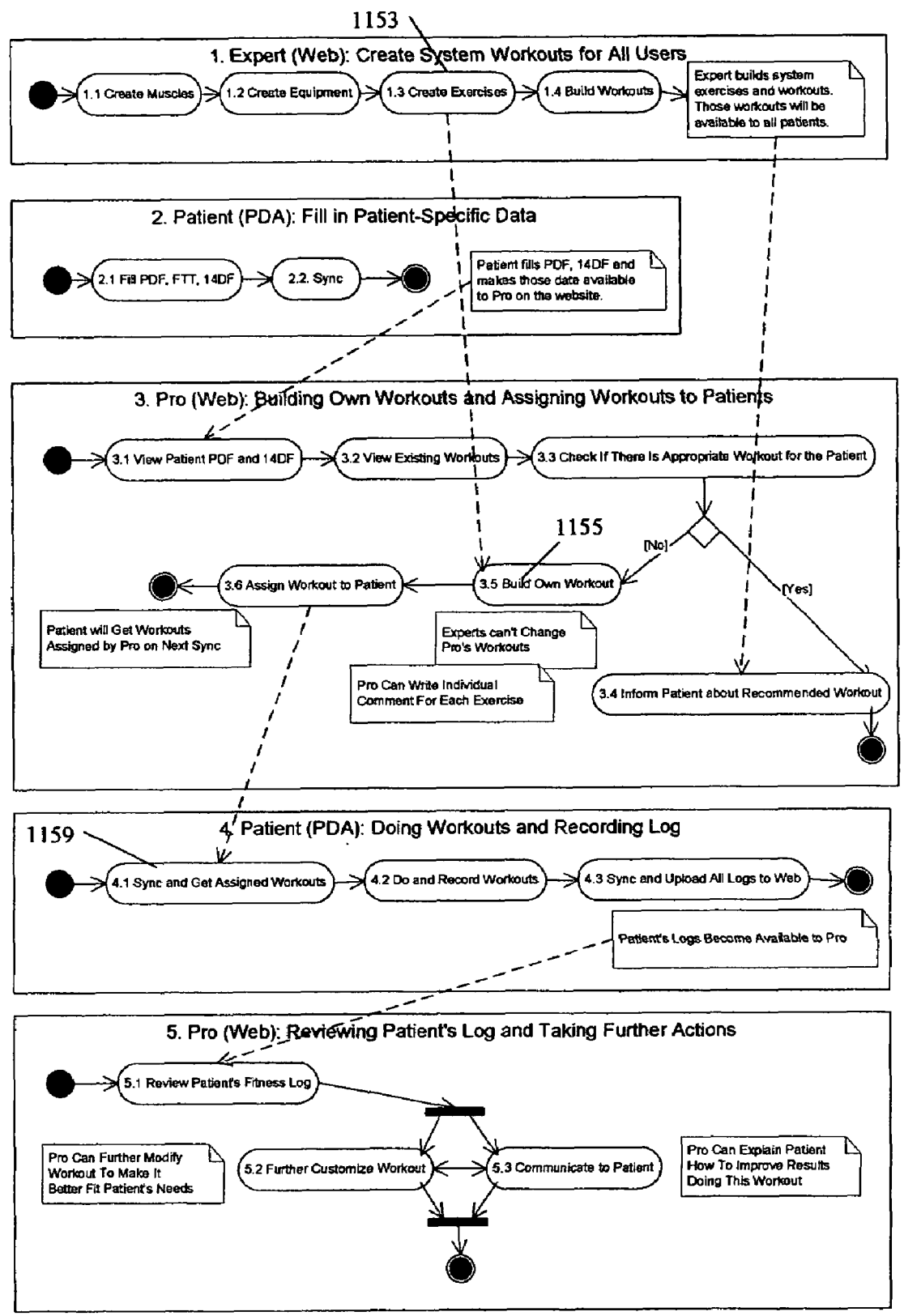
FIG. 12C is a data and control flowchart depicting the interactions among patients (users), professionals, and an expert.

Referring now to FIG. 12C, interactions among an expert, a professional, and a user (patient) are shown graphically in stages. As shown, the expert can create databases (stage 1), the user can provide personal data (stage 2), the professional can access information provided by the expert and the user to create a user-specific package 1151 (FIGS. 13A/C) for the user (stage 3), the user can access the user-specific package, act upon it, and record the results (stage 4), and the professional can review the user's results and take further actions (stage 5). For example, the expert can create initial databases, for example the expert can create exercise databases (step 1153) that can be used by a professional to build a workout (step 1155) and assign a workout to a user (step 1157). The user can synchronize and use assigned workouts (step 1159). The system of the present invention is not limited to this sequence of steps, nor to these particular steps. FIG. 12C is provided as an example of possible interactions.

Figure 13A:
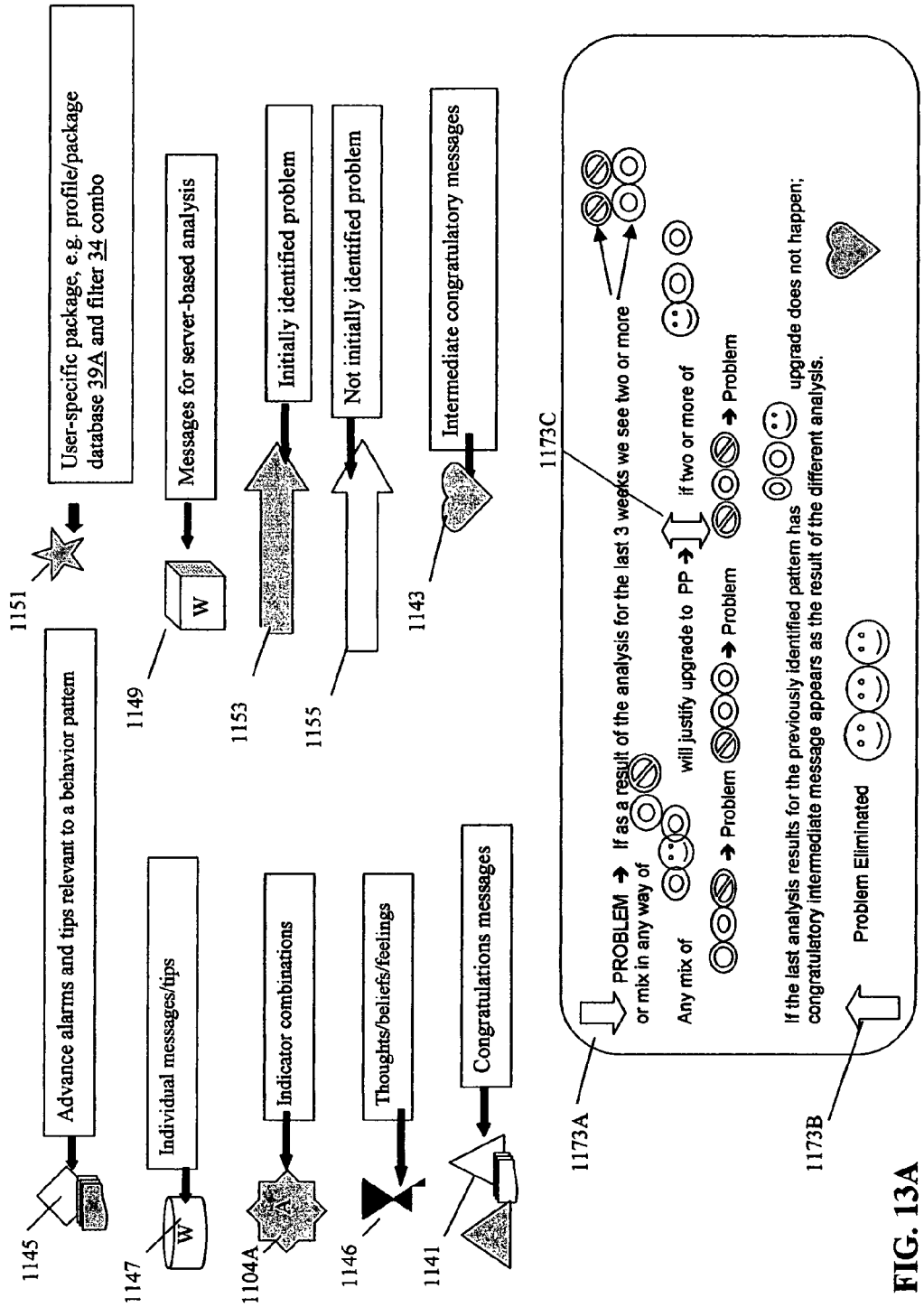
FIG. 13A is a key to the symbols used in FIGS. 13B-D.
Figure 13B:
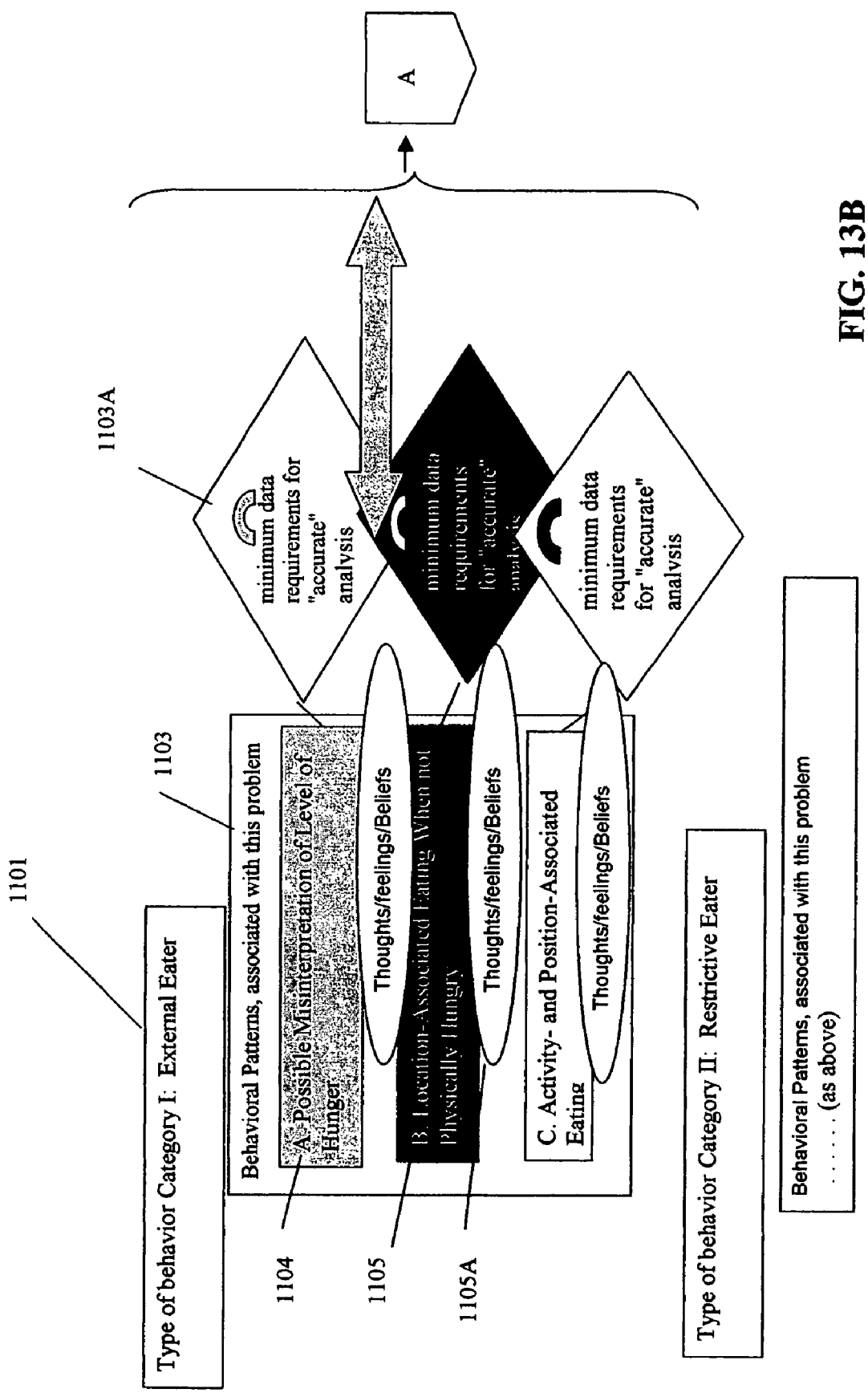
FIGS. 13B-D are schematic diagrams of an illustrative use of the system for a particular type of behavior.
Figure 13C:
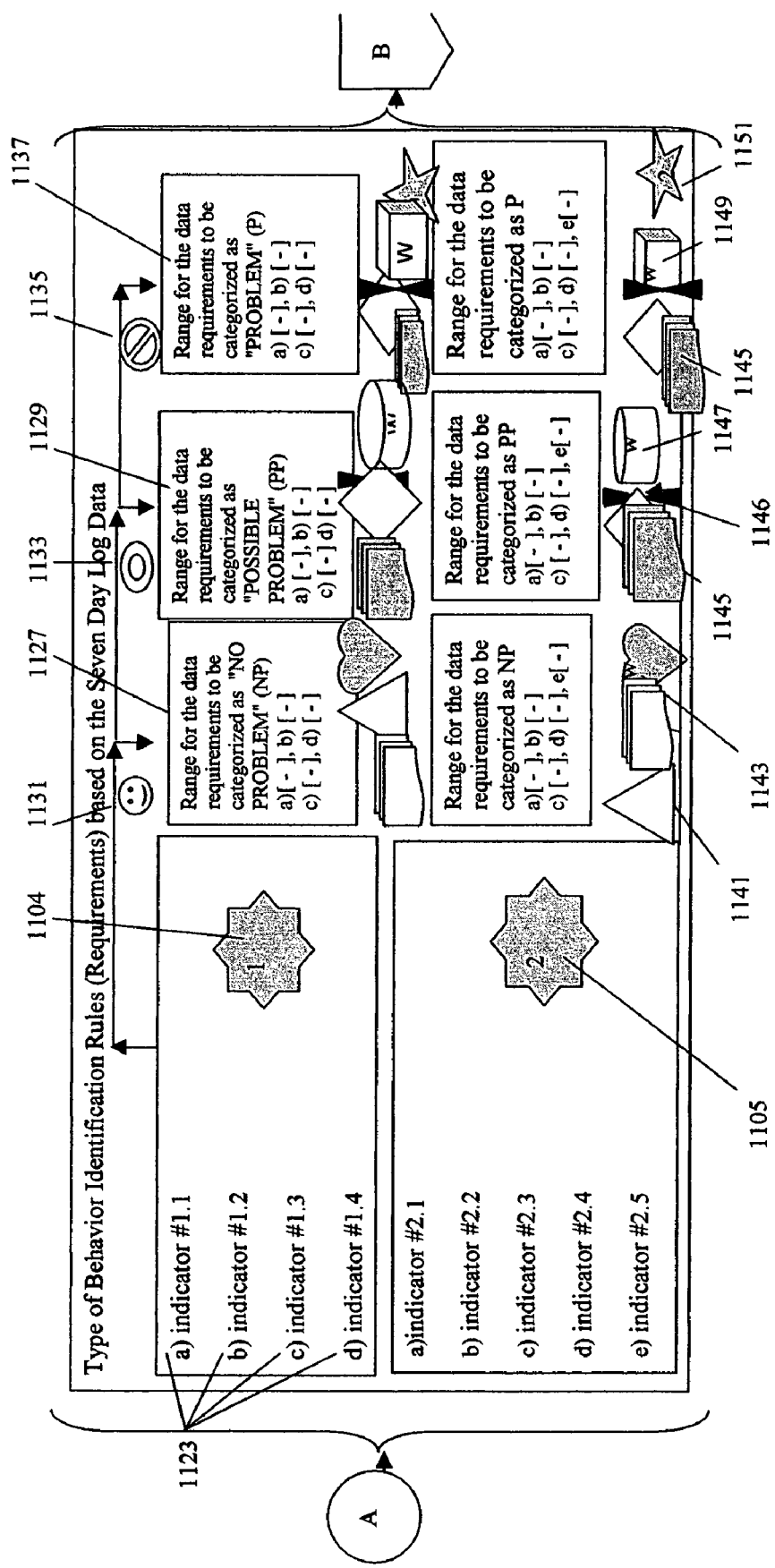
Figure 13D:
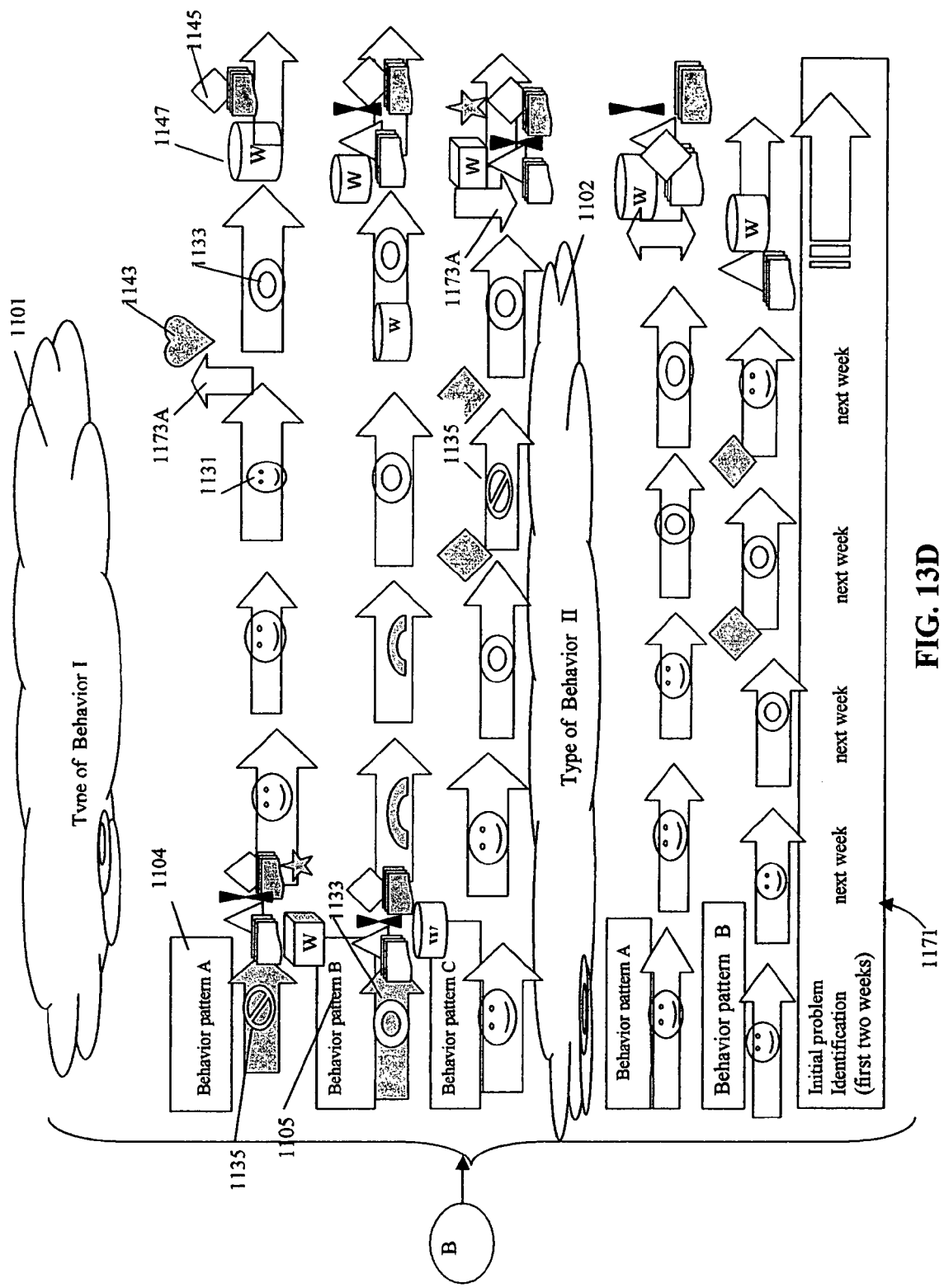

Referring now to FIG. 13A, a key is shown for FIGS. 13B-D. With respect to advance alarms/tips 1145, if, during analysis, the user has been identified as having a "possible problem" (PP) 1173C or a "problem" (P) 1173A (for a specific behavioral pattern), package designer 15 (FIG. 1A) can, for example, enter a tip into the profile/package database 39 (FIG. 1A), or can access the tip through a modification to filter 34 (FIG. 1A) that ultimately directs the extraction of data from general database 30 (FIG. 1A) to general database subset 30A (FIG. 1A). When the current user activities match the requirements for PP 1173C or P 1173A, the appropriate tip can be retrieved from profile/package database 39 or general database subset 30A or elsewhere and presented to the user, for example, in the form of an advance alarm. Also, each message/tip/alarm has the self-reflective device (Charlie) animation and can be shown to the user in the self-reflection file. Each of Charlie's reactions is specific to the duration of the behavioral pattern, after which Charlie's "normal daily activity" resumes until the next "interruption" from this category message/tip/alarm. Individualized messages/tips 1147 are provided for previously identified PP 1173C or P 1173A. These tips can be accessed through the website and can be used during analysis of the user's situation. Server-based analysis messages 1149 are specific to the identified behavior pattern, and are available when the user is identified with the specific behavior. Indicator combinations 1104A can be variations of combinations of the data from the 7-day log that are unique for a particular behavior pattern. Thoughts/beliefs/feelings 1146 and their corrective counterparts are shown by way of example in a previous table. Package designer 15 (FIG. 1A) selects appropriate thoughts/feelings/beliefs and corrective thoughts/feelings/beliefs (based on the user's identified behavioral pattern category) from general database 30, for example. At appropriate times, feedback provider 17 (FIG. 1A) can present appropriate thoughts/feelings/beliefs, corrective thoughts/feelings/beliefs, and individualized animation (for example, by Charlie), based on the user's identified behavioral pattern category. Charlie's average daily activity directly depends on the temperament test results, gender, age group and type of behavioral pattern that user has been identified with.

Continuing to refer primarily to FIG. 13A, congratulations messages 1141 are presented to the user who had previously been identified with a behavioral pattern as a PP 1173C or P 1173A, but who has partially or completely eliminated the pattern as exhibited by current user activities. Congratulations messages 1141 can be part of the profile/package database 39 (FIG. 1A), or filter 34 (FIG. 1A) can select them from general database 30 and use them as Charlie's communication tool if the user's status changes to no-problem (NP) 1173B. Intermediate congratulatory messages 1143 can be presented to a user who has shown in the previous analysis improvement in the weekly results. The user, however, has not yet been upgraded to the NP or Problem Eliminated.

Referring now primarily to FIGS. 13B-D, charts of the identification and treatment of a Type of Behavior I 1101 (FIGS. 13B/D), for example, "External Eater", are given. System-defined types of behavior can be stored, in the illustrative embodiment, in types of behavior database 25 (FIG. 1B). All types of behavior include behavior patterns 1103 (FIG. 13B) that are categories of possible various characteristics of user's emotional/psychological status determined, for example, by actions or attempted actions of the user, that define, for example, an External eater. These data can be stored, in the illustrative embodiment, in behavior patterns database 27 (FIG. 1B). The External Eater could either, for example, be broadly characterized as someone who habitually (1) possibly misinterprets of her level of hunger, or (2) engages in location-associated eating when she's not physically hungry, or (3) engages in activity—or position—associated eating, or a combination of these three or more. Data collector 19 (FIG. 1A) can collect and initially analyze information through, for example, the 7-day log, about the user's actions, store the information in profile/package database 39 (FIG. 1A), and pass that information to data analyst 13 (FIG. 1A) for further analysis. Data analyst 13 can map the collected data about the user's actions into system-defined behavior patterns 1103 (FIG. 13B) (if possible) through matching the user's actual indicative actions 1123 (FIG. 13C).

Continuing to refer primarily to FIGS. 13B-D, after the matching process, data analyst 13 (FIG. 1A) compares the number of matches against a number of pre-set thresholds. If the matching process indicates no problem range 1127 (FIG. 13C), that is, for example, a range that is below a "problem" threshold, the user's actions are not deemed to reflect behavior pattern A 1104 (FIGS. 13B/C) with which indicative actions 1123 (see FIG. 13C) are associated, and feedback provider 17 (FIG. 1A) can provide, for example, icon-coded feedback such as "no problem" 1131 (FIG. 13C) and a specialized message related to behavior pattern A 1104 (FIGS. 13B/C). The system provides a preferably customizable set of minimum data requirements for accurate analysis which contains the appropriate ranges (shown in FIG. 13C as no problem range 1127, possible problem range 1129 and problem range 1137). Each individual pattern has an individual set of messages associated with it. Additionally, feedback provider 17 (FIG. 1A) can provide congratulation messages 1141 (FIG. 13C) and intermediate congratulatory messages 1143 (FIG. 13C) if the user had been previously associated with behavior pattern A 1104 (FIGS. 13B/C). This analysis could apply to behavior pattern B 1105 (FIG. 13B) and its behavior pattern B thoughts/feelings/beliefs 1105A.

Continuing further to primarily refer to FIGS. 13B-D, if, on the other hand, the matching process indicates a possible problem range 1129 (FIG. 13C), that is, for example, a range that almost reaches a "problem" threshold, the user's actions are deemed to possibly reflect behavior pattern A 1104 (FIGS. 13B/C) with which indicative actions 1123 (FIG. 13C) are associated. Feedback provider 17 can, in this case, provide the user with, for example, an iconic representation of "possible problem" 1133 (FIG. 13C) and a specialized message related to behavior pattern A 1104 (FIGS. 13B/C). Additionally, feedback provider 17 (FIG. 1A) can retrieve from profile/package database 39 (FIG. 1A) the advance alarm and tips 1145 (FIG. 13C) relevant to behavior pattern A 1104 (FIGS. 13B/C) and provide these to the user. Feedback provider 17 (FIG. 1A) can also provide individualized messages/tips 1147 (see FIG. 13C).

Continuing still further to refer primarily to FIGS. 13B-D, if the matching process indicates problem range 1137 (FIG. 13C), that is, for example, a range of indicative actions 1123 (FIG. 13C) combinations that reaches a "problem" threshold, the user's actions are deemed to sufficiently reflect behavior pattern A 1104 (FIGS. 13B/C) with which indicative actions 1123 (FIG. 13C) are associated. Feedback provider 17 (FIG. 1A) can, in this case, provide the user with, for example, an iconic indicator of "problem" 1135 (FIG. 13C) and a specialized message related to behavior pattern A 1104 (FIGS. B/C). Additionally, feedback provider 17 (FIG. 1A) can provide advance alarms and tips 1145 (FIG. 13C), server-based analysis messages 1149 (FIG. 13C) specific for one of behavior patterns 1103 (FIG. 13B).

Referring now primarily to FIG. 13C, which is a continuation of FIG. 13B, most common behavior problems are always downloaded and available on personal device 61 (FIG. 4A), as well as Charlie's average daily activity. If the user has been identified with "possible problem" or "problem", profile/package database 39 (FIG. 1A) for the user can provide with all the ranges of the combinations to provide for the tips on the personal device in the form of alarms in any modules of the system that the user may use at that moment. For additional feedback, the user is able to view this alarm or messaging in a self-reflection file. For this reason, profile/package database 39 and/or personal device 61 (FIG. 4A) may be equipped with software to present messages such as tips and the animated figure, Charlie, for the problem category.

Referring now primarily to FIG. 13D, an example problem tracking timeline 1171 of system activity is shown for a user identified with two types of behavior, Type of Behavior I 1101 and Type of Behavior II 1102. As shown previously, Type of Behavior I 1101 is, for example, shown with behavior pattern A 1104, behavior pattern B 1105, and another behavior pattern. There could be any number of behavior patterns 1103 (FIG. 13B). During "initial problem identification", or, for example, the first two weeks of operation of data collector 19 (FIG. 1A), data analyst 13 (FIG. 1A) initially identifies the user with Type of Behavior I 1101 through behavior pattern A 1104 and behavior pattern B 1105, for example. An iconic indication such as problem 1135 is associated with behavior pattern A 1104, and iconic indication such as possible problem 1133 is associated with behavior pattern B 1105. By the next week, data analyst 13 (FIG. 1A), for example, determines that the user's psychological and emotional status, in combination with actions or attempted actions or partial actions, show that there is no longer a strong association between the user's activities (physical as well as emotional and psychological) and behavior pattern A 1104. For example, although the period may vary within the scope of the present invention, over the next two weeks, data collector 19 (FIG. 1A) can collect data from the user and can provide the data to, among others, data analyst 13 (FIG. 1A). During this time period, data analyst 13 can determine that the user appears to have shaken behavior pattern A 1104. Data analyst 13 can inform profile maintainer 21 (FIG. 1A) that a change has occurred. Profile maintainer 21 can inform package designer 15 (FIG. 1A) that an update to profile/package database 39 (FIG. 1A) could be necessary to reflect this new status, no problem 1131, and informs continuous monitor 23 (FIG. 1A) to track the user's behavior to make sure behavior pattern A 1104 does not begin recurring. In this example, data analyst 13 (FIG. 1A) considers a problem eliminated when three consecutive weeks pass without the user's exhibiting the behavior pattern A 1104. However, any time period could be chosen to make this determination. When the Type of Behavior I 1101 seems to be eliminated as shown by problem eliminated marker 1173B, data analyst 13 (FIG. 1A) can inform package designer 15 (FIG. 1A) that a revision to the user's action plan (for example a plan that could be found in profile/package data 39 (FIG. 1A)) could be necessary, and package designer 15 (FIG. 1A) can instruct feedback provider 17 (FIG. 1A) to issue an intermediate congratulatory message 1143 to the user.

Continuing to refer to FIG. 13D, as time goes on, continuous monitor 23 (FIG. 1A) could detect a return to the previously-eliminated behavior pattern A 1104 and could instruct feedback provider 17 (FIG. 1A) to present an iconic indication of possible problem 1133 to the user and other indications that the user's activities are indicating a return to a previously-identified behavior such as behavior pattern A 1104. At the same time, continuous monitor 23 (FIG. 1A) can inform package designer 15 (FIG. 1A) that an advance alarm and tip 1145 relevant to behavior pattern A 1104 should be made a part of profile/package database 39 (FIG. 1A) so that feedback provider 17 (FIG. 1A) can present this advance alarm and tip 1145 to warn the user about a possible indicated action identified with the previously-identified behavior pattern A 1104 before the user's activities finalize the behavior pattern A 1104. Also, continuous monitor 23 (FIG. 1A) can provide individualized messages/tips 1147.

Figure 14A:
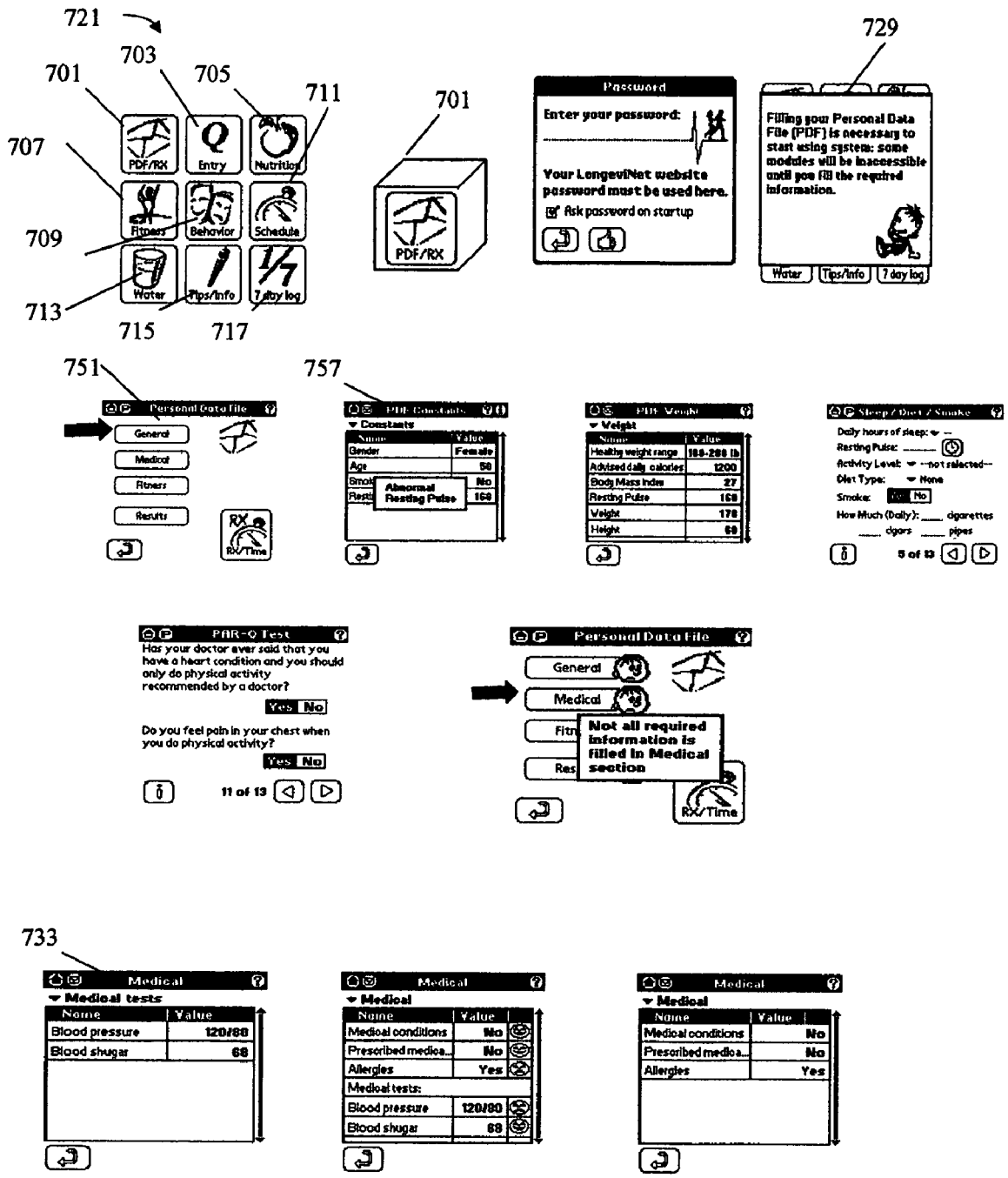
FIG. 14A includes exemplary personal device screen images illustrating personal data file and medical data entry screens.
Figure 14B:
FIG. 14B includes exemplary screens for adding medications.
Figure 14C:
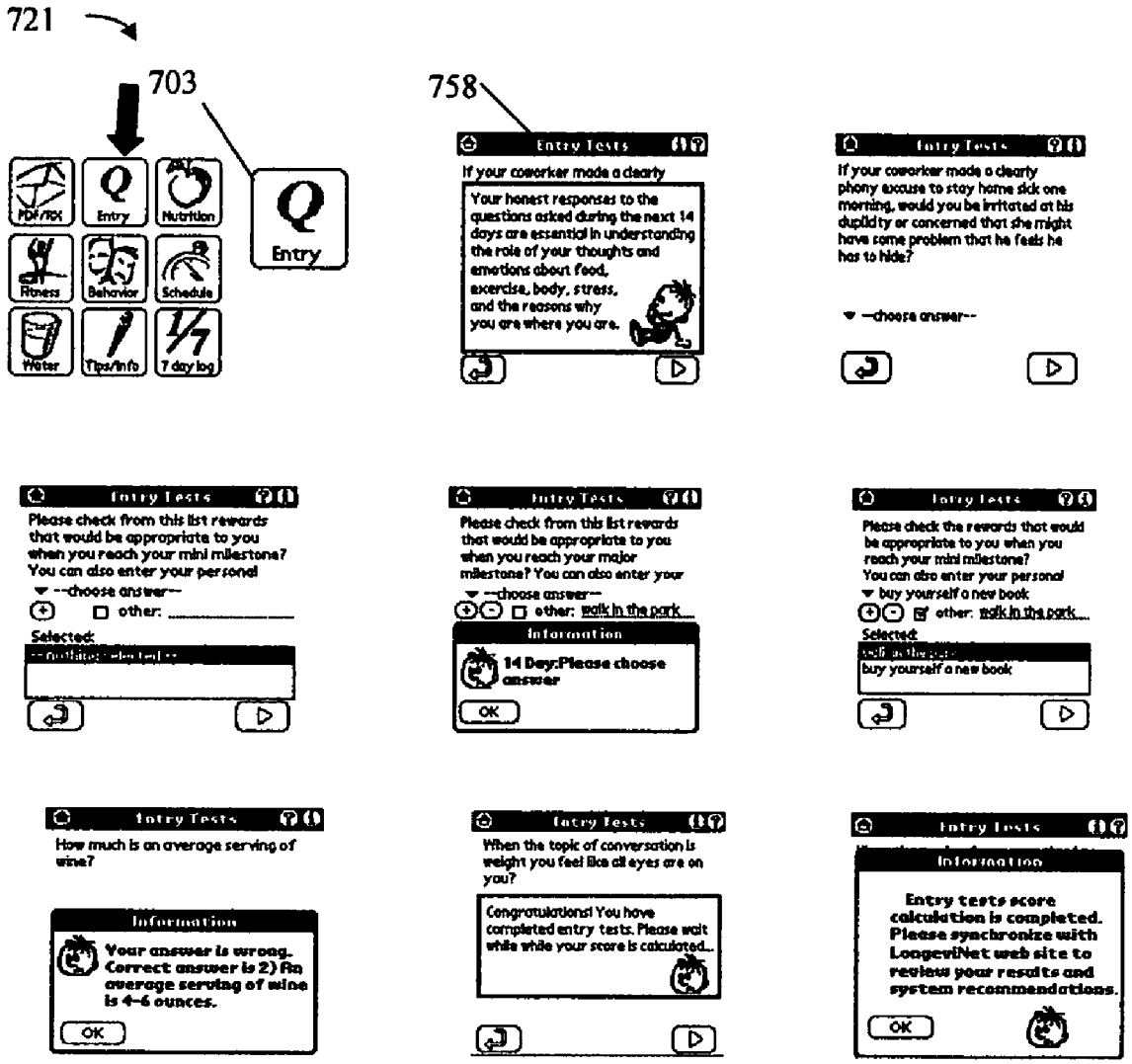
FIG. 14C includes exemplary screens for entry test data entry.
Figure 14D:
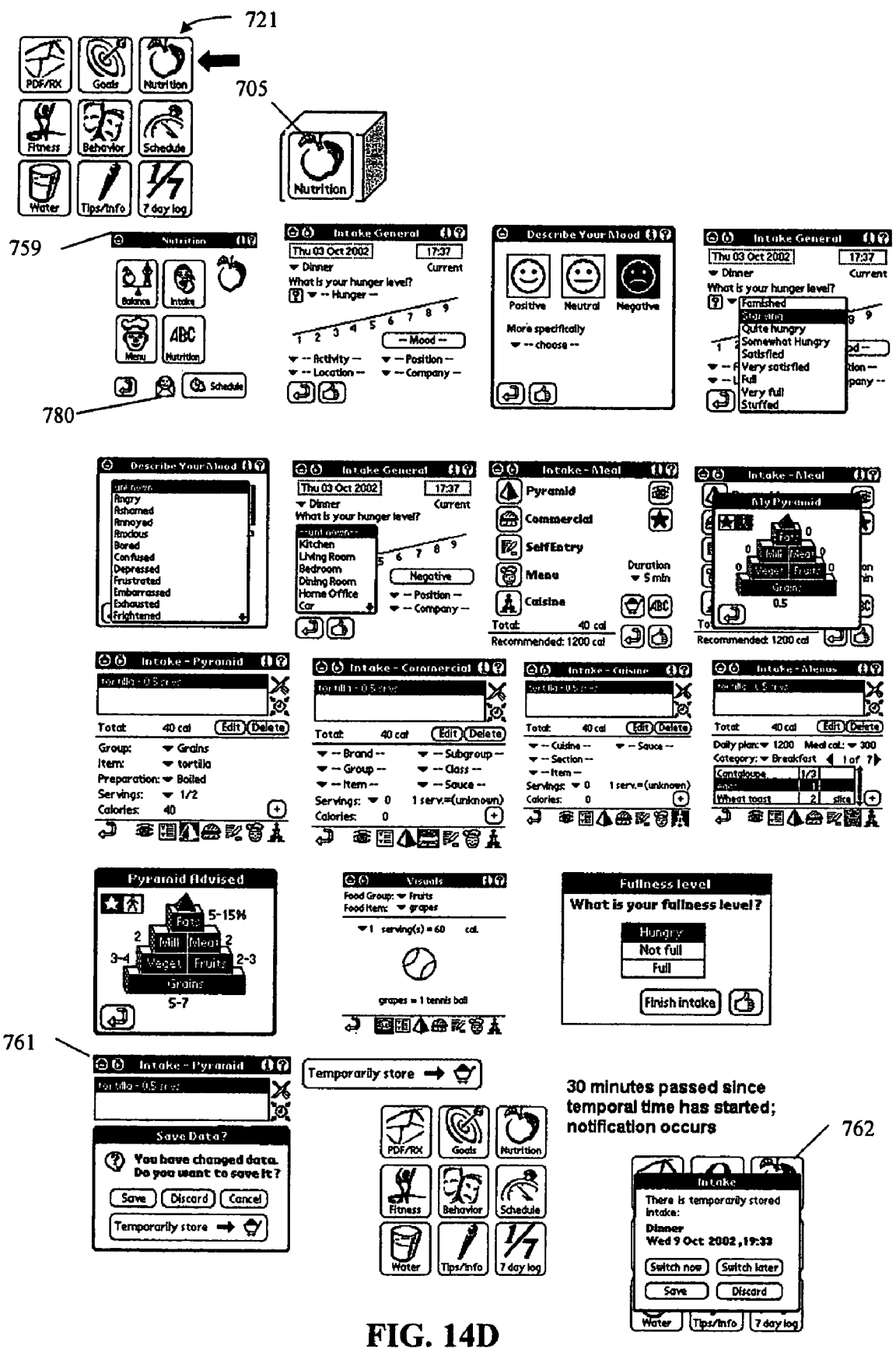
FIGS. 14D-E include exemplary personal device screen images illustrating the choice of the nutrition button.
Figure 14E:
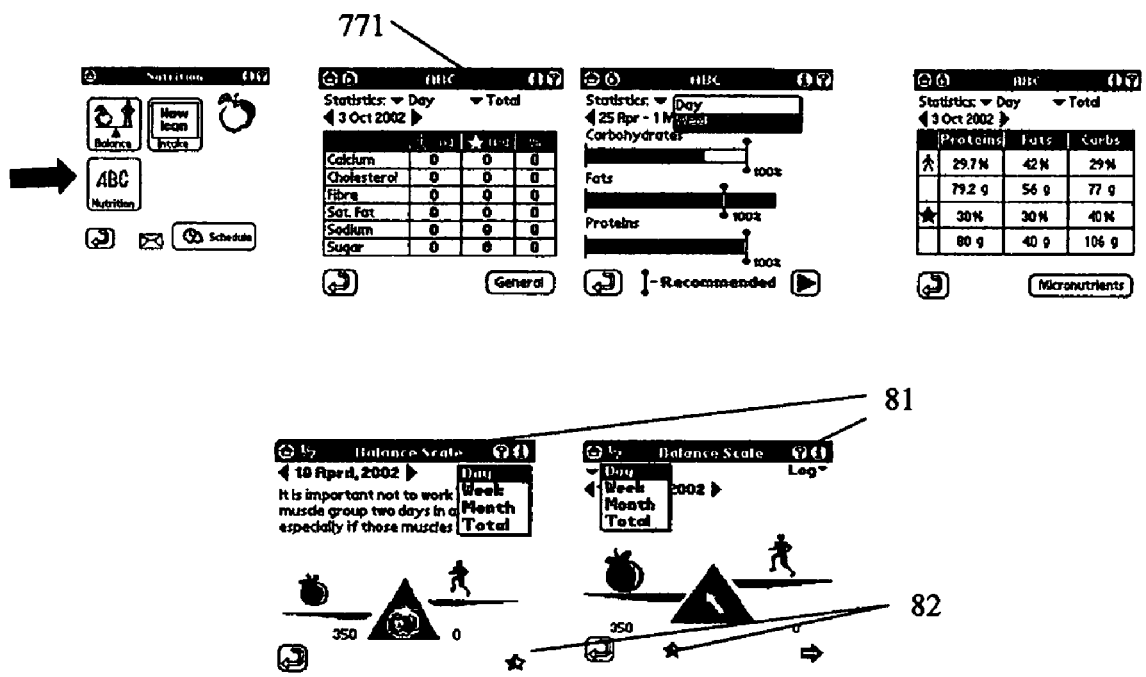
Figure 14F:
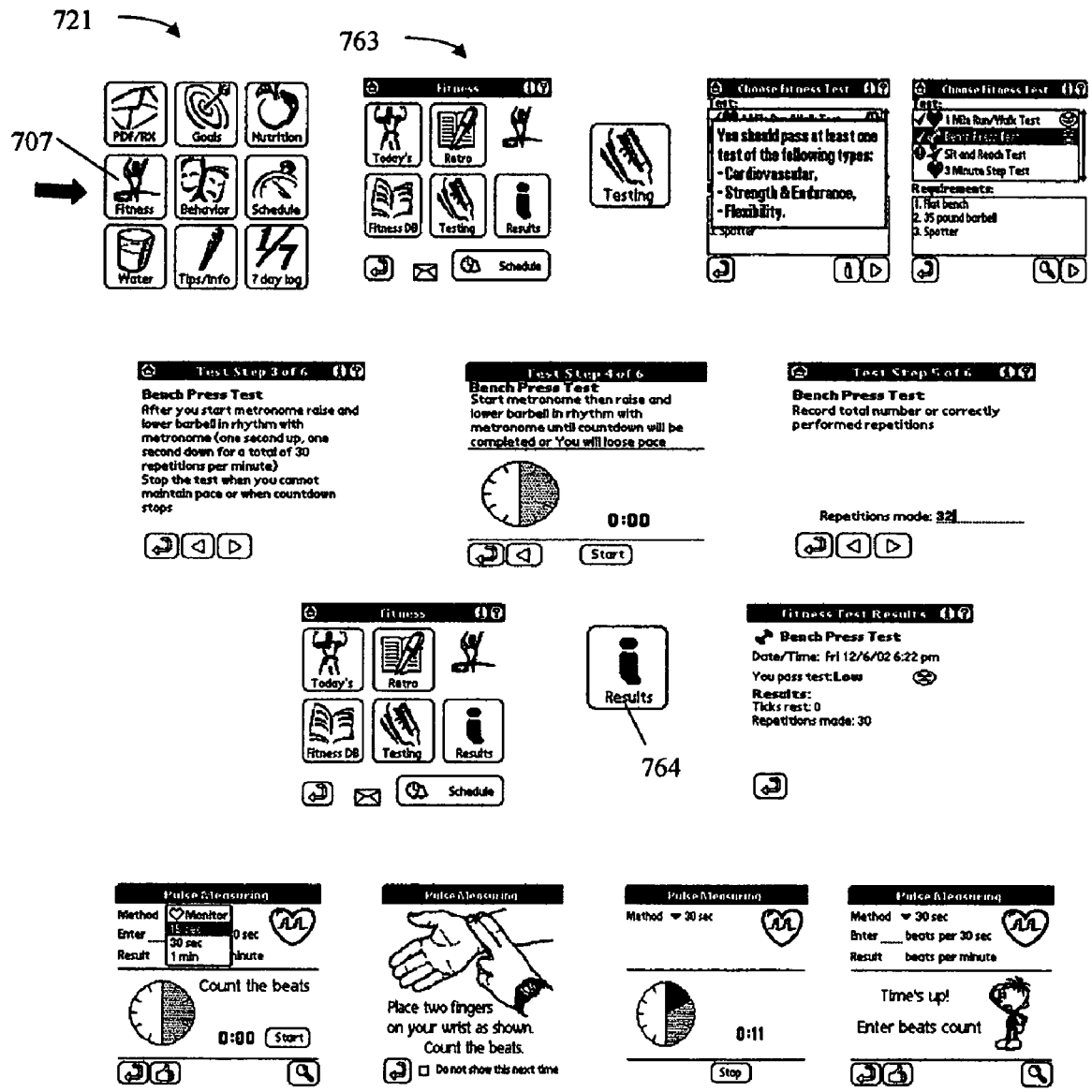
Figure 14G:
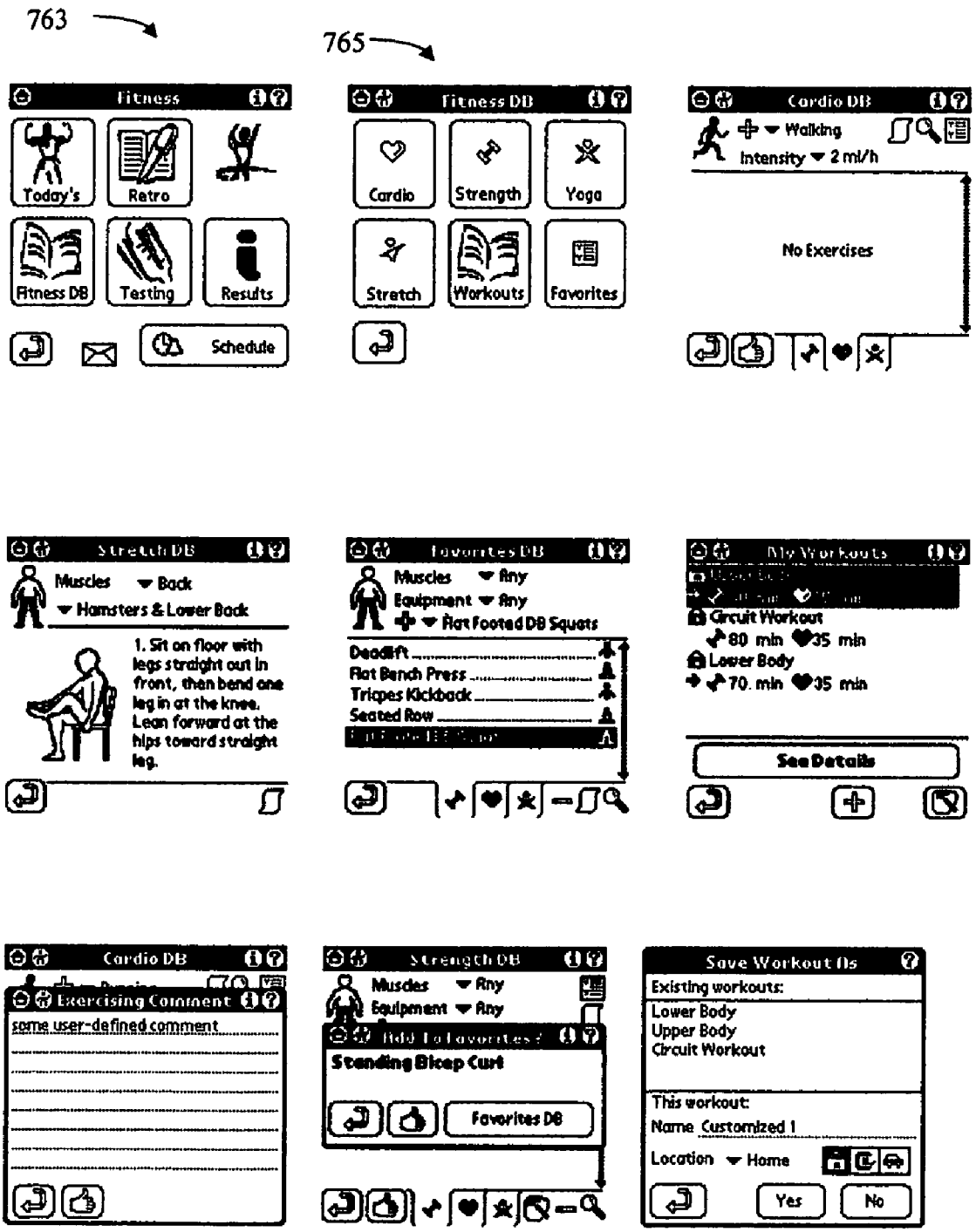
Figure 14I:
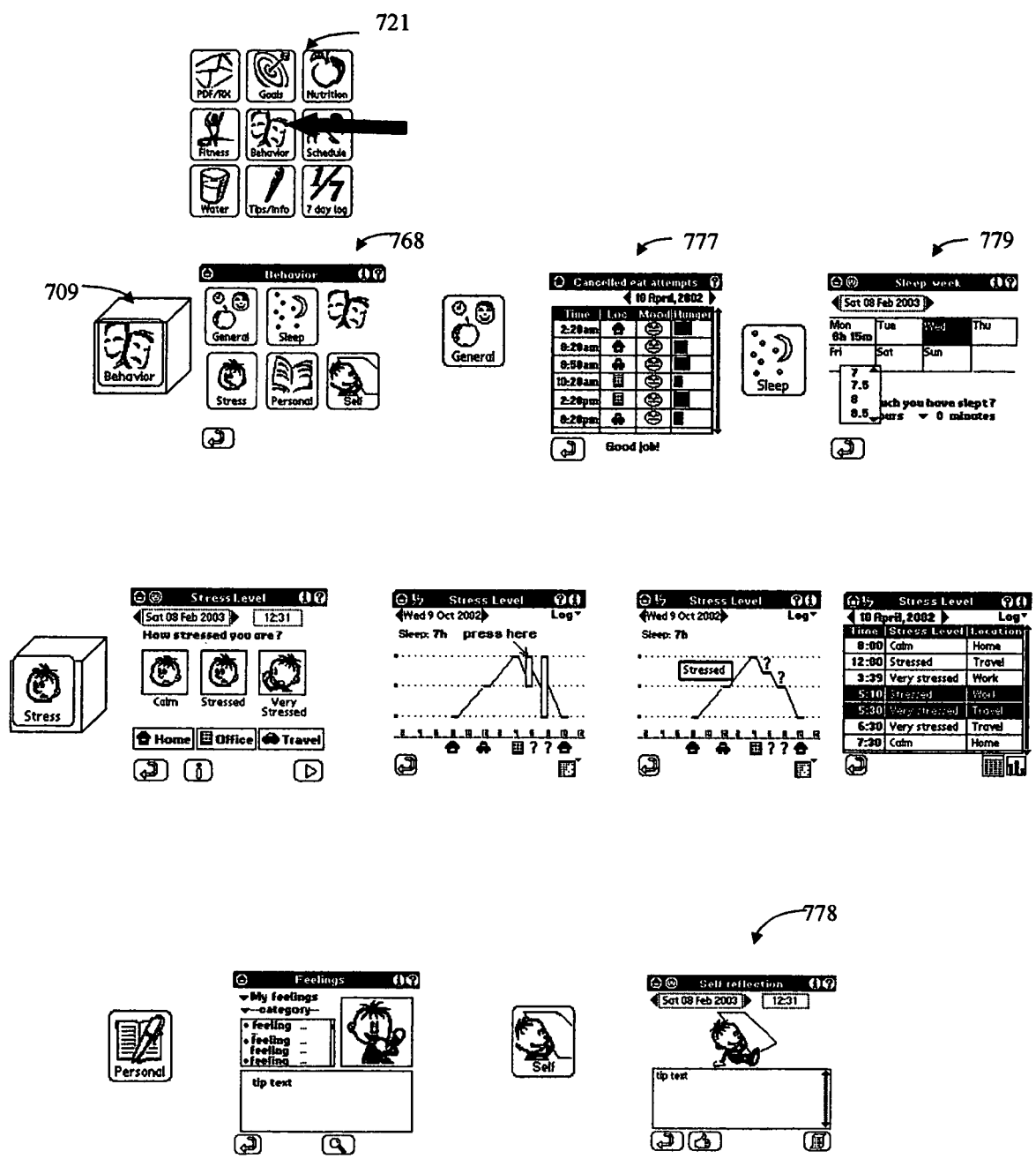
FIG. 14I includes exemplary personal device screen images illustrating the choice of the behavior button and the associated exemplary choices.
Figure 14J:
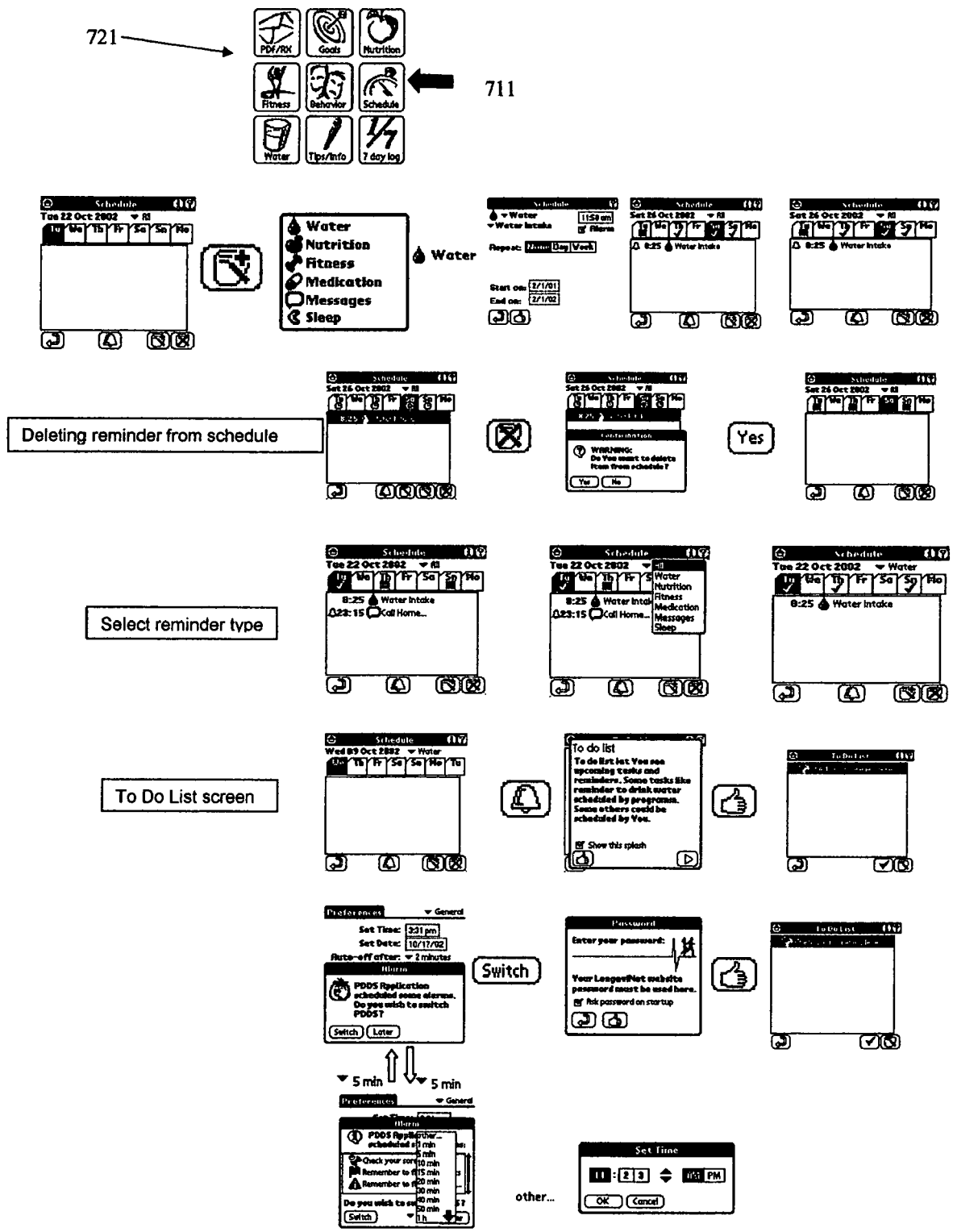
Figure 14K:
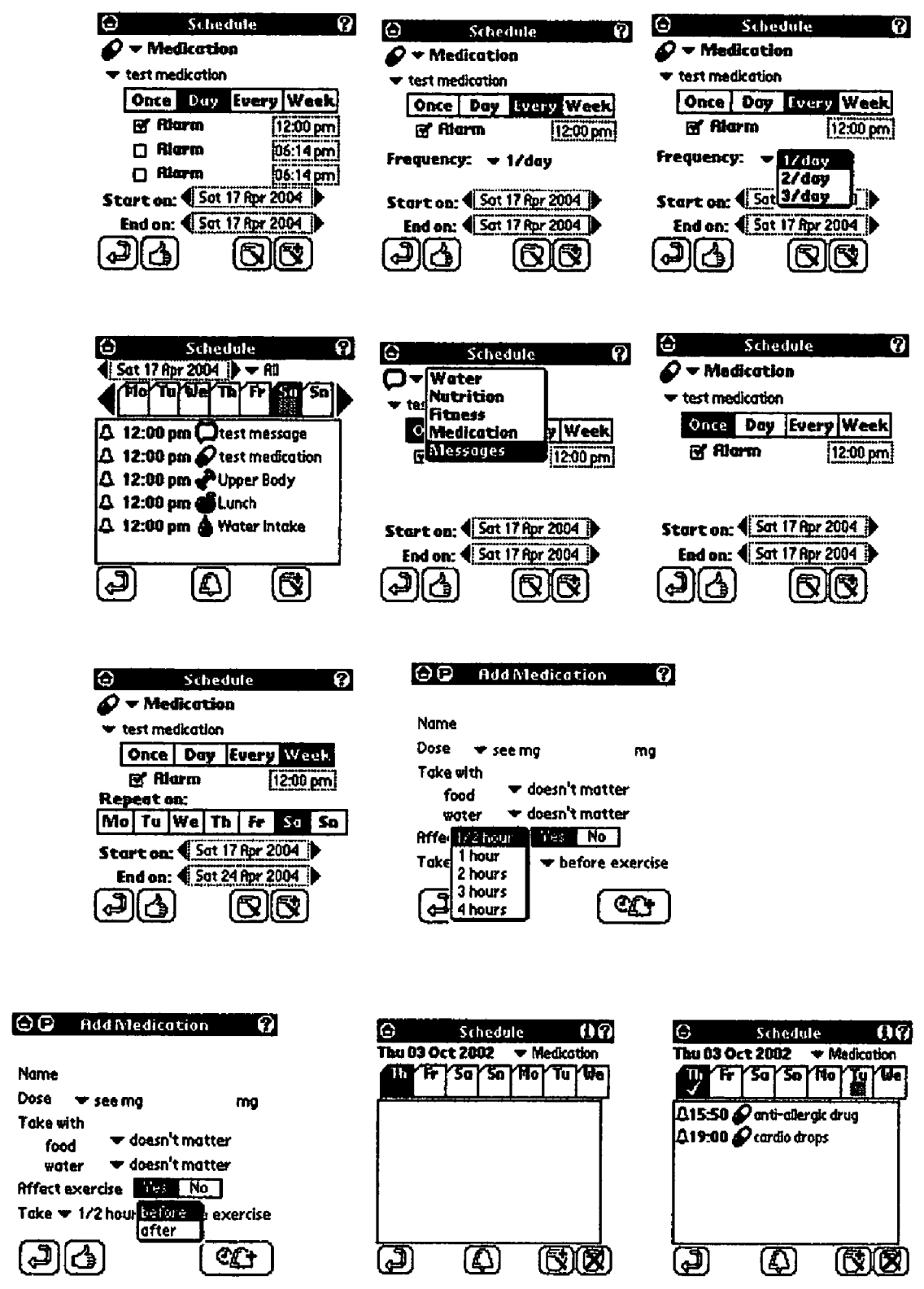
Figure 14L:
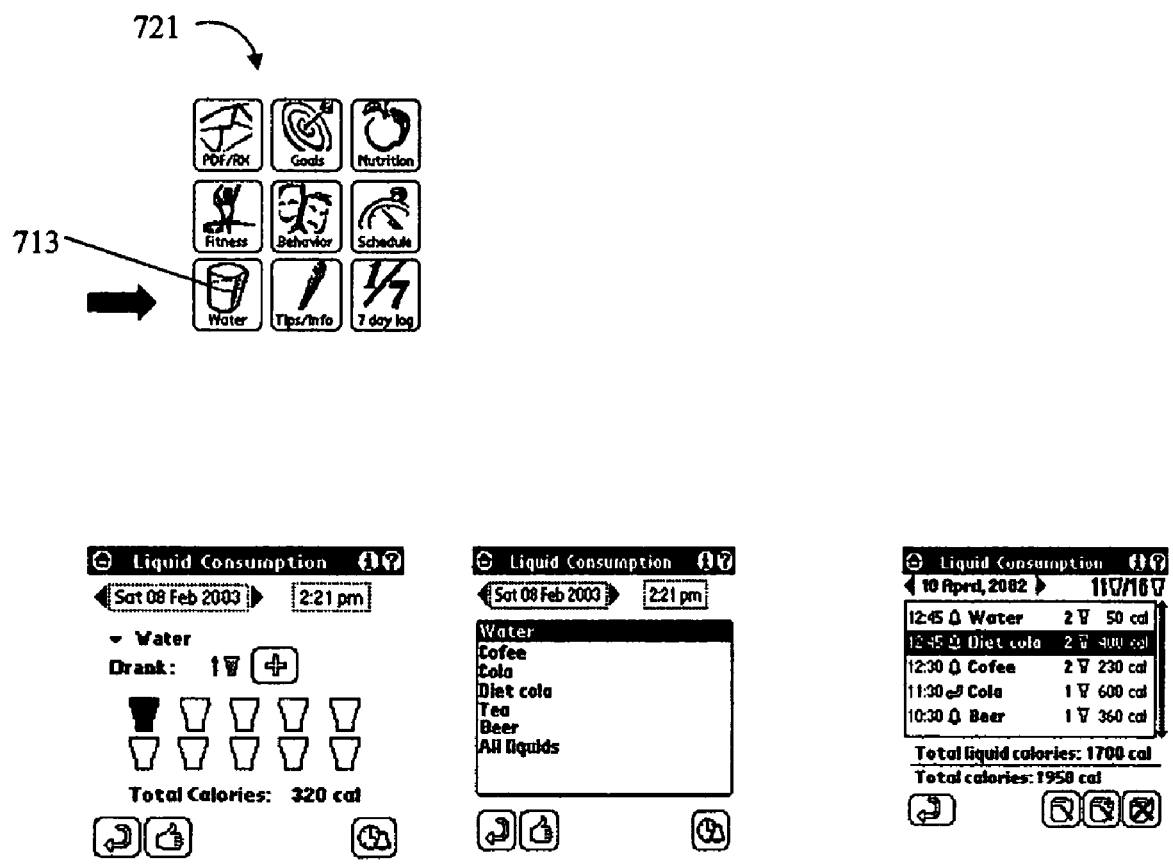
FIG. 14L includes exemplary personal device screen images illustrating the choice of the water button.
Figure 14M:
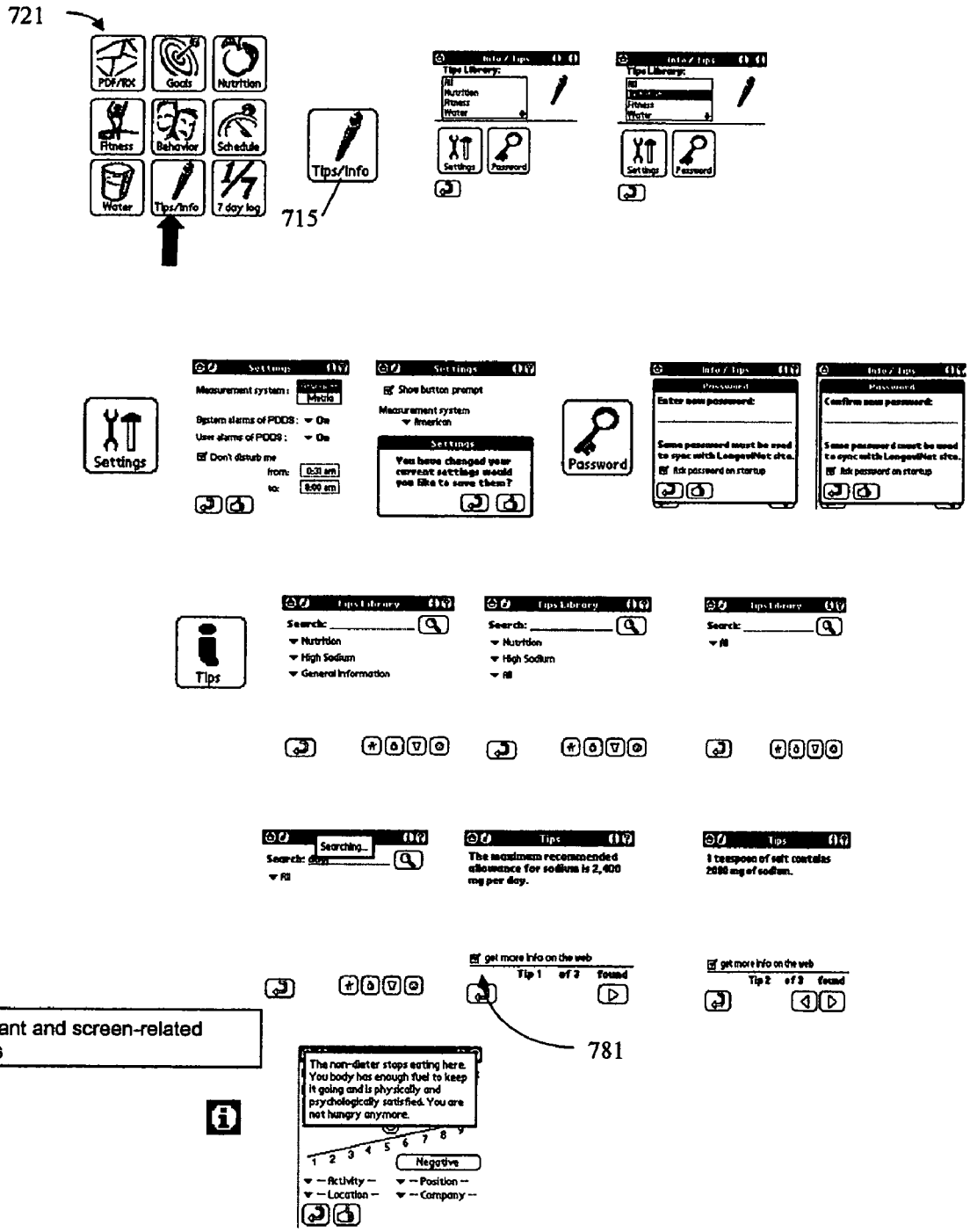
FIG. 14M includes exemplary personal device screen images illustrating the choice of the tips/info button and the associated exemplary choices.
Figure 14N:
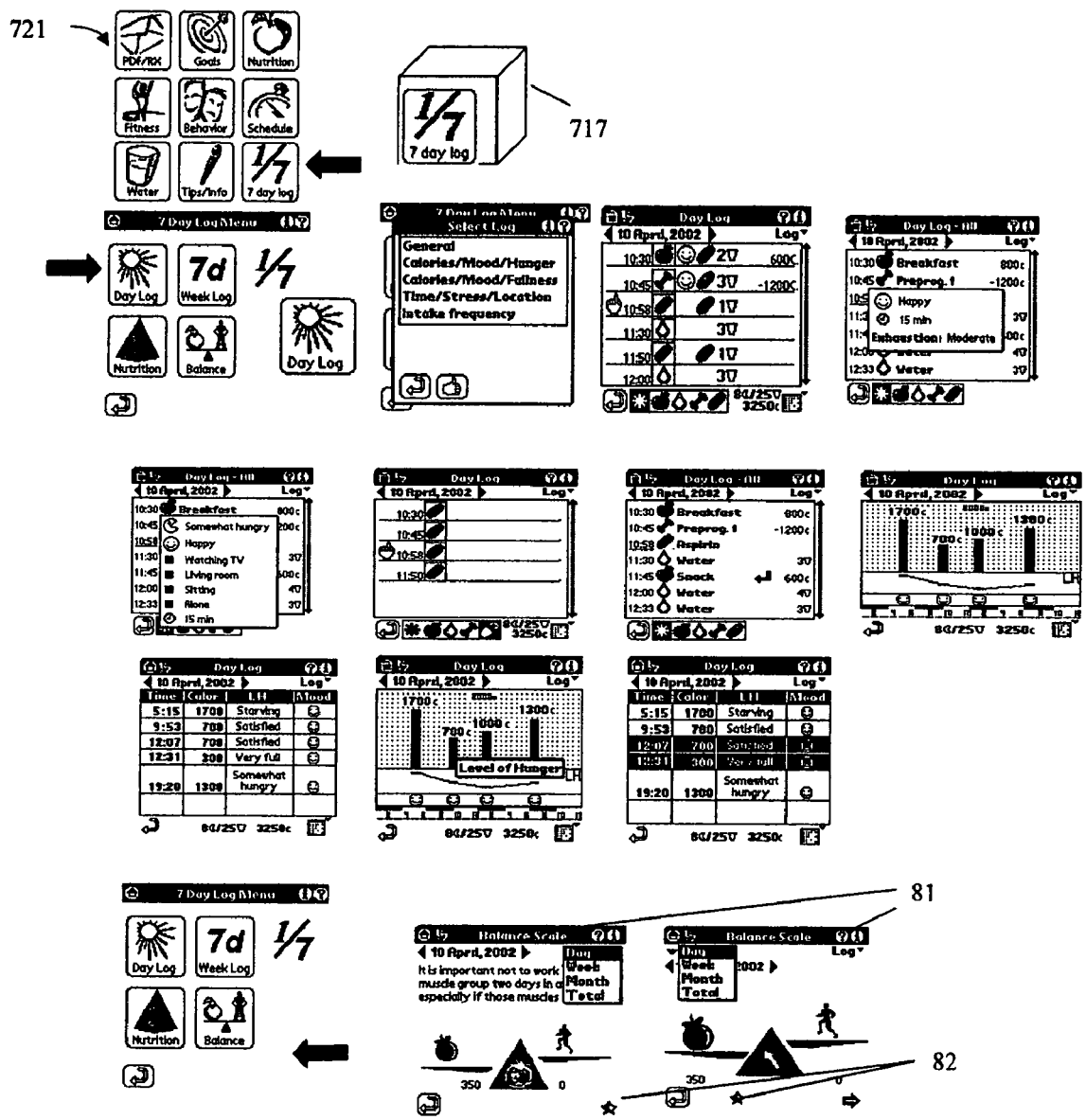
Figure 140:
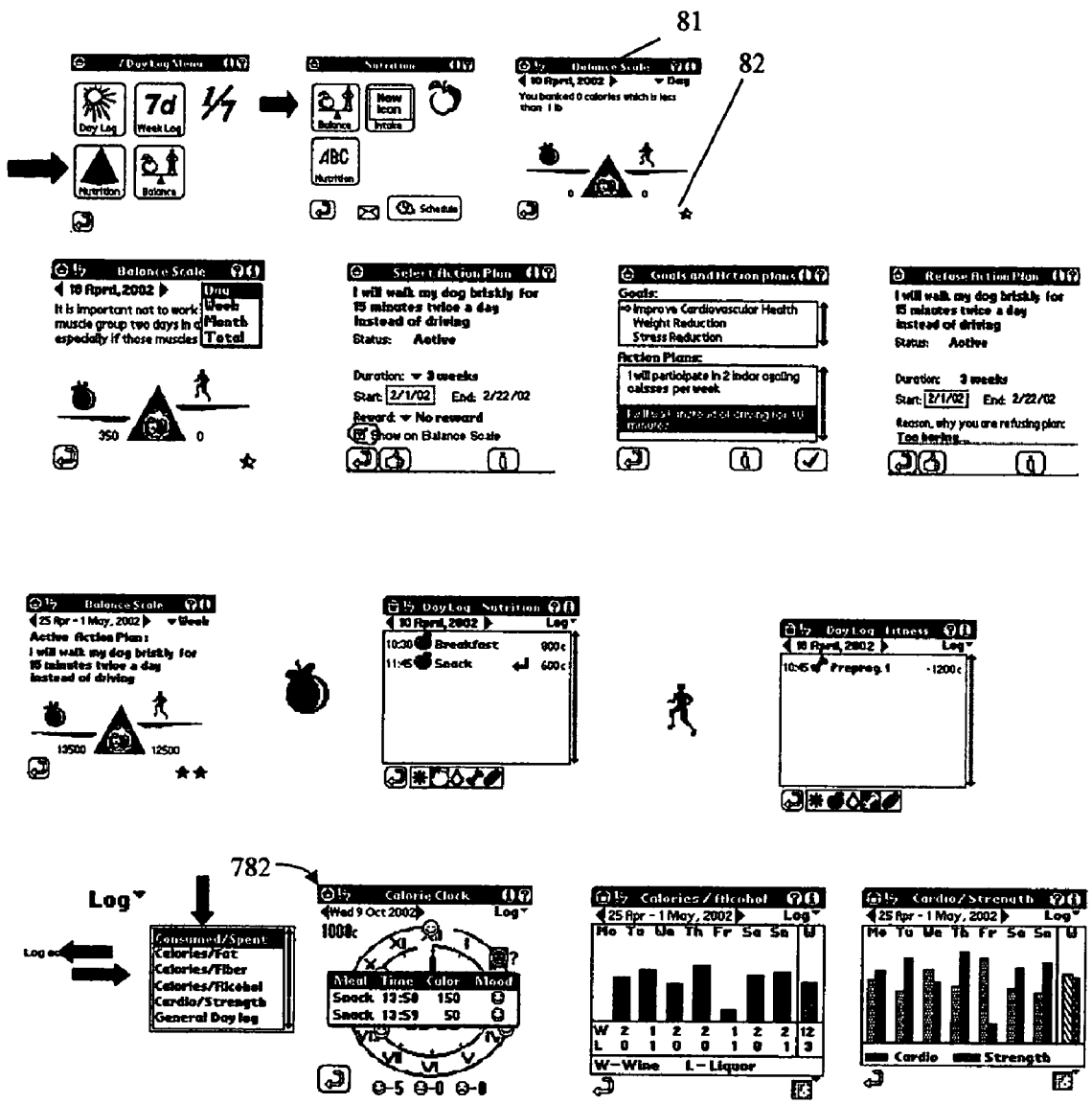
Figure 15A:
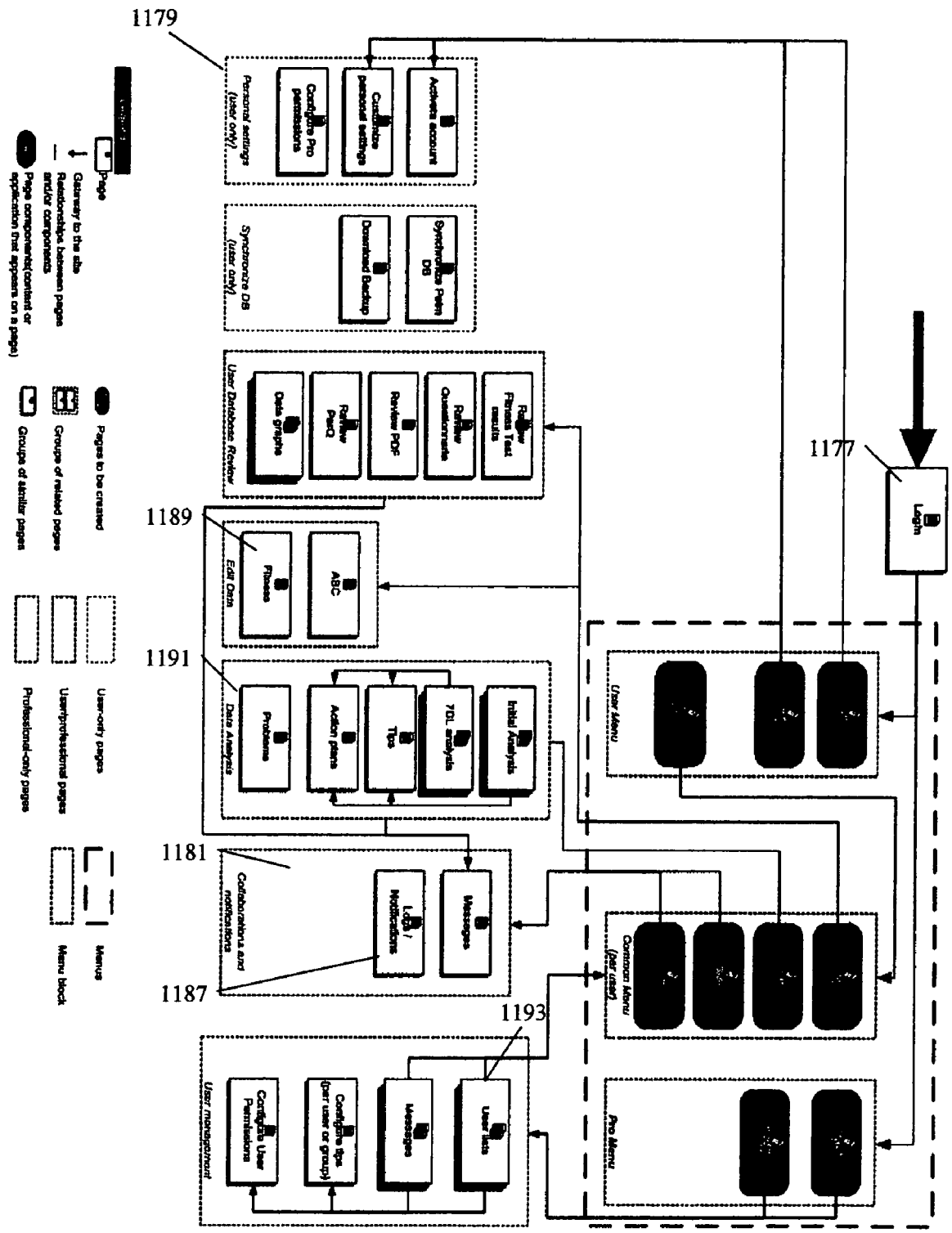
FIG. 15A is an block diagram of exemplary server screen groups categorized by users or professionals.
Figure 15B:
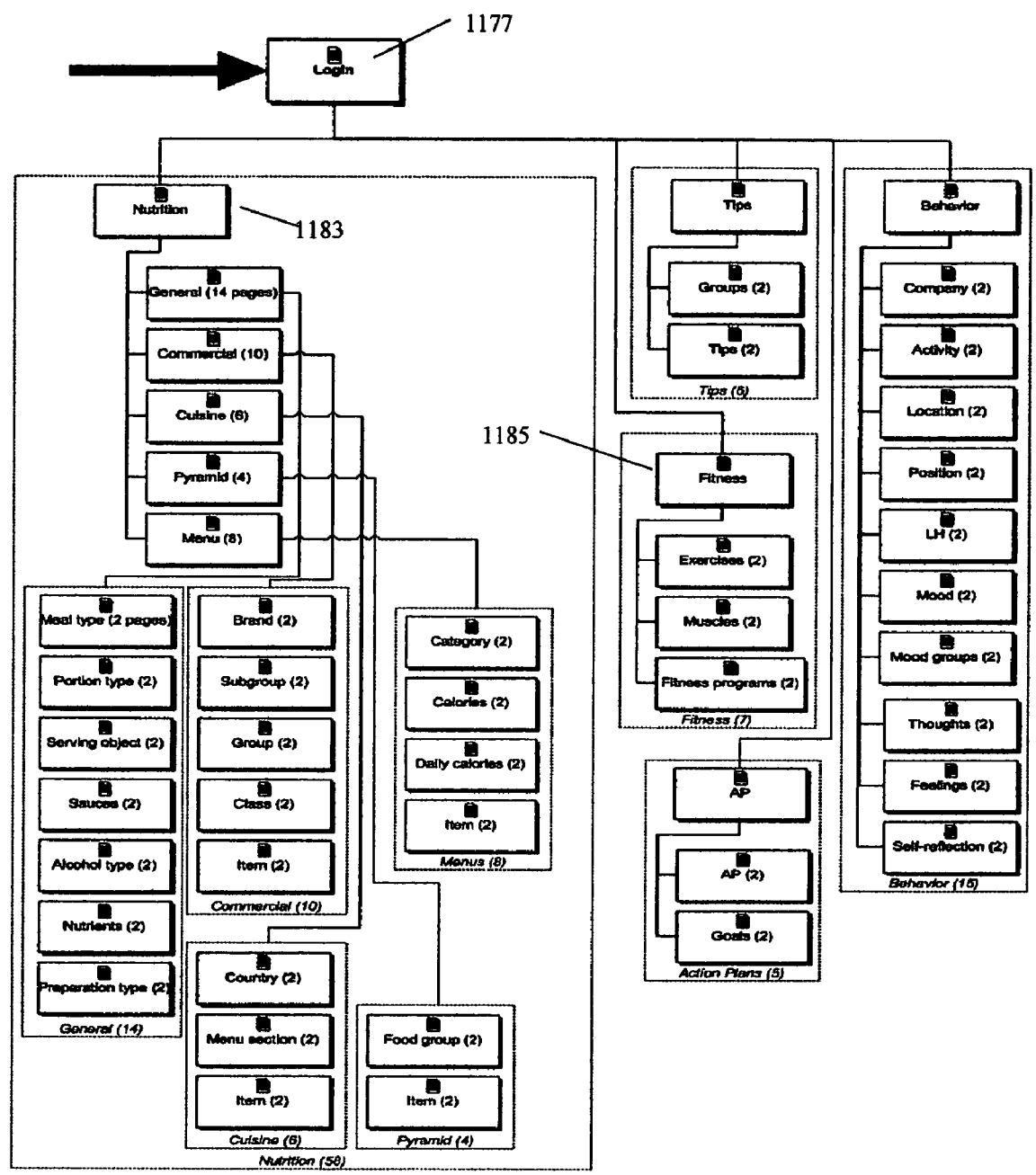
FIG. 15B is a block diagram of exemplary server screen groups categorized by topic.
Figure 15C:
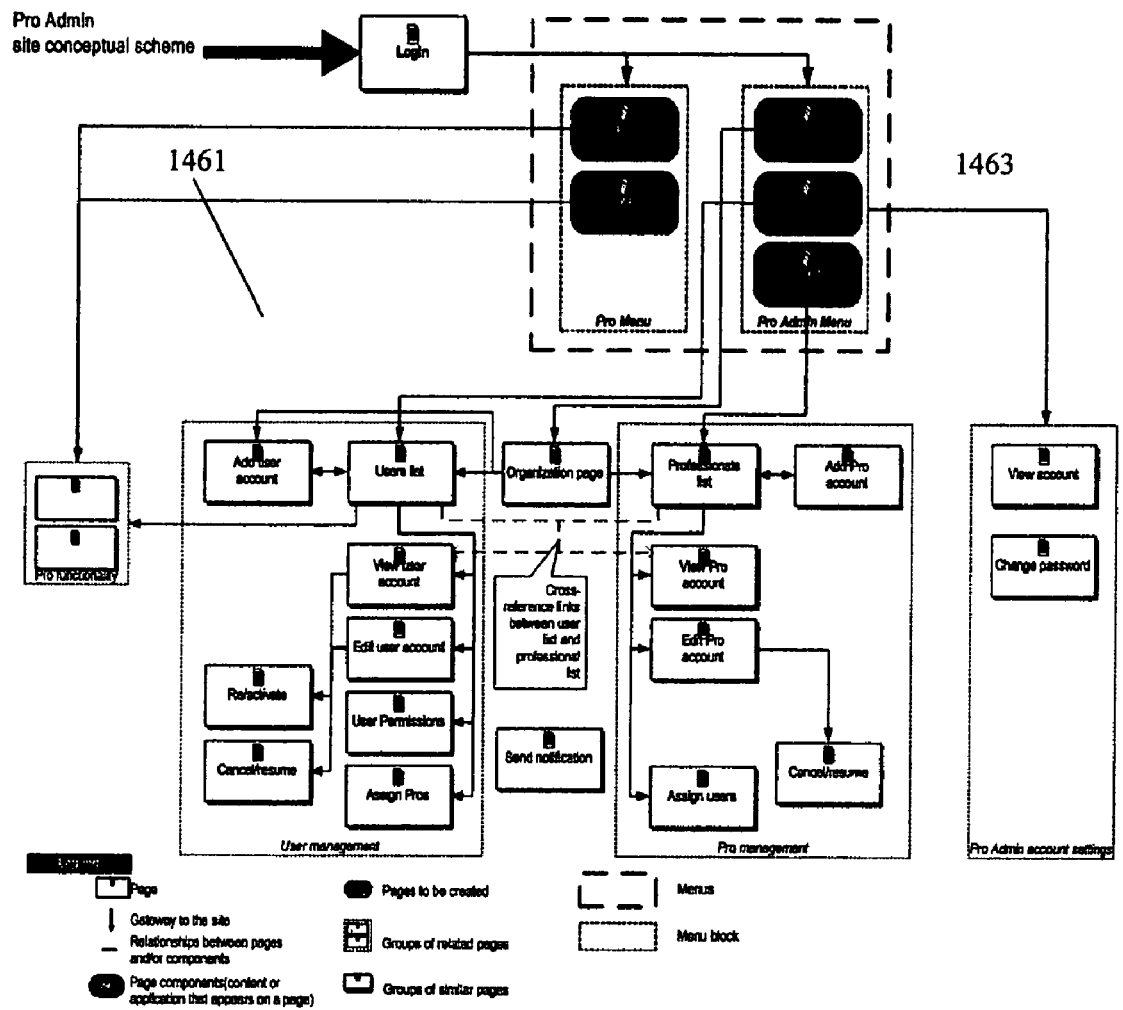
FIG. 15C is a block diagram of exemplary management screen categories of possible use to professionals.

FIGS. 14A-16K are illustrative screen images and categories of screen images that serve the user (FIGS. 14A-O, 15A-B, 15D-G, and 16A-K), the professional (FIGS. 15A-B and 15G-I), and the expert (FIG. 15C). FIGS. 14A-O present screen images that could appear on personal device 61 (FIG. 4A), while FIGS. 15A-I and 16A-K present screen images that could appear on server 65 that could be accessed through a website.

Referring now to FIGS. 14A/B, illustrative personal device buttons 721 (FIG. 14A) from which a user could choose are shown. Beginning the description of these buttons in the upper left-hand corner, the user may choose to enter personal and prescription data from PDF/RX button 701 (FIG. 14A). The user begins by entering a password, and is then shown Personal Data File (PDF) help screen 729 (FIG. 14A). The user can enter PDF data in, for example, four categories shown in PDF category screen 751 (FIG. 14A). Example screens from the general category are shown beginning with PDF constants 757 (FIG. 14A). The user can choose to enter medical data beginning with medical tests screen 733 (FIG. 14A). Medications that the user takes can be entered from prescription screens beginning with medication screen 725 (FIG. 14B). Importantly to the system of the present invention, the times that medications are due to be taken can be integrated within the system with the timing of other events, for example, eating, sleeping, and exercising. In this way, the system can remind the user to take medications at appropriate times, i.e. times at which the user isn't scheduled to be doing something else.

Referring now to FIG. 14C, entry test button 703 is chosen from illustrative personal device buttons 721, and the user is given a series of tests beginning with entry test introduction screen 758. After entry tests are complete, the user is instructed to synchronize with server 65 (FIG. 4A) in order that the entry test information may be analyzed more thoroughly according to the most up-to-date data and rules. Note that there can also be tests administered throughout the use of the system that collect information about the preferences of the user. Testing can be designed for different groups of users, so that entry and other tests can be part of the user-specific package.

Referring now to FIGS. 14D/E, nutrition button 705 (FIG. 14D) is chosen from illustrative personal device buttons 721 (FIG. 14D), and the user is presented with nutrition selection choices 759 (FIG. 14D). Shown illustratively in FIG. 14D are screens that could appear if the user selected the intake button. The system allows the user to specify a mood that is associated with the user's level of hunger. The system can relate the user's choices to other characteristics of the user in order to determine if the user's habits and behaviors coincide with indicators of certain types of behavior, for example, some forms of eating disorders. The system can provide nutrition guidance using the most up-to-date nutrition information that can be made available to the user during each synchronization cycle. The nutrition guidance can be based on, for example, the user's personal characteristics, medications, dietary restrictions, and weight goals as well. The user's nutrition information can be saved for later reference through nutrition save screen 761, and a notification 762 can be presented to the user after a user-determined amount of time. Nutrition can be broken down into its components as shown in ABC screen 771 (FIG. 14E). A user, system, or professional can determine, for example, the amount of calcium the user needs to consume over a period of time and help the user to adjust food intake, exercise, and medications, for example, to achieve that goal. Mail screen 780 (FIG. 14D) can be used to send and receive e-mail from, for example, a restaurant or a professional. The system can automatically send e-mail to the user between synchronizations to update the user on any analysis, including, for example, professional analysis, or other changes to relevant user-specific data.

Referring now to FIGS. 14F-H, fitness button 707 (FIG. 14F) can be chosen from illustrative personal device buttons 721 (FIG. 14F), and the user can be presented with fitness testing screens (see FIG. 14F), if testing is selected from the possible fitness choices 763 (FIG. 14F). Shown illustratively are screens that show a selection of steps of a bench press test. The user can choose to see results 764 (FIG. 14F) of the fitness tests. After the completion of the fitness test, the user can measure her physical response to exercise including, for example, her pulse. The system can, if requested, illustrate the correct procedure for measuring pulse rate. The user can also be presented with possible exercises as shown illustratively in fitness database selection screen 765 (FIG. 14G), which allows the user to choose among various types of exercises. From this series of screens, the system can present information about possible exercises from which the user can choose to create a personal workout plan. The information can include, for example, the number of repetitions required to meet certain fitness goals and how the exercise is done. To complement the user's choice of certain exercises, the user can establish a certain times at which the chosen exercises should be performed through exercise scheduling screen 767 (FIG. 14H) and succeeding screens.

Referring now to FIG. 14I, behavior button 709 can be chosen from illustrative personal device buttons 721, and the user can be presented with one of several possibilities depending on the user's selection from behavior selection buttons 768. Shown are possible mood, sleep, stress, personal, and self-reflection example screens. The user is able, through these screens, to provide to the system the user's emotional characteristics. These characteristics are integral to analyzing the user's behavior with respect to indicators of certain types of behavior known to the system. The user is also able to see a graphic time-based progression of characteristics such as, for example, stress level. Visual feedback screen 777 provides an example of one of the visual feedback of a user's specific behavior pattern. Auto screen 778 provides automatic user-specific feedback for behavior based on personal characteristics such as, for example, gender, age, temperament, etc. (see FIG. 8D). Sleep screen 779 illustrates information about the sleeping behaviors of the user. In general, the system can relate certain behaviors to other behaviors, such as, for example, the amount of sleep to a caloric intake profile. The system can produce specialized tips to help the user realize these possible connections. These concepts can apply to stress-related behaviors.

Referring now to FIGS. 14J/K, schedule button 711 (FIG. 14J) can be chosen from illustrative personal device buttons 721 (FIG. 14J), and the user can be presented with one of several possible scheduling actions. The user can set a schedule of food and water intake, exercise, medications, reminders, and sleep. The user can maintain the schedule by adding and deleting items, and can customize schedule reminders.

Referring now to FIG. 14L, water button 713 can be chosen from illustrative personal device buttons 721, and the user can indicate liquid consumption to the system. In return, the system can provide the user with the number of calories, for example, the user has consumed from consumed liquids.

Referring now to FIG. 14M, tips/info button 715 can be chosen from illustrative personal device buttons 721, and the user can be presented with one of several possible libraries of dynamically updated tips and information from which to choose. Through these screens, the user may also change personal device settings, alarm settings, and security information such as password. Examples of general and user-specific tips are given, including the timely instant tips that can relate to an activity that the user is currently engaged in, such as eating. Checked selection 781 allows the user to request information that can be provided when the user is ready to review the requested information.

Referring now to FIGS. 14N/O, 7-day-log button 717 (FIG. 14N) can be chosen from illustrative personal device buttons 721 (FIG. 14N), and the user can be presented with, for example, daily logs, weekly logs, nutrition, and balance scale information. The logs contain information about what the user has done and any analysis that might be appropriate to present to the user. Balance scale 81 (FIGS. 14N/O) and star system 82 (FIGS. 14N/O) have been described previously. Depression of the nutrition button (FIG. 14O) presents to the user balance scale, intake, and nutrition details. In particular, balance scale graphics are shown for nutrition and exercise selections. Also, scheduled goals and action plans can be reviewed. Calorie clock 782 (FIG. 14O) is another example of visual feedback of a user's specific behavior pattern.

With respect to the professional and the user, and referring now to FIGS. 15A and 15B, categories of screen images are shown. FIG. 15A illustrates a grouping of categories of screen by functionality, for example, 7-day-log, analyzed data, database review, etc. At the top, operationally and in FIG. 15A, is login screen 1177, and from there, the user can choose the personal category screens 1179 to enter personal data, among other things. After passing through certain menu choices, the user or professional may choose to edit fitness data through fitness data screen 1189, or either could view the status of the user's indicated behavior through problems screen 1191. Professional collaboration can be enabled through a group of collaboration screens 1181, of which logs/motivations screens 1187 are a part. The professional can manage a group of patients through user management screens, of which user lists screens 1193 are a part.

FIG. 15B illustrates a grouping data collection, analysis, and feedback categories. With respect to functionalities, the user or professional could select a login screen 1177, such as the illustrative screen of FIG. 16A. The user or professional could choose to, for example, view the nutrition category screens 1183, or the fitness category screens 1185.

Referring now to FIG. 15C, the expert screen categories illustrate the types of actions that an expert would normally take with respect to the system of the present invention, with the aid of software, processes, hardware, etc., that implement expert 14 (FIG. 1B). As shown in FIG. 15C, the expert can add user accounts 1461 and add professional accounts 1463, as well as manage those accounts. Not shown is the capability of the expert to make modifications to system data, the integrity of which is insured by the system of the present invention across the system including personal devices 61 (FIG. 4A) and server 65 (FIG. 4A).

Figure 15D:
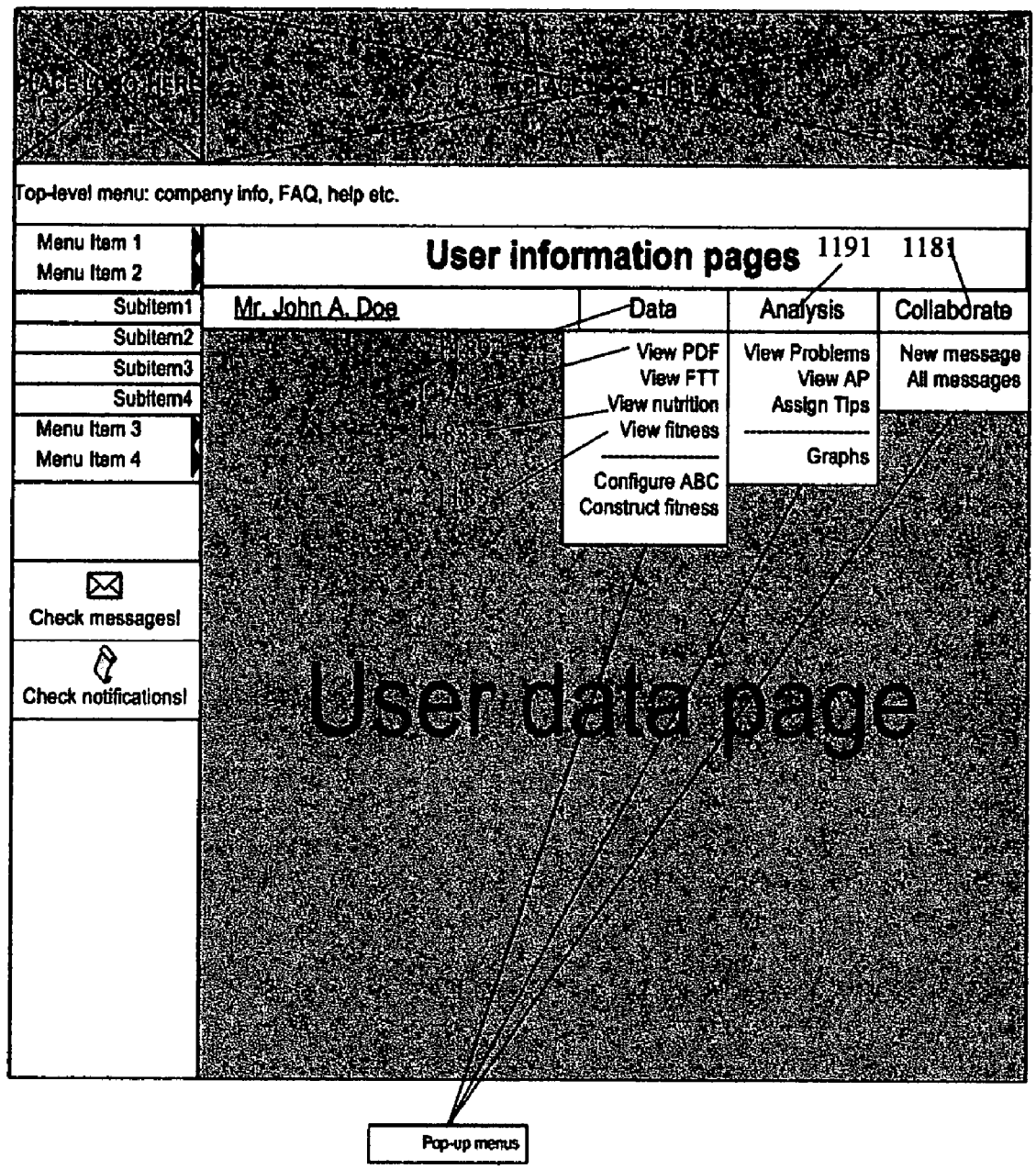
FIG. 15D is an exemplary server screen image illustrating a possible user information page layout.
Figure 16A:
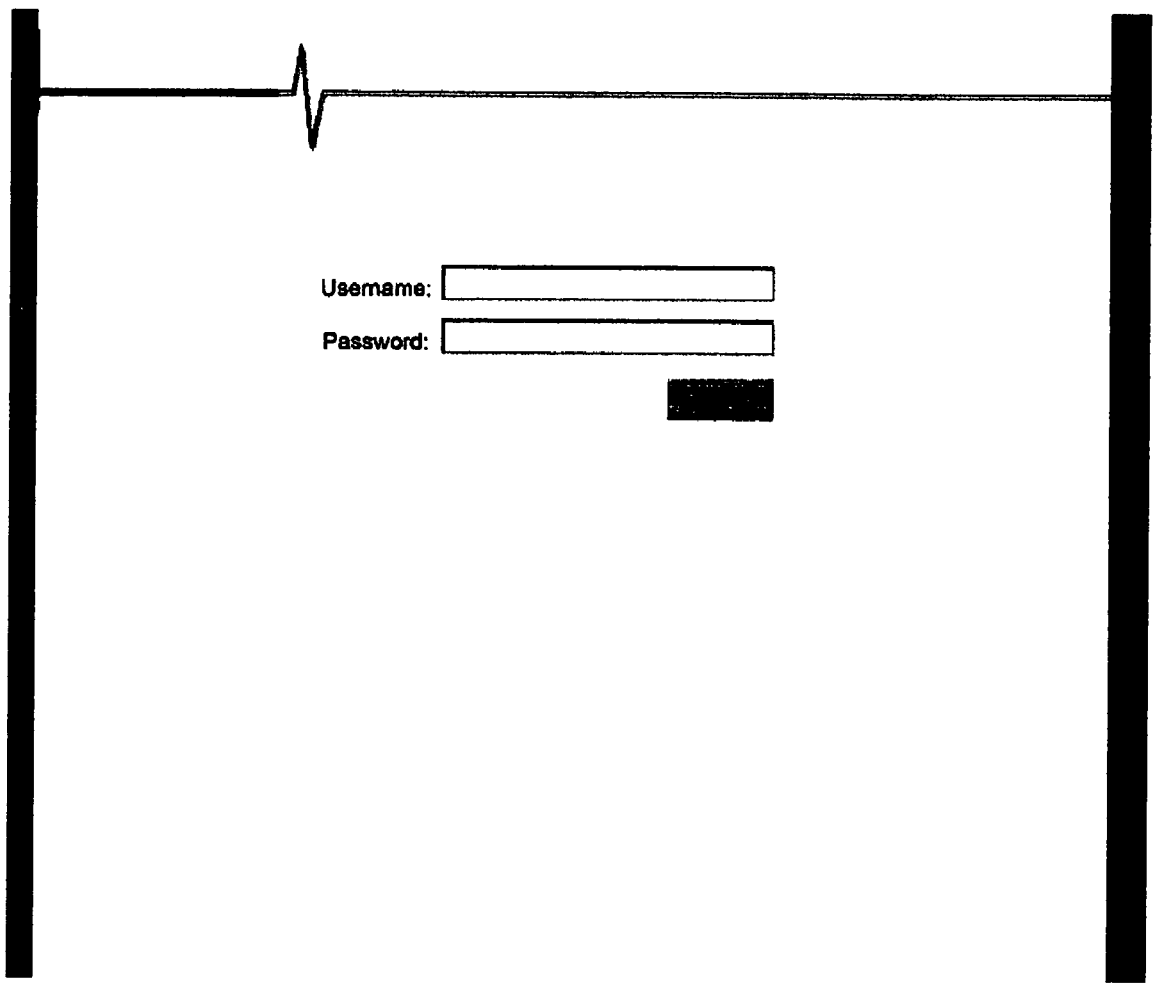
FIG. 16A is a screen image of an exemplary server login screen.

Referring now to FIG. 15D, to invoke screens that are part of the categories presented in FIGs. 15A/B, the user could, upon login to the server through the illustrative screen of FIG. 16A, be presented with the illustrative screen of FIG. 15D. From the screen, the user could pull down menus from categories including, but not limited to, data screens 1189, analysis screens 1191, and collaboration screens 1181. From the data screens 1189 pull down, the user could view personal category screens 1179 (also known as PDF), nutrition category screens 1183, or fitness category screens 1185, to name a few possibilities.

Referring now to FIGS. 15E/F, the user can customize a workout schedule from server 65 (FIG. 4A) to augment or replace what the user has scheduled using screens illustrated in FIGS. 14F/G. The user would access server 65 to, for example, have access to more resources when designing an exercise program.

Referring now to FIG. 15G, both a user and a professional with access can track the user's progress against identified behavior types. From a screen such as FIG. 15G, the user and the professional can view analysis of all behaviors, for example, at points in time when the behavior is initially diagnosed, when the behavior state changes (problem/possible problem/no problem), and when the behavior is modified. From a screen such as the one shown, the user can show/hide information about sub-behaviors and action plans related to each behavior by clicking the "+" button 774 next to the behavior name. If the behavior has "no problem" status (see FIGS. 13A-D), it can be displayed in a separate table as shown.

Referring now to FIG. 15H, the professional can view a list of all assigned patients. As can be seen from the illustrative screens of FIG. 15H, different sorting and filtering options are available to the professional such as, for example, sorting by name and dates, and sorting by behavior. User detail can be viewed from each entry in the table shown.

Figure 15I:
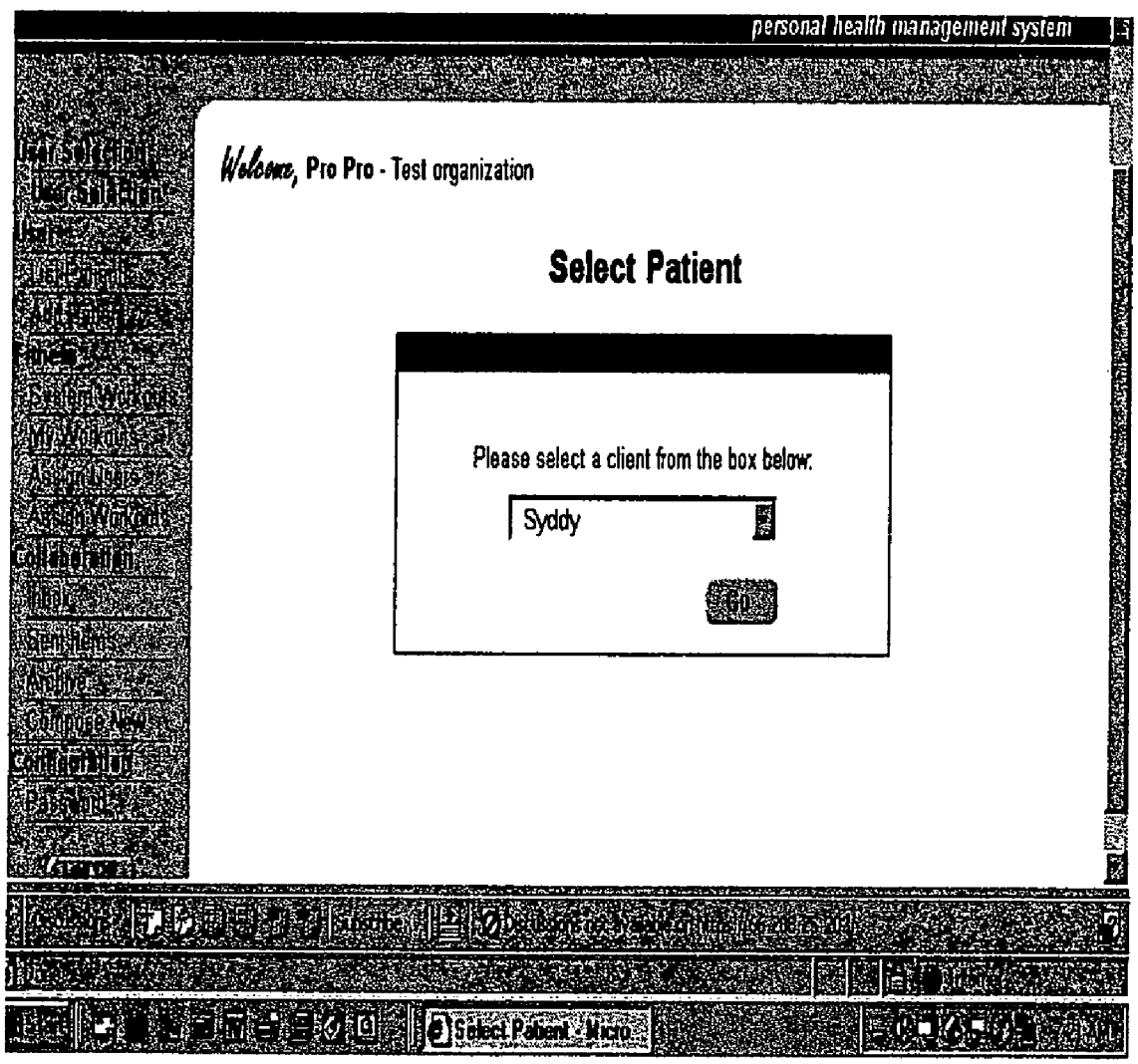
FIG. 15I is a screen illustrating, on the left, possible options a professional might have for managing patient care.

Referring now to FIG. 15I, the professional can direct the system to perform a variety of functions, as previously discussed. The left column of FIG. 15I illustrates an exemplary set of functions that the professional could direct the system to perform. Functions such as listing patients (according to filters as described with respect to FIG. 15H), adding patients, setting up fitness schedules, and collaborating with the patient (user) and other professionals are examples of activities that a professional could engage in on behalf of the user.

In addition to the server screens shown in FIGS. 15A/B and 15D-G that are available to the user and/or professional on server 65 (FIG. 4A), the user and/or professional may also access screens such as those shown illustratively in FIGS. 16A-K. FIG. 16A is the exemplary server login screen referred to previously.

Referring now to FIG. 16B, the user and/or professional can choose to view and modify statistics from the PDF information that had been collected using screens shown in FIG. 14A and others. Pro marker 776 indicates that a professional may comment on this particular characteristic, as is shown on FIG. 16B.

Figure 16C:
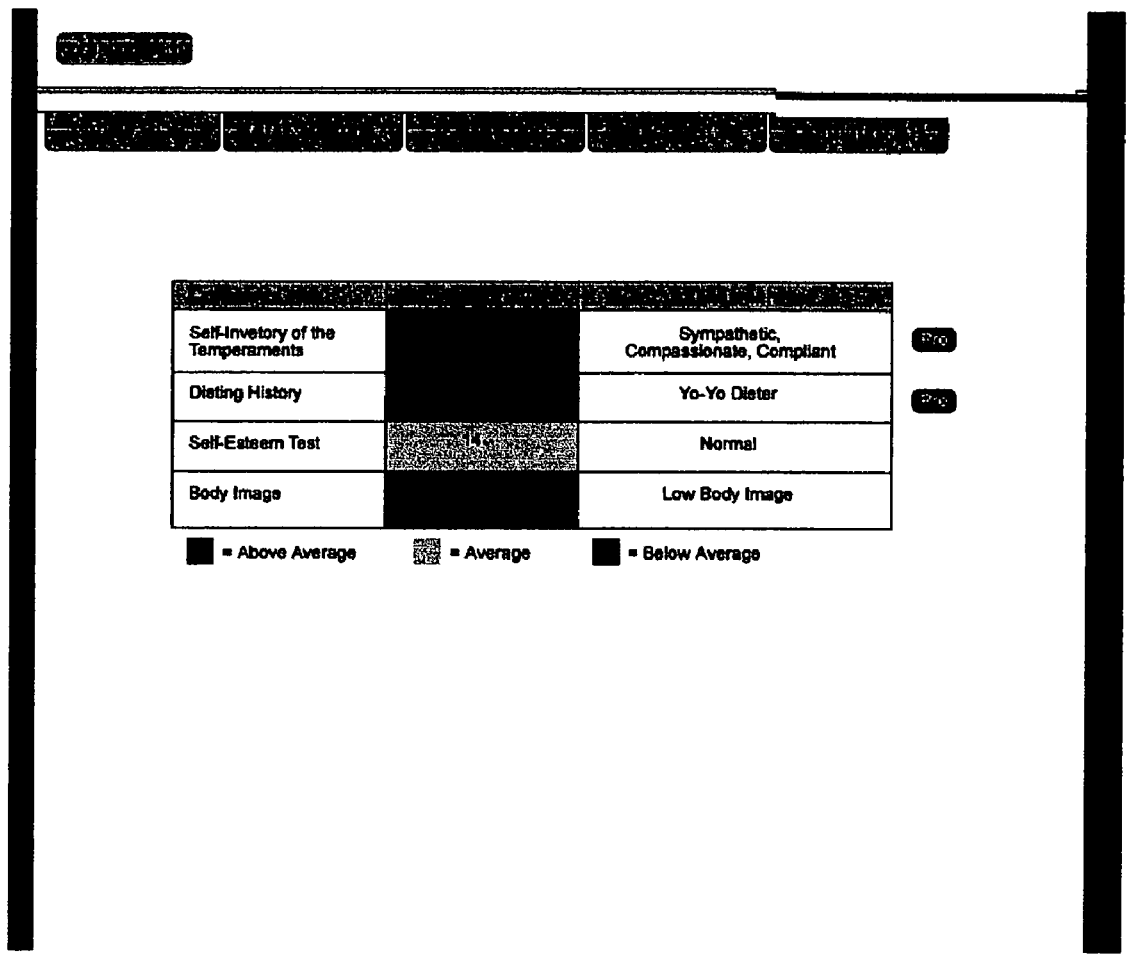
FIG. 16C is a screen image of an exemplary server screen used to report comparative personal data and present collaboration results.

Referring now to FIG. 16C, shown here is an assignment of "score" to a user's characteristics, including behavioral, physical, and emotional, including professional assessment where possible. These numerical and textual assessments can be used by the system to prepare analyses of the user's progress with respect to the user's identified behaviors. These screens, assessments, etc., can be dynamically updated as data are continuously gathered from the user, as they are analyzed by the system, and as the professional uses tools available through the system to evaluate progress and provide assistance to the user.

Figure 16D:
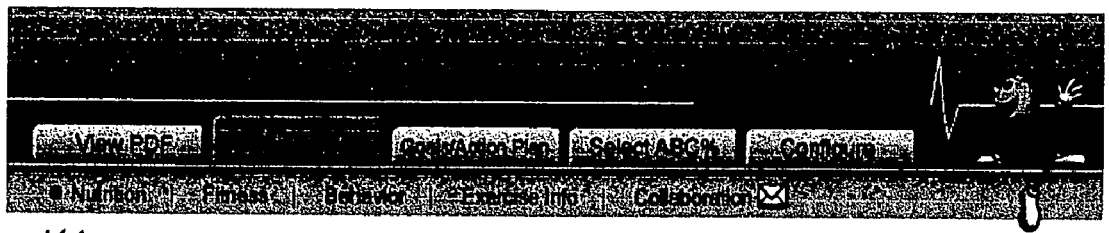
FIG. 16D is a screen image of an exemplary server screen used to present 7-day-log daily nutrition information.
Figure 16E:
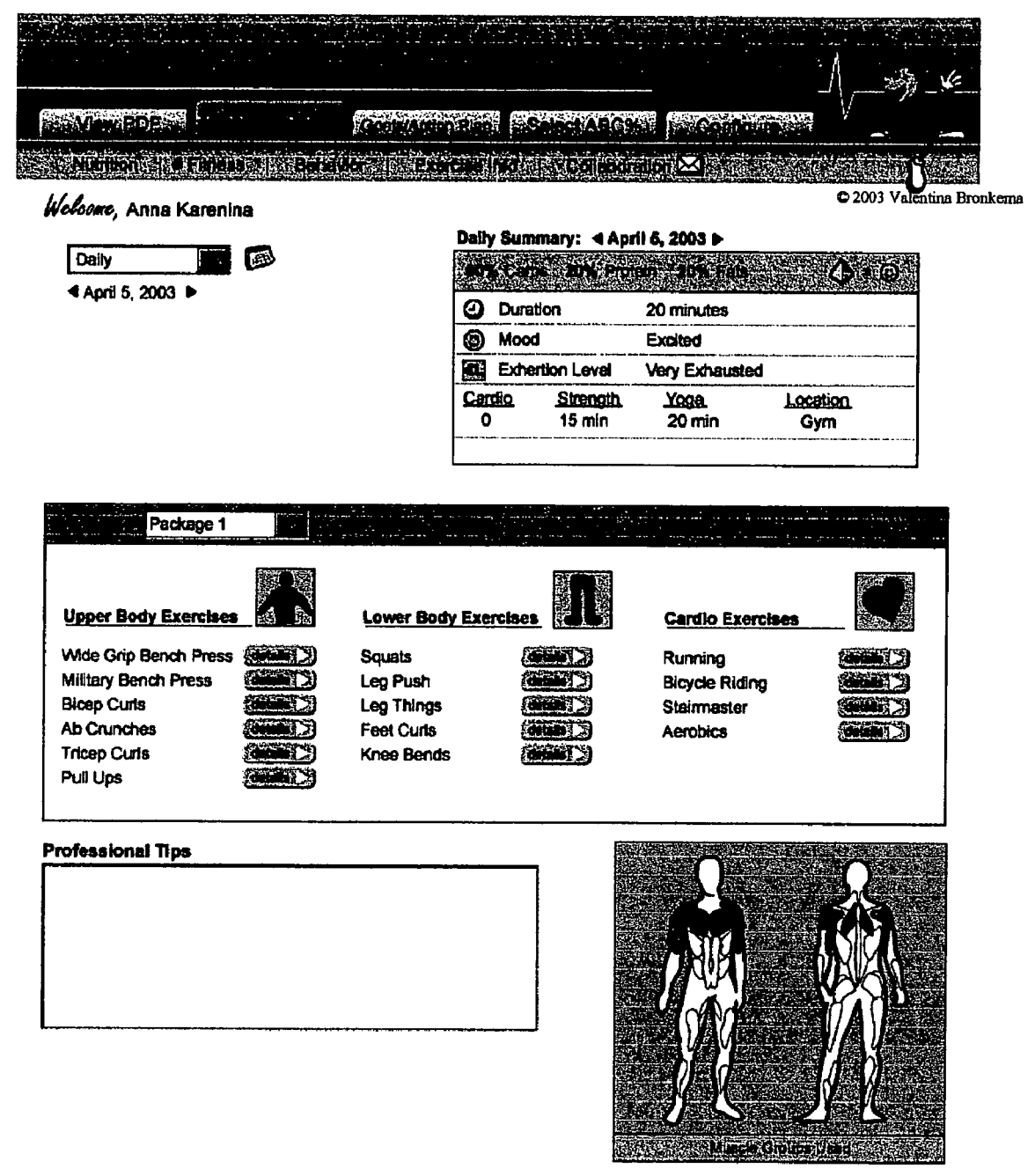

Referring now to FIGS. 16D/E, the user and/or professional may choose to view the 7-day-log from server 61 (FIG. 4A) over, for example, daily, weekly, or monthly time periods. The screen shown in FIG. 16D illustrates a daily summary of the 7-day-log data. In particular, a user and/or professional may inspect daily solid and liquid intake by calories and essential nutrients, any medications taken over the time period, and any exercise performed. These data can be displayed in chronological order, and with associated behavior and location, as well (FIG. 16D). Also a detailed breakdown of the muscles exercised, including graphic illustrations, can be provided (FIG. 16E).

Figure 16F:
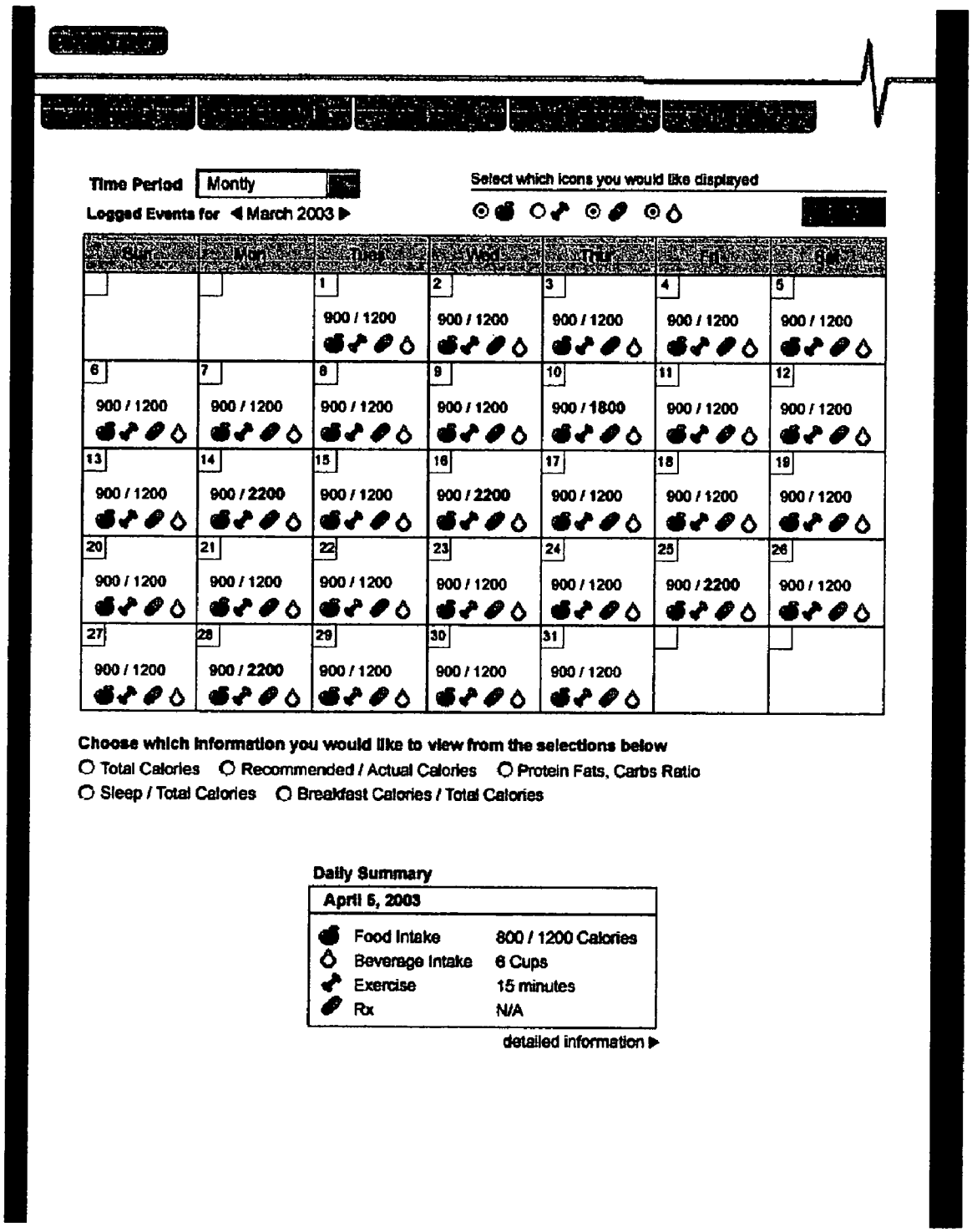
FIG. 16F is a screen image of an exemplary server screen used to present monthly logged information.

Referring now to FIG. 16F, a summary over an entire month can be provided to the user and/or professional, and the user and/or professional may select how the data are to be displayed, for example, by nutrition, fitness, medications, or beverage intake. A particular day may be selected, and the screens displayed in FIGS. 16D/E may be displayed for that day.

Figure 16H:
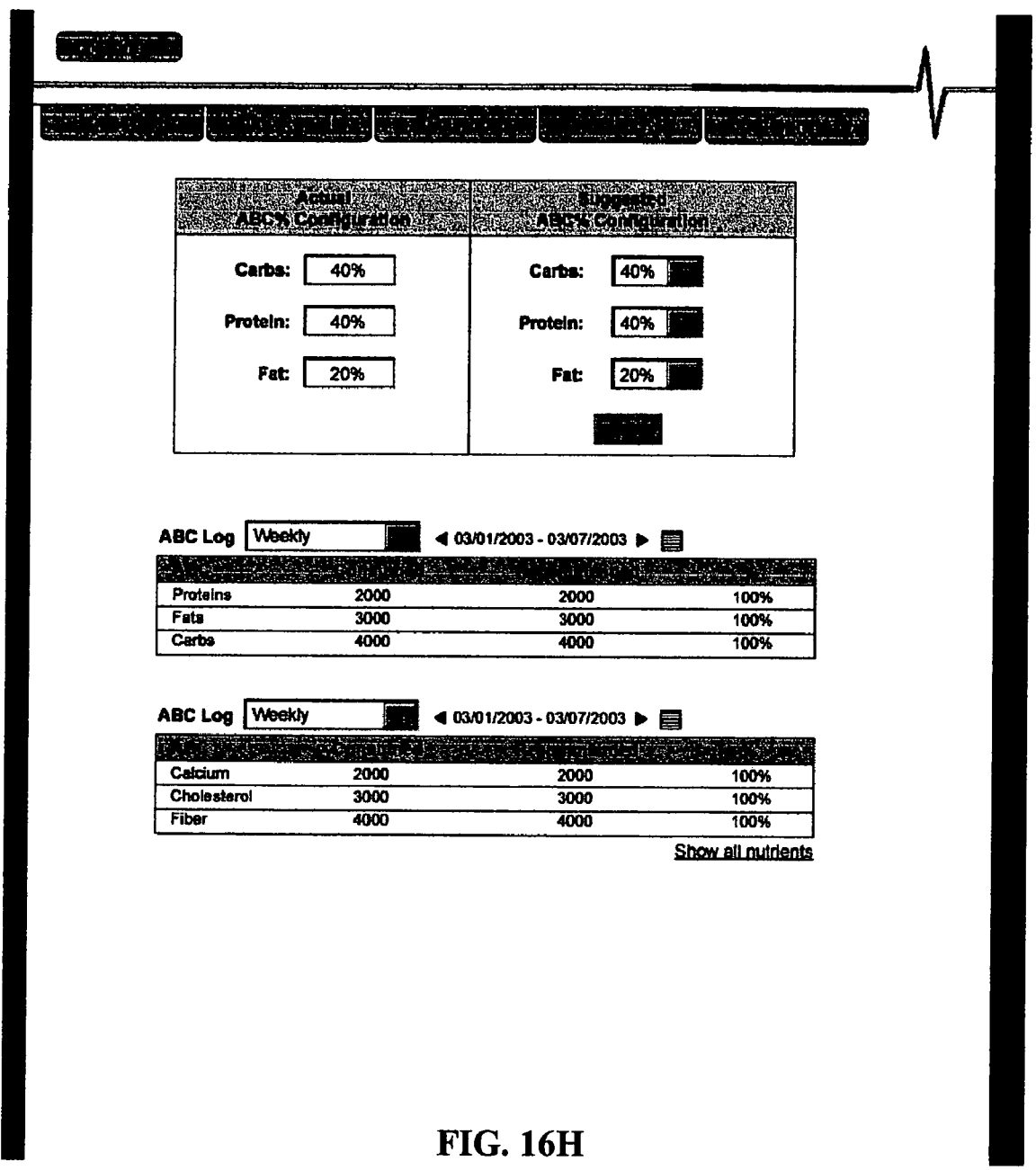
FIG. 16H is a screen image of an exemplary server screen used to present weekly logged nutrient consumption information.

Referring now to FIGS. 16G/I, weekly summary data can be provided. Further, the user and/or professional may filter according to days during the period in which exercise was performed for a selected amount of time or days on which a certain mood prevailed, for example (FIG. 16G). Note that the possibilities for filtering the data are not limited by the examples provided here. The user may view how actual food intake compared to suggested intake, as broken down by categories of nutrients, for example (FIG. 16H). These data can be broken down by micronutrients as shown in FIG. 16I. The user and/or professional may select a particular micronutrient to increase or decrease, depending on a user's particular needs, even if the overall nutrient balance is recommended otherwise by the system or the professional.

Figure 16J:
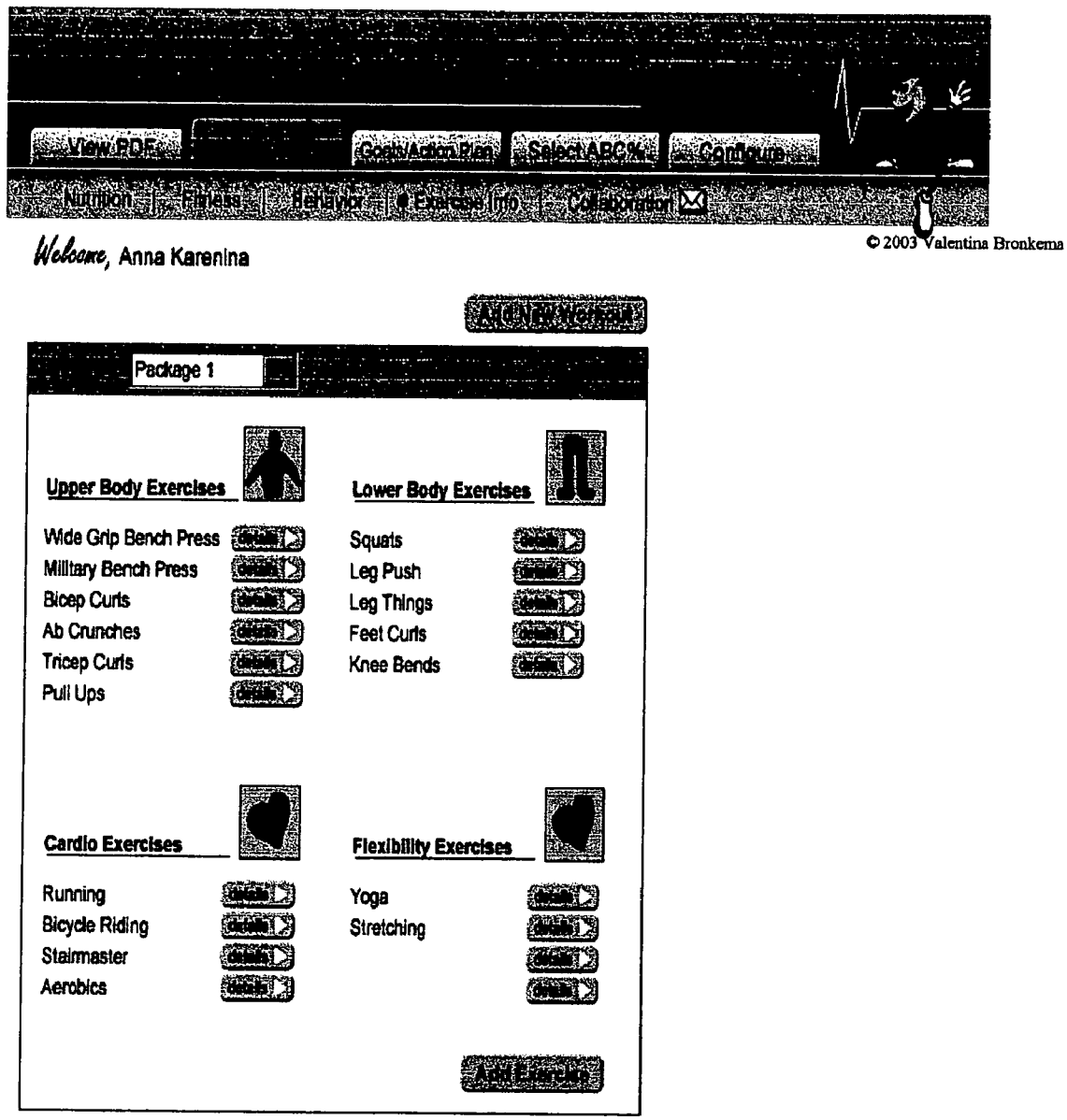
FIG. 16J is a screen image of an exemplary server screen used to create a new entry in a personal fitness package.
Figure 16K:
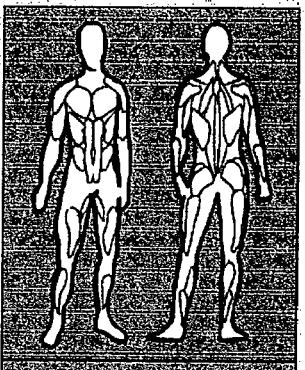
FIG. 16K is a screen image of an exemplary server screen used to present exemplary selection choices for adding new exercises to a fitness routine.

Referring now to FIGS. 16J/K, the user and/or professional may add, for example, workout regimes to a user's possible fitness inventory. As shown in FIG. 16J, the plan can include upper and lower body exercises, cardio or flexibility exercises, as selected. Alternatively, as shown in FIG. 16K, the system could assist in designing an exercise regime by providing a graphic selection aid to choose particular muscles or muscle groups to exercise. The user and/or professional can select a particular exercise as well to add to the exercise regime.

Although the invention has been described with respect to various methods and embodiments, it should be realized this invention is also capable of a wide variety of further and other methods and embodiments suitable for further and other purposes, all within the scope of the present invention.

What is claimed is:

1. A system having computer memory containing instructions for implementing behavior modification of a user comprising:
    a data collector subsystem configured to receive computer-readable user-specific information from sources;
    a package designer subsystem, said package designer subsystem configured to
        automatically access pre-selected problem-identification rules that are linked to behavior problems;
        automatically determine at least one behavior problem associated with the user based on said problem-identification rules and said user-specific information;
        provide an electronic user-specific package including said user-specific information, said at least one behavior problem, and a user-specific program including recommendations and action plans that are uniquely derived for the user based on the at least on behavior problem and the user-specific information; and
    a feedback provider subsystem configured to present electronic feedback to the user based on said user-specific program, including recommendations, integrated and dynamically changing action plans, tips, monitoring, and compliance advisories;
    wherein said data collector subsystem receives updated user-specific information from the user after the user has reviewed said electronic feedback, and wherein said package designer processes the updated user-specific information to update said user-specific package and said user-specific program indicating that the user has modified said at least one behavior problem based upon said electronic feedback.

2. The system for behavior modification as defined in claim 1 further comprising:
    an interface subsystem configured to receive other information from at least one other source, said interface subsystem configured to update said user-specific package and said pre-selected problem-identification rules in accordance with said other information
    a data analyst subsystem configured to receive said user specific information and said other information to produce analyzed data, said data analyst subsystem further configured to update said user-specific package with said analyzed data; and a monitor subsystem configured to
automatically track actions of the user associated with the at least one behavior problem;
automatically update said user-specific package with the actions;
automatically compare said user-specific package to the updated user-specific package to provide compared data,
automatically update said user-specific package with said compared data;
wherein said package designer subsystem further:
automatically modifies said user-specific program based on the updated user-specific package;
automatically develops said electronic feedback to be presented to the user based on the updated user-specific package and the modified user-specific program;
automatically adds said electronic feedback to the updated user-specific package; and
stores the updated user-specific package on a computer-readable medium.

3. The system for behavior modification as defined in claim 2 wherein said at least one other source is a professional.

4. The system for behavior modification as defined in claim 2 wherein said at least one other source is a nutrition provider.

5. The system for behavior modification as defined in claim 4 wherein said nutrition provider further comprises:
at least one food source, said food source providing at least one food list, said at least one food list being analyzed by said data analyst subsystem to produce nutrition data;
wherein said data analyst subsystem updates said user-specific package with said nutrition data, said at least one food source, and said at least one food list.

6. The system for behavior modification as defined in claim 2 wherein said at least one other source is a fitness provider.

7. The system for behavior modification as defined in claim 2 wherein said at least one other source is a service provider.

8. The system for behavior modification as defined in claim 2 wherein said at least one other source is an expert.

9. The system for behavior modification as defined in claim 1 wherein said user-specific information includes emotional, behavioral, physical, and environmental characteristics of the user.

10. The system for behavior modification as defined in claim 1 wherein said feedback includes advice, congratulatory messages, anthropogenic feedback, and animated feedback.

11. A method for modifying behavior comprising the steps of:
(a) receiving user information from the user and other information from at least one source besides the user from at least one computer-readable user interface;
(b) accessing problem-identification rules that are linked to behavior problems;
(c) identifying the behavior problems associated with a user based on the problem-identification rules, the user information, and the other information;
(d) producing a user-specific package having the user information, the other information, the behavior problems, recommendations, and action plans derived for the user based on the behavior problems, the user information, and other information;
(e) tracking actions of the user with respect to the identified behavior problems;
(f) designing a step-by-step program of behavior modification to address reasons underlying the identified problems as identified in said step of tracking;
(g) providing the user an electronic feedback with the step-by-step program, recommendations, integrated and dynamically changing action plan, tips, monitoring, and compliance advisories to instruct the user in modifying behavior associated with the identified problems; and
(h) receiving undated user-specific information from the user after the user has reviewed said electronic feedback, and processing the undated user-specific information to update said user-specific package and said user-specific program indicating that the user has modified said at least one behavior problem based upon said electronic feedback.

12. The method for modifying behavior as defined in claim 11 wherein user information includes behavioral, emotional, environmental, and physical characteristics.

13. The method for modifying behavior as defined in claim 11 wherein other information includes professional advice.

14. The method for modifying behavior as defined in claim 11 wherein other information includes nutritional information.

15. The method for modifying behavior as defined in claim 11 wherein other information includes fitness information.

16. The method for modifying behavior as defined in claim 11 further comprising the steps of:
(h) receiving further user information and further other information;
(i) analyzing the further user information and the further other information to produce updated analyzed data; and
(j) updating the user-specific package with the updated analyzed data.

17. The method for modifying behavior as defined in claim 16 further comprising the steps of:
(k) analyzing the updated analyzed data during a pre-selected period of time to detect changes in behavior of the user;
(l) adjusting the user information based on said step (k);
(m) notifying the user of the changes in behavior; and
(n) modifying the at least one computer-readable user interface if there are the changes in behavior.

18. The method for modifying behavior as defined in claim 17 further comprising the steps of:
(n) associating the rules with a general database, the general database providing system-wide information relevant to behavior modification;
(o) enabling update of the general database;
(p) updating the user-specific package based on the updated general database;
(q) enabling communication between at least one personal device and at least one multi-user device, the at least one personal device having a unique identification;
(r) establishing a relationship between the unique identification and the user login;
(s) receiving a login request from the user;
(t) validating the login request based on the relationship; and
(u) synchronizing the user-specific package between the at least one personal device and the at least one multi-user device.

19. The method for modifying behavior as defined in claim 18 wherein the step of updating and synchronizing further comprises the steps of:
(v) preparing a filter to select user-specific information from the general database;
(w) preparing a general database subset based on the filter and the general database; and (x) transferring the general database subset from the at least one multi-user device to the at least one personal device.

20. A memory containing instructions for the practice of the method according to claim 11.

21. A system having computer memory containing instructions for implementing behavior modification of a user comprising:
- a data collector subsystem configured to receive user information from a user, said data collector subsystem configured to update a user-specific package with said user information;
- a data analyst subsystem configured to analyze said user information to produce analyzed data, said data analyst subsystem configured to access rules from a general database, said data analyst subsystem configured to update said user-specific package with said analyzed data and said rules;
- a package designer subsystem configured to determine at least one type of behavior associated with the user based on said user-specific package, said package designer subsystem configured to create a user-specific program for behavior modification based on said user-specific package; wherein said user-specific program includes recommendations and action plans that are uniquely derived for the user based on said at least one type of behavior and said user-specific package; said package designer subsystem configured to select feedback based on said at least one type of behavior and said user-specific package, said package designer subsystem configured to update said user-specific package with said at least one type of behavior, said user-specific program for behavior modification, and said feedback;
- a feedback provider subsystem configured to present said feedback to the user based on said user-specific program, including said recommendations, and including integrated and dynamically changing action plans, tips, monitoring and compliance advisories;
- and a monitor subsystem configured to compare said user information and said analyzed data to said at least one type of behavior to provide compared data, said monitor subsystem configured to continually update the user-specific package with the compared data.

22. The system for behavior modification as defined in claim 21 wherein said user-specific package comprises:
- a profile/package database populated with said user information, said analyzed data, said rules, said at least one type of behavior, said feedback, and said compared data; and
- a user-specific filter configured to select data from the general database, said selection based on said user-specific package.

23. The system for behavior modification as defined in claim 21 further comprising:
- a user registrar subsystem configured to receive said user information, said user information including login information; said user registrar subsystem configured to enable communication between at least one personal device and at least one multi-user device, the at least one personal device having a unique identification, said user registrar subsystem configured to establish a relationship between the unique identification and the login information, said user registrar subsystem configured to receive a login request from the user, said user registrar subsystem configured to validate the login request based on said relationship, said user registrar subsystem configured to enable updating and synchronizing said user-specific package between the at least one personal device and the at least one multi-user device.

24. The system for behavior modification as defined in claim 23 further comprising:
- an expert subsystem configured to receive at least one update to said general database, said expert subsystem configured to update said general database with said at least one update, said expert subsystem configured to incorporate said at least one update in said user-specific package, said expert subsystem configured to proliferate said at least one update to said at least one personal device.

25. The system for behavior modification as defined in claim 21 further comprising:
- a professional interface subsystem configured to receive augmentary information from at least one source, said professional interface subsystem configured to update said user-specific package and said rules according to said augmentary information received from the at least one source.

26. A system having computer memory containing instructions for implementing behavior modification of a user comprising:
- a data collector configured to collect user-specific data from a user and from at least one collaborative source, said user-specific data related to at least one pre-defined parameter;
- a data analyst configured to identify pre-defined data, said data analyst configured to analyze said user-specific data, said data analyst configured to store said user-specific data, said pre-defined data, said at least one pre-defined parameter, said analyzed data, and relationships among said user-specific data, said pre-defined data, said at least one pre-defined parameter, and said analyzed data in a plurality of user-specific packages, said pre-defined data including at least one behavior pattern and feedback, said data analyst configured to define executable code in said plurality of user-specific packages, said executable code configured to perform at least one action on a second element in said plurality of user-specific packages in response to a change in a first element in said plurality of user-specific packages;
- at least one collaborative source configured to create customized pre-defined data in said plurality of user-specific packages, said customized pre-defined data being related to said pre-defined data;
- a package designer configured to identify at least one user-specific pattern based on said plurality of user-specific packages, said package designer configured to identify user-specific feedback related to said at least one user-specific pattern, said at least one pre-defined parameter, and at least one other element from said plurality of user-specific packages, said user-specific feedback including at least one characteristic;
- an expert configured to define said at least one action to be a database update, said database update providing for updating said second element and other elements related to said second element; wherein said package designer is configured to create a user-specific program for behavior modification based on said at least one user-specific pattern; wherein said user-specific program includes recommendations and action plans that are uniquely derived for the user based on at least one behavior problem and said user-specific data; said expert configured to update said first element, thereby invoking said executable code, thereby updating said plurality of user-specific packages; and a feedback provider configured to present said user-specific feedback to the user based on said user-specific program, including said recommendations, and including integrated and dynamically changing action plans, tips, monitoring, and compliance advisories, said user-specific feedback configured to assist the user in behavior modification.

27. The system as defined in claim 26 wherein said package designer is configured to define said at least one user-specific pattern as said first element, wherein said package designer is configured to define said user-specific feedback as said second element.

28. The system as defined in claim 26 wherein said package designer is configured to define said user-specific feedback as said first element, wherein said package designer is configured to define said at least one user-specific pattern as said second element.

29. The system as defined in claim 26 further comprising:
a conduit configured to enable electronic transfer of at least one of said plurality of user-specific packages between a server and a personal device, the personal device being related to said at least one of said plurality of user-specific packages, said conduit configured to synchronize said at least one of said plurality of user-specific packages between the server and the personal device;
wherein said at least one of said plurality of user-specific packages is shared between the server and the personal device, wherein said first element is defined to be a server database element, wherein said second element is defined to be a personal device database element, wherein said expert is configured to update said server database element, thereby invoking said executable code, thereby updating said personal device database element.

30. The system as defined in claim 29 further comprising:
a user registrar configured to communicate with said conduit, said user registrar configured to determine an identity for the personal device, said user registrar configured to allow access to said conduit based on said identity.

31. The system as defined in claim 26 further comprising:
a group database having at least one element in common with said plurality of user-specific packages; and
a professional interface configured to review update instructions, said professional interface configured to define said first element to be a group database element from said group database, said professional interface configured to define said second element to be a user-specific package element from said plurality of user-specific packages, said professional interface configured to update said group database element according to said update instructions, thereby invoking said executable code, thereby updating said user-specific package element, thereby updating said plurality of user-specific packages.

32. The system as defined in claim 31 wherein said professional interface is configured to update said group database and to archive said updated group database.

33. The system as defined in claim 31 further comprising:
a conduit configured to enable electronic transfer of at least one of said plurality of user-specific packages between a server and a personal device, the personal device being related to said at least one of said plurality of user-specific packages, said conduit configured to synchronize said at least one of said plurality of user-specific packages between the server and the personal device;
wherein said at least one of said plurality of user-specific packages is shared between the server and the personal device, wherein said first element is defined to be a server database element, wherein said second element is defined to be a personal device database element, wherein said professional interface is configured to update said server database element, thereby invoking said executable code, thereby updating said personal device database element.

34. The system as defined in claim 26 further comprising:
a general database having at least one general database element in common with said plurality of user-specific packages; and
an expert interface configured to receive update instructions from a first user, said first user configured to define said first element to be said at least one general database element, said first user configured to define said second element to be a user-specific package element, said first user configured to update said at least one general database element according to said update instructions, thereby invoking said executable code, thereby updating said user-specific package element, thereby updating said plurality of user-specific packages.

35. The system as defined in claim 26 further comprising:
a continuous monitor configured to dynamically direct said data collector to collect a dynamic subset of said user-specific data, said dynamic subset being determined according to said user-specific feedback, said continuous monitor configured to dynamically direct said data analyst to analyze said dynamic subset based on said plurality of user-specific packages, said continuous monitor configured to dynamically direct said data analyst to store said dynamic subset and said analyzed dynamic subset in said plurality of user-specific packages.

36. The system as defined in claim 26 further comprising:
a profile maintainer configured to define said first element to be said at least one user-specific pattern, said profile maintainer configured to define said second element to be said user-specific feedback, said profile maintainer configured to update said at least one user-specific pattern based on said dynamic subset, thereby invoking said executable code, thereby updating said user-specific feedback, thereby updating said dynamic subset.

* * * * *